US012433747B2

(12) United States Patent
Levi et al.

(10) Patent No.: US 12,433,747 B2
(45) Date of Patent: Oct. 7, 2025

(54) COMMISSURE ATTACHMENT FOR PROSTHETIC HEART VALVE

(71) Applicant: Edwards Lifesciences Corporation, Irvine, CA (US)

(72) Inventors: Tamir S. Levi, Zikhron Yaakov (IL); Noam Nir, Pardes-Hanna (IL); Michael Bukin, Pardes Hanna (IL); David Maimon, Atlit (IL); Haim Yushtein, Netanya (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 928 days.

(21) Appl. No.: 17/466,331

(22) Filed: Sep. 3, 2021

(65) Prior Publication Data

US 2021/0393398 A1 Dec. 23, 2021

Related U.S. Application Data

(63) Continuation of application No. PCT/US2020/018664, filed on Feb. 18, 2020.

(Continued)

(51) Int. Cl.
*A61F 2/24* (2006.01)

(52) U.S. Cl.
CPC ............ *A61F 2/243* (2013.01); *A61F 2/2418* (2013.01); *A61F 2220/0091* (2013.01)

(58) Field of Classification Search
CPC .................... A61F 2/243; A61F 2/2418; A61F 2220/0091; A61F 2/2412; A61F 2/2439;

(Continued)

(56) References Cited

U.S. PATENT DOCUMENTS

| | | | |
|---|---|---|---|
| 3,409,013 | A | 11/1968 | Berry |
| 3,548,417 | A | 12/1970 | Kisher |

(Continued)

FOREIGN PATENT DOCUMENTS

| | | | |
|---|---|---|---|
| DE | 0144167 | C | 9/1903 |
| DE | 2246526 | A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Jerrah Edwards
*Assistant Examiner* — Kia Xiong White
(74) *Attorney, Agent, or Firm* — Klarquist Sparkman, LLP; Joel B. German

(57) ABSTRACT

A prosthetic heart valve includes an annular frame that is radially collapsible and radially expandable, a plurality of leaflets situated within the frame, each leaflet having opposing commissure tab portions on opposite sides of the leaflet, each commissure tab portion paired with an adjacent commissure tab portion of an adjacent leaflet to form at least one commissure, and a plurality of post members mounted on an interior surface of the frame. The at least one commissure includes a commissure attachment assembly including a support member disposed at least partially around the commissure tab portions and the commissure tab portions are folded around the support member. The commissure attachment assembly is secured to a first post member of the plurality of post members such that the commissure tab portions are positioned between the first post member and the support member.

23 Claims, 23 Drawing Sheets

Related U.S. Application Data

(60) Provisional application No. 62/813,643, filed on Mar. 4, 2019.

(58) Field of Classification Search
CPC ........ A61F 2220/0041; A61F 2250/001; A61F 2/24
See application file for complete search history.

(56) References Cited

U.S. PATENT DOCUMENTS

| | | | |
|---|---|---|---|
| 3,587,115 | A | 6/1971 | Shiley |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| RE30,912 | E | 4/1982 | Hancock |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,441,216 | A | 4/1984 | Ionescu et al. |
| 4,470,157 | A | 9/1984 | Love |
| 4,535,483 | A | 8/1985 | Klawitter et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,820,299 | A | 4/1989 | Philippe et al. |
| 4,829,990 | A | 5/1989 | Thuroff et al. |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,266,073 | A | 11/1993 | Wall |
| 5,282,847 | A | 2/1994 | Trescony et al. |
| 5,295,958 | A | 3/1994 | Shturman |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,558,644 | A | 9/1996 | Boyd et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,792 | A | 5/1997 | Lentell |
| 5,639,274 | A | 6/1997 | Fischell et al. |
| 5,665,115 | A | 9/1997 | Cragg |
| 5,716,417 | A | 2/1998 | Girard et al. |
| 5,728,068 | A | 3/1998 | Leone et al. |
| 5,749,890 | A | 5/1998 | Shaknovich |
| 5,756,476 | A | 5/1998 | Epstein et al. |
| 5,769,812 | A | 6/1998 | Stevens et al. |
| 5,800,508 | A | 9/1998 | Goicoechea et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,925,063 | A | 7/1999 | Khosravi |
| 5,957,949 | A | 9/1999 | Leonhardt et al. |
| 6,027,525 | A | 2/2000 | Suh et al. |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,299,637 | B1 | 10/2001 | Shaolian et al. |
| 6,302,906 | B1 | 10/2001 | Goicoechea et al. |
| 6,338,740 | B1 | 1/2002 | Carpentier |
| 6,350,277 | B1 | 2/2002 | Kocur |
| 6,352,547 | B1 | 3/2002 | Brown et al. |
| 6,425,916 | B1 | 7/2002 | Garrison et al. |
| 6,440,764 | B1 | 8/2002 | Focht et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,527,979 | B2 | 3/2003 | Constantz et al. |
| 6,569,196 | B1 | 5/2003 | Vesely |
| 6,582,462 | B1 | 6/2003 | Andersen et al. |
| 6,605,112 | B1 | 8/2003 | Moll et al. |
| 6,652,578 | B2 | 11/2003 | Bailey et al. |
| 6,689,123 | B2 | 2/2004 | Pinchasik |
| 6,716,244 | B2 | 4/2004 | Klaco |
| 6,730,118 | B2 | 5/2004 | Spenser et al. |
| 6,733,525 | B2 | 5/2004 | Yang et al. |
| 6,767,362 | B2 | 7/2004 | Schreck |
| 6,769,161 | B2 | 8/2004 | Brown et al. |
| 6,783,542 | B2 | 8/2004 | Eidenschink |
| 6,830,584 | B1 | 12/2004 | Seguin |
| 6,878,162 | B2 | 4/2005 | Bales et al. |
| 6,893,460 | B2 | 5/2005 | Spenser et al. |
| 6,908,481 | B2 | 6/2005 | Cribier |
| 6,936,067 | B2 | 8/2005 | Buchanan |
| 7,018,406 | B2 | 3/2006 | Seguin et al. |
| 7,018,408 | B2 | 3/2006 | Bailey et al. |
| 7,096,554 | B2 | 8/2006 | Austin et al. |
| 7,225,518 | B2 | 6/2007 | Eidenschink et al. |
| 7,276,078 | B2 | 10/2007 | Spenser et al. |
| 7,276,084 | B2 | 10/2007 | Yang et al. |
| 7,316,710 | B1 | 1/2008 | Cheng et al. |

(56) References Cited

U.S. PATENT DOCUMENTS

| | | | |
|---|---|---|---|
| 7,318,278 | B2 | 1/2008 | Zhang et al. |
| 7,374,571 | B2 | 5/2008 | Pease et al. |
| 7,393,360 | B2 | 7/2008 | Spenser et al. |
| 7,462,191 | B2 | 12/2008 | Spenser et al. |
| 7,510,575 | B2 | 3/2009 | Spenser et al. |
| 7,563,280 | B2 | 7/2009 | Anderson et al. |
| 7,585,321 | B2 | 9/2009 | Cribier |
| 7,618,446 | B2 | 11/2009 | Andersen et al. |
| 7,618,447 | B2 | 11/2009 | Case et al. |
| 7,655,034 | B2 | 2/2010 | Mitchell et al. |
| 7,785,366 | B2 | 8/2010 | Maurer et al. |
| 7,959,665 | B2 | 6/2011 | Pienknagura |
| 7,959,672 | B2 | 6/2011 | Salahieh et al. |
| 7,993,394 | B2 | 8/2011 | Hariton et al. |
| 8,029,556 | B2 | 10/2011 | Rowe |
| 8,075,611 | B2 | 12/2011 | Millwee et al. |
| 8,128,686 | B2 | 3/2012 | Paul, Jr. et al. |
| 8,167,932 | B2 | 5/2012 | Bourang et al. |
| 8,291,570 | B2 | 10/2012 | Fidenschink et al. |
| 8,348,998 | B2 | 1/2013 | Pintor et al. |
| 8,449,606 | B2 | 5/2013 | Eliasen et al. |
| 8,454,685 | B2 | 6/2013 | Hariton et al. |
| 8,652,203 | B2 | 2/2014 | Quadri et al. |
| 8,685,055 | B2 | 4/2014 | VanTassel et al. |
| 8,747,463 | B2 | 6/2014 | Fogarty et al. |
| 9,078,781 | B2 | 7/2015 | Ryan et al. |
| 2001/0021872 | A1 | 9/2001 | Bailey et al. |
| 2002/0026094 | A1 | 2/2002 | Roth |
| 2002/0032481 | A1 | 3/2002 | Gabbay |
| 2002/0138135 | A1 | 9/2002 | Duerig et al. |
| 2002/0143390 | A1 | 10/2002 | Ishii |
| 2002/0173842 | A1 | 11/2002 | Buchanan |
| 2003/0014105 | A1 | 1/2003 | Cao |
| 2003/0040791 | A1 | 2/2003 | Oktay |
| 2003/0050694 | A1 | 3/2003 | Yang et al. |
| 2003/0100939 | A1 | 5/2003 | Yodfat et al. |
| 2003/0158597 | A1 | 8/2003 | Quiachon et al. |
| 2003/0212454 | A1 | 11/2003 | Scott et al. |
| 2004/0024452 | A1 | 2/2004 | Kruse et al. |
| 2004/0039436 | A1 | 2/2004 | Spenser et al. |
| 2004/0078074 | A1 | 4/2004 | Anderson et al. |
| 2004/0186558 | A1 | 9/2004 | Pavcnik et al. |
| 2004/0186563 | A1* | 9/2004 | Lobbi .................. A61F 2/2418 623/2.11 |
| 2004/0186565 | A1 | 9/2004 | Schreck |
| 2004/0260389 | A1 | 12/2004 | Case et al. |
| 2005/0010285 | A1 | 1/2005 | Lambrecht et al. |
| 2005/0075725 | A1 | 4/2005 | Rowe |
| 2005/0075728 | A1 | 4/2005 | Nguyen et al. |
| 2005/0096736 | A1 | 5/2005 | Osse et al. |
| 2005/0096738 | A1 | 5/2005 | Cali et al. |
| 2005/0137686 | A1 | 6/2005 | Salahieh et al. |
| 2005/0188525 | A1 | 9/2005 | Weber et al. |
| 2005/0203614 | A1 | 9/2005 | Forster et al. |
| 2005/0203617 | A1 | 9/2005 | Forster et al. |
| 2005/0234546 | A1 | 10/2005 | Nugent et al. |
| 2006/0004469 | A1 | 1/2006 | Sokel |
| 2006/0025857 | A1 | 2/2006 | Bergheim et al. |
| 2006/0058872 | A1 | 3/2006 | Salahieh et al. |
| 2006/0074484 | A1 | 4/2006 | Huber |
| 2006/0108090 | A1 | 5/2006 | Ederer et al. |
| 2006/0149350 | A1 | 7/2006 | Patel et al. |
| 2006/0183383 | A1 | 8/2006 | Asmus et al. |
| 2006/0229719 | A1 | 10/2006 | Marquez et al. |
| 2006/0259136 | A1 | 11/2006 | Nguyen et al. |
| 2006/0259137 | A1 | 11/2006 | Artof et al. |
| 2006/0287717 | A1 | 12/2006 | Rowe et al. |
| 2007/0005131 | A1 | 1/2007 | Taylor |
| 2007/0010876 | A1 | 1/2007 | Salahieh et al. |
| 2007/0010877 | A1 | 1/2007 | Salahieh et al. |
| 2007/0112422 | A1 | 5/2007 | Dehdashtian |
| 2007/0162102 | A1 | 7/2007 | Ryan et al. |
| 2007/0203503 | A1 | 8/2007 | Salahieh et al. |
| 2007/0203575 | A1 | 8/2007 | Forster et al. |
| 2007/0203576 | A1 | 8/2007 | Lee et al. |
| 2007/0208550 | A1 | 9/2007 | Cao et al. |
| 2007/0213813 | A1 | 9/2007 | Von Segesser et al. |
| 2007/0233228 | A1 | 10/2007 | Eberhardt et al. |
| 2007/0260305 | A1 | 11/2007 | Drews et al. |
| 2007/0265700 | A1 | 11/2007 | Eliasen et al. |
| 2008/0021546 | A1 | 1/2008 | Patz et al. |
| 2008/0114442 | A1 | 5/2008 | Mitchell et al. |
| 2008/0125853 | A1 | 5/2008 | Bailey et al. |
| 2008/0154355 | A1 | 6/2008 | Benichou et al. |
| 2008/0183271 | A1 | 7/2008 | Frawley et al. |
| 2008/0208327 | A1 | 8/2008 | Rowe |
| 2008/0243245 | A1 | 10/2008 | Thambar et al. |
| 2008/0255660 | A1 | 10/2008 | Guyenot et al. |
| 2008/0275537 | A1 | 11/2008 | Limon |
| 2008/0294248 | A1 | 11/2008 | Yang et al. |
| 2009/0118826 | A1 | 5/2009 | Khaghani |
| 2009/0125118 | A1 | 5/2009 | Gong |
| 2009/0157175 | A1 | 6/2009 | Benichou |
| 2009/0276040 | A1 | 11/2009 | Rowe et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0299452 | A1 | 12/2009 | Eidenschink et al. |
| 2009/0319037 | A1 | 12/2009 | Rowe et al. |
| 2010/0004735 | A1 | 1/2010 | Yang et al. |
| 2010/0049313 | A1 | 2/2010 | Alon et al. |
| 2010/0082094 | A1 | 4/2010 | Quadri et al. |
| 2010/0100176 | A1 | 4/2010 | Elizondo et al. |
| 2010/0168844 | A1 | 7/2010 | Toomes et al. |
| 2010/0185277 | A1 | 7/2010 | Braido et al. |
| 2010/0198347 | A1 | 8/2010 | Zakay et al. |
| 2010/0204781 | A1 | 8/2010 | Alkhatib |
| 2010/0262231 | A1* | 10/2010 | Tuval .................... A61F 2/2409 623/2.4 |
| 2011/0015729 | A1 | 1/2011 | Jimenez et al. |
| 2011/0022157 | A1 | 1/2011 | Essinger et al. |
| 2011/0066224 | A1 | 3/2011 | White |
| 2011/0137397 | A1 | 6/2011 | Chau et al. |
| 2011/0218619 | A1 | 9/2011 | Benichou et al. |
| 2011/0319991 | A1 | 12/2011 | Hariton et al. |
| 2012/0030090 | A1 | 2/2012 | Johnston et al. |
| 2012/0089223 | A1 | 4/2012 | Nguyen et al. |
| 2012/0101571 | A1 | 4/2012 | Thambar et al. |
| 2012/0123529 | A1 | 5/2012 | Evi et al. |
| 2012/0259409 | A1 | 10/2012 | Nguyen et al. |
| 2013/0023985 | A1 | 1/2013 | Khairkhahan et al. |
| 2013/0046373 | A1 | 2/2013 | Cartledge et al. |
| 2013/0150956 | A1* | 6/2013 | Yohanan ............... A61F 2/2418 623/2.14 |
| 2013/0166017 | A1* | 6/2013 | Cartledge ............. A61F 2/2439 623/1.2 |
| 2013/0190857 | A1 | 7/2013 | Mitra et al. |
| 2013/0274873 | A1 | 10/2013 | Delaloye et al. |
| 2013/0310926 | A1 | 11/2013 | Hariton |
| 2013/0317598 | A1 | 11/2013 | Rowe et al. |
| 2013/0331929 | A1 | 12/2013 | Mitra et al. |
| 2014/0194981 | A1 | 7/2014 | Menk et al. |
| 2014/0200661 | A1 | 7/2014 | Pintor et al. |
| 2014/0209238 | A1 | 7/2014 | Bonyuet et al. |
| 2014/0222136 | A1 | 8/2014 | Geist et al. |
| 2014/0277417 | A1 | 9/2014 | Schraut et al. |
| 2014/0277419 | A1 | 9/2014 | Garde et al. |
| 2014/0277424 | A1 | 9/2014 | Oslund |
| 2014/0277563 | A1 | 9/2014 | White |
| 2014/0296962 | A1 | 10/2014 | Cartledge et al. |
| 2014/0330372 | A1 | 11/2014 | Weston et al. |
| 2014/0343670 | A1 | 11/2014 | Bakis et al. |
| 2014/0343671 | A1 | 11/2014 | Yohanan et al. |
| 2014/0350667 | A1 | 11/2014 | Braido et al. |
| 2015/0073545 | A1 | 3/2015 | Braido |
| 2015/0073546 | A1 | 3/2015 | Braido |
| 2015/0135506 | A1 | 5/2015 | White |
| 2015/0157455 | A1 | 6/2015 | Hoang et al. |
| 2016/0175096 | A1* | 6/2016 | Dienno ................ A61F 2/2415 623/2.13 |
| 2016/0374802 | A1 | 12/2016 | Levi et al. |
| 2017/0014229 | A1 | 1/2017 | Nguyen-Thien-Nhon et al. |
| 2018/0028310 | A1 | 2/2018 | Gurovich et al. |
| 2018/0153689 | A1 | 6/2018 | Maimon et al. |

(56) References Cited

U.S. PATENT DOCUMENTS

| | | | |
|---|---|---|---|
| 2018/0325665 A1 | 11/2018 | Gurovich et al. |
| 2018/0344456 A1 | 12/2018 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |

FOREIGN PATENT DOCUMENTS

| | | | |
|---|---|---|---|
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | A1 | 3/1984 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 9117720 | A1 | 11/1991 |
| WO | 9217118 | A1 | 10/1992 |
| WO | 9301768 | A1 | 2/1993 |
| WO | 9724080 | A1 | 7/1997 |
| WO | 9829057 | A1 | 7/1998 |
| WO | 9930646 | A1 | 6/1999 |
| WO | 9933414 | A1 | 7/1999 |
| WO | 9940964 | A1 | 8/1999 |
| WO | 9947075 | A1 | 9/1999 |
| WO | 0018333 | A1 | 4/2000 |
| WO | 0041652 | A1 | 7/2000 |
| WO | 0135878 | A2 | 5/2001 |
| WO | 0149213 | A2 | 7/2001 |
| WO | 0154624 | A1 | 8/2001 |
| WO | 0154625 | A1 | 8/2001 |
| WO | 0162189 | A1 | 8/2001 |
| WO | 0047139 | A9 | 9/2001 |
| WO | 0164137 | A1 | 9/2001 |
| WO | 0176510 | A2 | 10/2001 |
| WO | 0222054 | | 3/2002 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 0249540 | A2 | 6/2002 |
| WO | 03047468 | | 6/2003 |
| WO | 2005034812 | A1 | 4/2005 |
| WO | 2005055883 | A1 | 6/2005 |
| WO | 2005084595 | A1 | 9/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2005102015 | A3 | 4/2007 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

COMMISSURE ATTACHMENT FOR PROSTHETIC HEART VALVE

CROSS REFERENCE TO RELATED APPLICATIONS

This application is a continuation of PCT Patent Application No. PCT/US2020/018664, filed Feb. 18, 2020, which claims the benefit of U.S. Provisional Application No. 62/813,643, filed Mar. 4, 2019, all of which applications are incorporated herein by reference.

FIELD

The present disclosure relates to implantable, mechanically expandable prosthetic devices, such as prosthetic heart valves, and to methods and assemblies for forming leaflet commissures in such prosthetic devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering attention. In one technique, a prosthetic valve is configured to be implanted in a much less invasive procedure by way of catheterization. For instance, U.S. Patent Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design consideration is attachment of the leaflets to the frame of the prosthetic valve to form commissures. The precise leaflet alignment required, and the need to prevent axial slipping or rotation of the leaflets during crimping, as well as during valve operation, can make commissure assembly difficult and time-consuming. It is also desirable to make commissures and the associated attachment hardware as small as practicable to minimize the diameter of the prosthetic valve in the collapsed state.

Accordingly, there is a need for improvements to devices and methods for securing leaflets together and to frames of prosthetic heart valves to form commissures in prosthetic heart valves.

SUMMARY

Certain embodiments of the disclosure pertain to systems, methods, and assemblies for forming commissures, and for attaching the pre-assembled commissures onto a frame of a prosthetic heart valve.

In a representative embodiment, a prosthetic heart valve comprises an annular frame including a plurality of interconnected strut members, the frame being radially collapsible to a collapsed configuration and radially expandable to an expanded configuration. The prosthetic heart valve further comprises a plurality of leaflets situated within the frame, each leaflet comprising opposing commissure tab portions on opposite sides of the leaflet, each commissure tab portion being paired with an adjacent commissure tab portion of an adjacent leaflet to form at least one commissure. The prosthetic heart valve further comprises a plurality of post members mounted on an interior surface of the frame. The at least one commissure comprises a commissure attachment assembly, the commissure attachment assembly comprising a support member secured to the paired commissure tab portions on one side of the at least one commissure such that each commissure tab portion comprises a fold. The at least one commissure further comprises a reinforcement member positioned in the fold of each commissure tab portion and secured to the support member through the commissure tab portion. The commissure attachment assembly is secured to a first post member of the plurality of post members.

In some embodiments, the reinforcement members and the commissure tab portions are secured to the support member by sutures, and the support member comprises openings configured to receive the sutures.

In some embodiments, one of the leaflets of the commissure attachment assembly is a first leaflet and the other leaflet of the commissure attachment assembly is a second leaflet, the support member comprises a first row of openings to receive sutures securing the first leaflet to the support member, and the support member comprises a second row of openings offset from the first row of openings, the second row of openings being configured to receive sutures securing the second leaflet to the support member.

In some embodiments, the openings of the support member are arranged in a row along a center of the support member.

In some embodiments, one of the leaflets of the commissure attachment assembly is a first leaflet and the other leaflet of the commissure attachment assembly is a second leaflet, and the sutures securing the first leaflet to the support member extend through the openings of the support member at an angle to the sutures securing the second leaflet to the support member.

In some embodiments, the support member of the commissure attachment assembly is positioned between the commissure tab portions and the first post member.

In some embodiments, the frame is a mechanically-expandable frame, and the post members comprise actuator components configured to mechanically expand and collapse the frame.

In some embodiments, the at least one commissure is one of a plurality of commissures, and each of the plurality of commissures comprises a commissure attachment assembly.

In another representative embodiment, a prosthetic heart valve comprises an annular frame including a plurality of interconnected strut members, the frame being radially collapsible to a collapsed configuration and radially expandable to an expanded configuration. The prosthetic heart valve further comprises a plurality of leaflets situated within the frame, each leaflet comprising opposing commissure tab portions on opposite sides of the leaflet, each commissure tab portion being paired with an adjacent commissure tab portion of an adjacent leaflet to form at least one commissure. A plurality of post members are mounted on an interior surface of the frame. The at least one commissure comprises a commissure attachment assembly, the commissure attachment assembly comprising a support member disposed at least partially around the commissure tab portions such that the commissure tab portions extend through the support member. The commissure tab portions of the commissure attachment assembly are folded around the support member, and the commissure attachment assembly is secured to a first post member of the plurality of post members such that the commissure tab portions are positioned between the first post member and the support member.

In some embodiments, the support member comprises a central opening through which the commissure tab portions extend.

In some embodiments, the support member comprises a U-shaped member disposed at least partially around the commissure tab portions.

In some embodiments, one of the leaflets of the commissure attachment assembly is a first leaflet and the other leaflet of the commissure attachment assembly is a second leaflet. The support member comprises a first row of openings to receive sutures securing the first leaflet to the support member, and the support member comprises a second row of openings offset from the first row of openings, the second row of openings being configured to receive sutures securing the second leaflet to the support member.

In some embodiments, the first row of openings and the second row of openings are on opposite sides of the commissure tab portions from each other.

In some embodiments, the commissure attachment assembly further comprises a first reinforcement member configured to clamp the commissure tab portion of the first leaflet to the support member, and a second reinforcement member configured to clamp the commissure tab portion of the second leaflet to the support member.

In some embodiments, the first reinforcement member comprises a row of openings aligned with the first row of openings of the support member, and the second reinforcement member comprises a row of openings aligned with the second row of openings of the support member.

In some embodiments, the support member is configured to engage the first post member to hold the commissure attachment assembly in place.

In some embodiments, the support member comprises a plurality of barbs extending through the commissure tab portions, and the first post member comprises a plurality of openings configured to receive the barbs.

In some embodiments, the frame is a mechanically-expandable frame, and the post members comprise actuator components configured to mechanically expand and collapse the frame.

In some embodiments, at least a portion of the support member comprises a flexible material and the support member comprises a central opening through which the commissure tab portions extend.

In some embodiments, the support member comprises a central opening through which the commissure tab portions extend and the support member is configured to clamp the commissure tab portions within the central opening.

In some embodiments, the support member is configured to bend in an outward radial direction, relative to a central longitudinal axis of the frame, between a relaxed state and a bent state. A width of the central opening is smaller when the support member is in the bent state.

In some embodiments, the support member is in the bent state when it is secured to the first post member. Inner edges of the central opening are configured to exert a clamping force against the commissure tab portions arranged therein when the support member is in the bent state.

In some embodiments, the support member is configured to bend around a central longitudinal axis of the support member between a bent state and a released and unbent state. When the support member is in the bent state a width of the central opening is a wider, first width, and when the support member is in the released and unbent state the width of the central opening is a narrower, second width and side edges of the central opening exert a force against a portion of the commissure tab portions arranged therein.

In some embodiments, the central opening of the support member is defined by two side portions of the support member, the two side portions arranged on opposing sides of the central opening. A width of the central opening is defined between its side edges. Further, inner portions of the two side portions are arranged adjacent to respective side edges of the side edges, and when the commissure tab portions are arranged within the central window, the inner portions are bent radially outward and are biased against the commissure tab portions.

In some embodiments, the support member comprises a central opening through which the commissure tab portions extend and the central opening is I-shaped with a central longitudinal portion and two slots extending perpendicular to the central longitudinal portion at both ends thereof.

In some embodiments, the support member comprises a central opening through which the commissure tab portions extend and a plurality of openings arranged on either side of the central opening and the commissure attachment assembly is secured to the first post member via one or more elastically deformable attachment members. Each of the one or more elastically deformable attachment members extends through two oppositely arranged openings of the plurality of openings, loops around an outer side of the actuator member, and has end portions that are arranged within one or more channels that are recessed into a surface of the outer side of the actuator component.

In another representative embodiment, a prosthetic heart valve comprises an annular frame including a plurality of interconnected strut members, the frame being radially collapsible to a collapsed configuration and radially expandable to an expanded configuration, the frame comprising an inflow end and an outflow end. A plurality of leaflets are situated within the frame, each leaflet comprising opposing commissure tab portions on opposite sides of the leaflet, each commissure tab portion being paired with an adjacent commissure tab portion of an adjacent leaflet to form at least one commissure. A plurality of post members are mounted on an interior surface of the frame, each post member comprising a pair of retaining members spaced apart from each other and extending toward the outflow end of the frame. The commissure tab portions of the leaflets of the at least one commissure are inserted between the retaining members of a first post member of the plurality of post members to form the at least one commissure.

In some embodiments, the post members comprise openings configured to receive the retaining members.

In some embodiments, the prosthetic heart valve further comprises a fabric protective member wrapped at least partially around and secured to the commissure tab portions of the leaflets of the at least one commissure.

In some embodiments, the fabric protective member is wrapped around the retaining members of the first post member.

In some embodiments, the fabric protective member extends around the first post member.

In some embodiments, the prosthetic heart valve further comprises a cord member that extends around the retaining members of the first post member to urge the retaining members toward the first post member to grip the leaflets of the at least one commissure.

In some embodiments, the frame is a mechanically-expandable frame, and the post members comprise actuator components configured to mechanically expand and collapse the frame.

In yet another representative embodiment, a prosthetic heart valve comprises an annular frame including a plurality of interconnected strut members, the frame being radially collapsible to a collapsed configuration and radially expandable to an expanded configuration; a plurality of leaflets situated within the frame, each leaflet comprising opposing commissure tab portions on opposite sides of the leaflet, each commissure tab portion being paired with an adjacent commissure tab portion of an adjacent leaflet to form at least one commissure; and a plurality of post members mounted on an interior surface of the frame. The at least one commissure comprises a commissure attachment assembly, the commissure attachment assembly comprising a support member disposed at least partially around the commissure tab portions such that the commissure tab portions extend through a central opening of the support member. At least a portion of the support member comprises a flexible material and is configured to bend in a radially inward or outward direction relative to a central longitudinal axis of the frame. The commissure attachment assembly is secured to a first post member of the plurality of post members. The central opening is configured to apply a clamping force against the commissure tab portions arranged therein.

In some embodiments, the support member is configured to bend in an outward radial direction, relative to the central longitudinal axis, from a relaxed state to a bent state. The support member is in the bent state when it is secured to the first member. Inner edges of the central opening are arranged closer together when the support member is in the bent state, as compared to the relaxed state, and apply the clamping force against the commissure tab portions arranged therein.

In some embodiments, the central opening of the support member is defined by two side portions of the support member, the two side portions arranged on opposing sides of the central opening. A width of the inner edges of the central opening, in a radial direction, is wider than a remainder of the two side portions.

In some embodiments, the support member is configured to bend around a central longitudinal axis of the support member between a bent state and a released state, the central longitudinal axis of the support member arranged in parallel with the central longitudinal axis of the frame. When the support member is in the bent state a width of the central opening is a wider, first width, and when the support member is in the released state the width of the central opening is a narrower, second width and side edges of the central opening apply the clamping force against the commissure tab portions arranged therein.

In some embodiments, the support member is in the released state when the support member is secured to the first post member.

In some embodiments, the support member comprises a plastically deformable material.

In some embodiments, the central opening of the support member is defined by two side portions of the support member, the two side portions arranged on opposing sides of the central opening. A width of the central opening is defined between its side edges. Inner portions of the two side portions are arranged adjacent to respective side edges of the side edges and the inner portions are configured to bend in the radially outward direction in response to a force being applied thereto, in the radially outward direction.

In some embodiments, the commissure tab portions are arranged within the central window, the inner portions are bent radially outward, are biased against the commissure tab portions, and apply the clamping force against the commissure tab portions.

In some embodiments, the frame is a mechanically-expandable frame and the post members comprise actuator components configured to mechanically expand and collapse the frame.

In still another representative embodiment, a method for assembling a commissure attachment assembly to an annular frame of a prosthetic heart valve comprises: pairing a first commissure tab of a first leaflet with a second commissure tab of a second leaflet, wherein the first leaflet and the second leaflet are configured to be adjacently arranged within the frame, each leaflet comprising opposing commissure tabs arranged on opposite sides of the leaflet; inserting the paired first commissure tab and second commissure tab into and through a central opening of a support member, wherein ends of the paired first commissure tab and second commissure tab extend outward from a first side of the support member; extending one or more attachment members through one or more sets of apertures of the support member, respectively, wherein each set of apertures comprises an aperture arranged on either side of the central opening, and creating one or more loops that extend outward from the first side of the support member, the one or more loops having a diameter that is larger than an outer diameter of an actuator component of the frame, the actuator component adapted to receive and couple to the support member; axially aligning the support member and the actuator component so that the support member extends through the one or more loops, the one or more loops line up with corresponding circumferentially extending channels on an outer side of the actuator component, and the ends of the paired first commissure tab and second commissure tab are arranged between the support member and an inner side of the actuator component; tightening the one or more attachment members so that the one or more loops tighten around the actuator component, within their corresponding circumferentially extending channels; and for each attachment member: arranging free ends of the attachment member together; and further arranging the free ends within an axially extending central channel arranged in the outer surface of the actuator component.

In some embodiments, the one or more attachment members are elastically deformable.

In some embodiments, the one or more attachment members includes two attachment members spaced apart from one another. The circumferentially extending channels includes an upper channel and a lower channel. The axially extending central channel extends between the upper channel and the lower channel.

In some embodiments, the arranging the free ends of the attachment member together includes twisting the free ends together and arranging the twisted free ends within the axially extending central channel.

In some embodiments, the arranging the free ends of the attachment member together includes positioning the free ends adjacent to one another and wedging the adjacently arranged free ends into the axially extending central channel.

In some embodiments, the method further comprises folding the ends of the paired first commissure tab and second commissure tab over the first side of the support member such that they extend sideways along the first side of the support member, on either side of the central opening. The method further comprises, after extending the one or more attachment members through the one or more sets of apertures of the support member, further extending the one or more attachment members through the folded over ends of the paired first commissure tab and second commissure tab to secure the first commissure tab and the second commissure tab to the support member.

In some embodiments, the one or more attachment members are metallic wires.

In yet another representative embodiment, a prosthetic heart valve comprises: an annular frame including a plurality of interconnected strut members, the frame being radially collapsible to a collapsed configuration and radially expandable to an expanded configuration; a plurality of leaflets situated within the frame, each leaflet comprising opposing commissure tab portions on opposite sides of the leaflet, each commissure tab portion being paired with an adjacent commissure tab portion of an adjacent leaflet to form at least one commissure; and a plurality of post members mounted on an interior surface of the frame. Each post member comprises: an inner side facing a central longitudinal axis of the frame and comprising a commissure receiving portion; and an outer side facing the interior surface of the frame and comprising a plurality of channels recessed into a surface of the outer side. The at least one commissure comprises a commissure attachment assembly, the commissure attachment assembly comprising: a support member disposed around the commissure tab portions such that the commissure tab portions extend through a central opening of the support member and are folded around an outer side of the support member, the support member comprising a plurality of sets of apertures spaced axially apart along the support member, each set including one aperture arranged on either side of the central opening; and at least one attachment member extending through one set of apertures of the plurality of sets of apertures and forming a loop extending outward from the outer side of the support member. The commissure attachment assembly is secured to a first member of the plurality of post members such that the commissure tab portions are positioned against the commissure receiving portion of the first post and the loop of the at least one attachment member is tightened against and arranged within a circumferentially extending channel of the plurality of channels of the first post member.

In some embodiments, ends of the at least one attachment member extending from the loop are twisted together and arranged within an axially extending channel of the plurality of channels.

In some embodiments, the at least one attachment member comprises an elastically deformable material.

In some embodiments, the at least one attachment member comprises a metallic wire.

In some embodiments, the at least one attachment member comprises a first attachment member extending through a first set of apertures of the plurality of sets of apertures and a second attachment member extending through a second set of apertures of the plurality of sets of apertures, the first set of apertures and the second set of apertures spaced apart from one another in an axial direction relative to the central longitudinal axis.

In some embodiments, the plurality of channels includes a first circumferentially extending channel configured to receive a loop of the first attachment member and a second circumferentially extending channel configured to receive a loop of the second attachment member.

In some embodiments, the plurality of channels further comprises a central channel that extends in the axial direction, between the first circumferentially extending channel and the second circumferentially extending channel. First ends of the first attachment member are twisted together and arranged within the central channel and second ends of the second attachment member are twisted together and arranged within the central channel.

In some embodiments, the frame is a mechanically-expandable frame and the post members comprise actuator components configured to mechanically expand and collapse the frame.

In some embodiments, the inner side and the outer side of each post member are arranged on an actuator component and the actuator component is an outer housing of an actuator assembly of the frame.

In another representative embodiment, a method for assembling a commissure attachment assembly to an annular frame of a prosthetic heart valve can include: pairing a first commissure tab of a first leaflet with a second commissure tab of a second leaflet, wherein the first leaflet and the second leaflet are configured to be adjacently arranged within the frame, each leaflet comprising opposing commissure tabs arranged on opposite sides of the leaflet; inserting the paired first commissure tab and second commissure tab into and through a central opening of a support member that is in a relaxed state, wherein the central opening is defined between two side portions of the support member, and wherein the two side portions are arranged on opposing sides of the central opening; securing the support member to a post member mounted on an interior surface of the frame; and as the support member is secured to the post member, bending each of the two side portions of the support member in an outward radial direction, toward the post member, and moving inner edges of the central opening toward each other in order to exert a clamping force against portions of the first and second commissure tabs arranged therein, wherein the radial direction is relative to a central longitudinal axis of the annular frame.

In some embodiments, the securing causes the side portions of the support member to bend from the relaxed state to a bent state, wherein in the bent state the side portions bend toward or around the post member and a width of the central opening is decreased from the relaxed state.

In some embodiments, each side portion includes a plurality of openings and the securing includes extending one or more sutures through at least one side opening in each side portion and to the post member and tightening the sutures to or around the post member.

In some embodiments, the post member is one of a plurality of post members mounted on the interior surface of the frame.

In some embodiments, a width of the inner edges of the central opening, in a radial direction, is wider than a remainder of the two side portions.

In another representative embodiment, a method for assembling a commissure attachment assembly to an annular frame of a prosthetic heart valve can include: bending a support member in a radial direction, relative to a central longitudinal axis of the frame, around a central longitudinal axis of the support member, wherein the support member comprises a central opening defined between two side portions of the support member; pairing a first commissure tab of a first leaflet with a second commissure tab of a second leaflet, wherein the first leaflet and the second leaflet are configured to be adjacently arranged within the frame, each leaflet comprising opposing commissure tabs arranged on opposite sides of the leaflet; inserting the paired first commissure tab and second commissure tab into and through the central opening of the support member; and releasing the support member from its bent state so that it reverts back toward a non-deformed state which the support member assumed prior to the bending.

In some embodiments, the bending includes widening a width of the central opening and the releasing includes narrowing the width of the central opening.

In some embodiments, the releasing includes narrowing a width of the central opening so that side edges of the central opening exert a clamping force against portions of the first and second commissure tabs arranged within the central opening.

In some embodiments, the bending includes bending the two side portions of the support member toward one another.

In some embodiments, the bending includes elastically bending the support member into a bent state via an applied force and wherein the releasing includes removing the applied force so that the support member reassumes its non-deformed state. In other embodiments, the bending includes plastically deforming the support member into a bent state and wherein the releasing includes plastically deforming the support member back into its non-deformed state.

In some embodiments, the method can further include folding end portions of the first and second commissure tabs extending through the central opening around a radially outward facing side of the support member and securing the support member to a post member mounted on an interior surface of the frame so that the end portions of the first and second commissure tabs are arranged between the support member and the post member.

In another representative embodiment, a method for assembling a commissure attachment assembly to an annular frame of a prosthetic heart valve can include: pairing a first commissure tab of a first leaflet with a second commissure tab of a second leaflet, wherein the first leaflet and the second leaflet are configured to be adjacently arranged within the frame, each leaflet comprising opposing commissure tabs arranged on opposite sides of the leaflet; inserting the paired first and second commissure tabs into and through a central opening of a support member, causing inner portions of side portions of the support member to bend radially outward, in a same direction as the inserting, wherein the central opening is defined between the two side portions and wherein the inner portions of the side portions are arranged adjacent to the central opening; and, once the paired first and second commissure tabs are arranged within the central opening and are no longer being inserted through the central opening, applying a clamping force against the portions of the first and second commissure tabs arranged within the central opening by the inner portions relaxing and pressing against the portions of the first and second commissure tabs.

In some embodiments, a width of the central opening is defined between side edges of the central opening and wherein the inner portions of the two side portions are arranged adjacent to respective side edges of the side edges.

In some embodiments, during the inserting, the inner portions are bent radially outward to a greater degree than following the inserting, after a radially outward force pushing the first and second commissure tabs through the central opening is removed.

In some embodiments, the method can further include, during the inserting, bending on the inner portions of the side portions of the support member in the same direction as the inserting while remaining, outer portions of the side portions remain relatively unbent by the inserting.

In some embodiments, the method can further include attaching the support member to a post member of the frame, following the inserting and applying the clamping force, and further include continuing to apply the clamping force against the portions of the first and second commissure tabs during and after the attaching.

In yet another representative embodiment, a method for assembling a commissure attachment assembly to an annular frame of a prosthetic heart valve can include: attaching one or more wires to a support member of the commissure attachment assembly, the support member disposed at least partially around a pair of commissure tabs of a pair of leaflets such that the commissure tabs extend through a central opening of the support member, wherein each commissure tab of the pair of commissure tabs is part of a different leaflet of the pair of leaflets, the pair of leaflets adjacently arranged within the frame; positioning the support member against a commissure receiving portion arranged on an inner side of a post member of the frame; and bending and tightening the one or more wires around and against an outer side of the post member to secure the commissure attachment assembly to the post member.

In some embodiments, the post member comprises an actuator component configured to mechanically expand and collapse the frame.

In some embodiments, the bending and tightening the one or more wires around and against the outer side of the actuator component includes pulling free ends of the one or more wires radially outward, relative to a central longitudinal axis of the frame, and away from the outer side of the post member, in order to tighten loops of the one or more wires extending from the support member and around the post member against the outer side of the post member. In some embodiments, the method can further include, following the bending and tightening, twisting the free ends of each of the one or more wires together and bending the twisted free ends toward the outer side of the post member to position the twisted free ends against the outer side of the post member. In some embodiments, the method can further include positioning the twisted free ends within a corresponding channel depressed into a surface of the outer side of the post member in order to retain the twisted free ends therein.

In some embodiments, the method can further include folding end portions of the pair of commissure tabs extending through the central opening around a radially outward facing side of the support member and arranging the end portions of the pair of commissure tabs between the support member and the commissure receiving portion of the support member during the positioning the support member against the commissure receiving portion of the post member.

In another representative embodiment, a prosthetic heart valve can include: an annular frame including a plurality of interconnected strut members, the frame being radially collapsible to a collapsed configuration and radially expandable to an expanded configuration; a plurality of leaflets situated within the frame, each leaflet comprising opposing commissure tabs on opposite sides of the leaflet, each commissure tab being paired with an adjacent commissure tab of an adjacent leaflet to form at least one commissure; and a plurality of post members mounted on an interior surface of the frame, each post member comprising: an inner side facing a central longitudinal axis of the frame and comprising a commissure receiving portion; and an outer side facing the interior surface of the frame; where the at least one commissure comprises a commissure attachment assembly, the commissure attachment assembly comprising: a support member disposed around the paired commissure tabs such that the commissure tabs extend through a central opening of the support member; and at least one wire attached to the support member and extending outward from an outer side of the support member; and where the commissure attachment assembly is secured to a first post member of the plurality of post members via the at least one wire such that the outer side of the support member is positioned against the commissure receiving portion of the first post member and the at least one wire is bent around and tightened against the outer side of the first post member.

In some embodiments, end portions of the commissure tabs are folded around the outer side of the support member and the folded over end portions of the commissure tabs are arranged between the commissure receiving portion of the first post member and the outer side of the support member.

In some embodiments, the support member comprises a plurality of sets of apertures spaced axially apart along the support member, each set including one aperture arranged on either side of the central opening and wherein the at least one wire extends through one set of apertures of the plurality of sets of apertures.

In some embodiments, free ends of the at least one wire are positioned together and arranged within one or more channels depressed into the outer side of the first post member.

In some embodiments, the plurality of interconnected strut members are pivotably coupled to one another by hinges located where the strut members overlap each other, where the hinges are configured to allow the strut members to pivot relative to one another as the frame is expanded or contracted.

In some embodiments, the prosthetic heart valve further includes an inner skirt connected to the frame and cusp edge portions of the leaflets are attached to the inner skirt.

The foregoing and other objects, features, and advantages of the technology will become more apparent from the following detailed description, which proceeds with reference to the accompanying figures.

DETAILED DESCRIPTION

In some aspects, the present disclosure pertains to prosthetic heart valves including leaflet sub-assemblies, referred to herein as "commissure attachment assemblies" for forming commissures, and for aiding in attaching the commissures to the frame of the prosthetic valve. In certain embodiments, the commissure attachment assemblies can comprise support members to which commissure tab portions of the leaflets are secured to form a pre-assembled commissure. The support members, in turn, can be secured to the frame, such as to post members, actuator components, etc., disposed on the interior of the frame. In certain embodiments, the support members can comprise a plurality of openings to which the leaflets can be secured by suturing or other means. The commissure attachment assemblies can be configured for attachment to the frame with the support members arranged radially inward of the leaflets (relative to a central longitudinal axis of the prosthetic heart valve), or with the support members disposed between the leaflets and the frame. In some embodiments, the support members can be configured as exterior panels or cover members of the post members of the frame. Certain configurations of the commissure attachment assemblies can comprise reinforcement members that can secure the leaflets between the support member and the reinforcement member, or which can be configured to clamp the leaflets to the support member. In yet other embodiments, the post members can comprise outwardly-extending retaining members, and the leaflets can be inserted between the retaining members and the main bodies of the post members to form the commissures.

In some embodiments, all or portions of the support members can comprise a flexible material and be configured to bend in a radially outward or inward direction to enable easier extension of the leaflets through the support member and/or to more securely clamp the leaflets together within the support member.

In some embodiments, a commissure attachment assembly can comprise a support member attached to an actuator component of the frame or other frame component of the prosthetic heart valve via one or more flexible attachment members that can extend through the openings of the support member and around the actuator component. In some embodiments, the flexible attachment members can be elastically or plastically deformable wires or polymeric members that are adapted to deform and hold their deformed shape.

Figure 1:
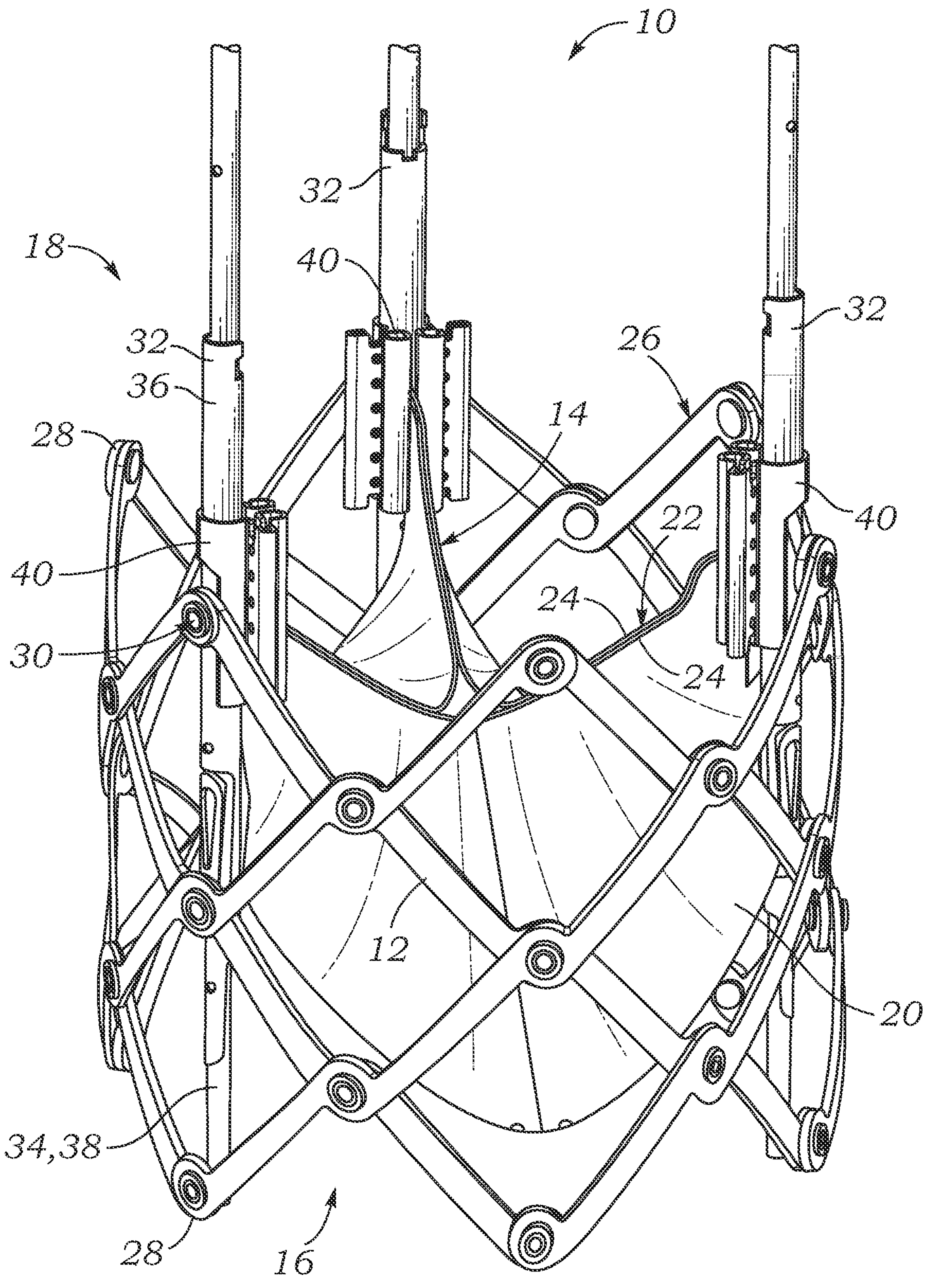
FIG. 1 is a perspective view of a mechanically-expandable prosthetic heart valve, according to one embodiment.

FIG. 1 illustrates a mechanically-expandable prosthetic heart valve 10, according to one embodiment. The prosthetic valve 10 can include an annular stent or frame 12, and a leaflet structure 14 situated within and coupled to the frame 12. The frame 12 can include an inflow end 16 and an outflow end 18. The leaflet structure can comprise a plurality of leaflets 20, such as three leaflets arranged to collapse in a tricuspid arrangement similar to the aortic valve, such that the leaflets form commissures 22 where respective outflow edge portions 24 of the leaflets contact each other. Alternatively, the prosthetic valve can include two leaflets 20 configured to collapse in a bicuspid arrangement similar to the mitral valve, or more than three leaflets, depending upon the particular application.

The frame 12 can include a plurality of interconnected lattice struts 26 arranged in a lattice-type pattern and forming a plurality of apices 28 at the outflow end 18 of the prosthetic valve. The struts 26 can also form similar apices 28 at the inflow end 16 of the prosthetic valve. The lattice struts 26 can be pivotably coupled to one another by hinges 30 located where the struts overlap each other, and also at the apices 28. The hinges 30 can allow the struts 26 to pivot relative to one another as the frame 12 is expanded or contracted, such as during assembly, preparation, or implantation of the prosthetic valve 10. The hinges 30 can comprise rivets or pins that extend through apertures formed in the struts 26 at the locations where the struts overlap each other. Additional details regarding the frame 12 and devices and techniques for radially expanding and collapsing the frame can be found in U.S. Publication No. 2018/0153689, U.S. Patent Application No. 62/928,291, filed Oct. 30, 2019, and U.S. Patent Application No. 62/950,005, filed Dec. 18, 2019, all of which are incorporated herein by reference.

As illustrated in FIG. 1, the frame 12 can comprise a plurality of post members 32. In the illustrated configuration, the post members 32 are configured as actuator components that can also function as release-and-locking units (also referred to as locking assemblies) configured to radially expand and contract the frame. In the illustrated configuration, the frame 12 can comprise three actuator components 32 coupled to the frame 12 at circumferentially spaced locations, although the frame may include more or fewer actuator components depending upon the particular application. Each of the actuator components 32 generally can comprise an inner member 34, such as an inner tubular member, and an outer member 36, such as an outer tubular member concentrically disposed about the inner member 34. The inner members 34 and the outer members 36 can be moveable longitudinally relative to each other in a telescoping manner to radially expand and contract the frame 12, as further described in U.S. Publication No. 2018/0153689, U.S. Patent Application No. 62/928,291, and U.S. Patent Application No. 62/950,005, which are incorporated by reference above.

In the illustrated configuration, the inner members 34 can have distal end portions 38 coupled to the inflow end 16 of the frame 12 (e.g., with a coupling element such as a pin member). In the illustrated embodiment, each of the inner members 34 are coupled to the frame at respective apices 28 at the inflow end 16 of the frame. The outer members 36 can be coupled to apices 28 at the outflow end 18 of the frame 12 at, for example, a mid-portion of the outer member, as shown in FIG. 1, or at a proximal end portion of the outer member, as desired.

The inner member 34 and the outer member 36 can telescope relative to each other between a fully contracted state (corresponding to a fully radially expanded state of the prosthetic valve) and a fully extended state (corresponding to a fully radially compressed state of the prosthetic valve). In the fully extended state, the inner member 34 is fully extended from the outer member 36. In this manner, the actuator components 32 allow the prosthetic valve to be fully expanded or partially expanded to different diameters and retain the prosthetic valve in the partially or fully expanded state.

In alternative embodiments, the actuator components 32 can be screw actuators configured to radially expand and collapse the frame 12 by rotation of one of the components of the actuators. For example, the inner members 34 can be configured as screws having external threads that engage internal threads of corresponding outer components. Further details regarding screw actuators that can be used in combination with any of the frame embodiments described herein are disclosed in U.S. Publication No. 2018/0153689.

Referring to FIG. 1, the prosthetic valve 10 can include a plurality of commissure support elements configured as commissure clasps or clamps 40. In the illustrated configuration, the prosthetic valve includes a commissure clamp 40 positioned at each commissure 22 and configured to grip the leaflets 20 of the commissure at a location spaced radially inwardly of the frame 12. The commissure clamps 40 can be disposed around the outer members 36 of the actuator components 32, and can support the leaflets of each commissure 22 within the frame by holding the outer portions of the leaflets together as the outflow edge portions 24 coapt and move away from each other during valve operation. Further details regarding various embodiments of commissure clamps including the commissure clamps 40 are described in U.S. Publication No. 2018/0325665, which is incorporated herein by reference.

Figure 2A:
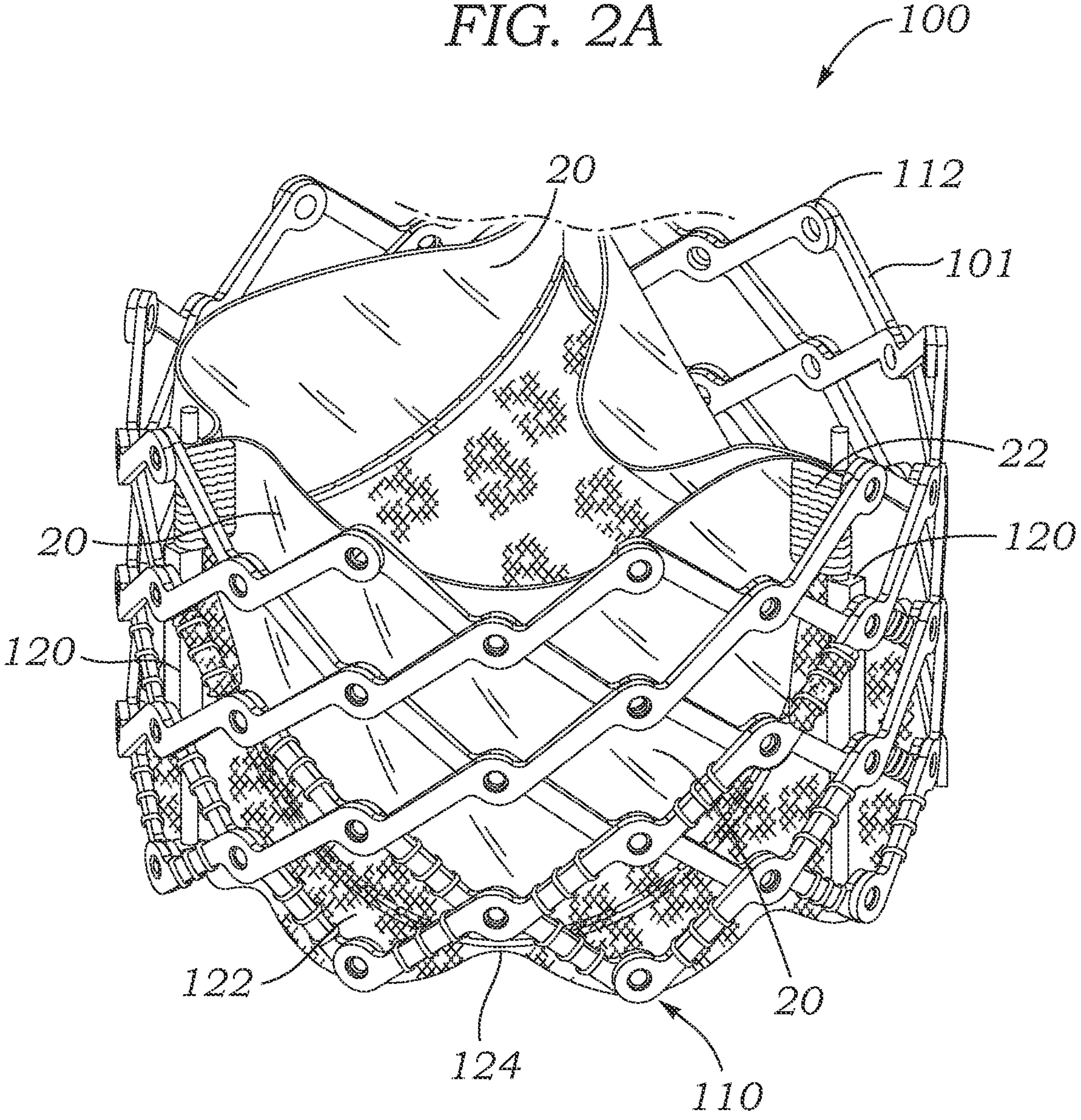
FIG. 2A is a perspective view of another embodiment of a mechanically-expandable prosthetic heart valve.
Figure 2B:
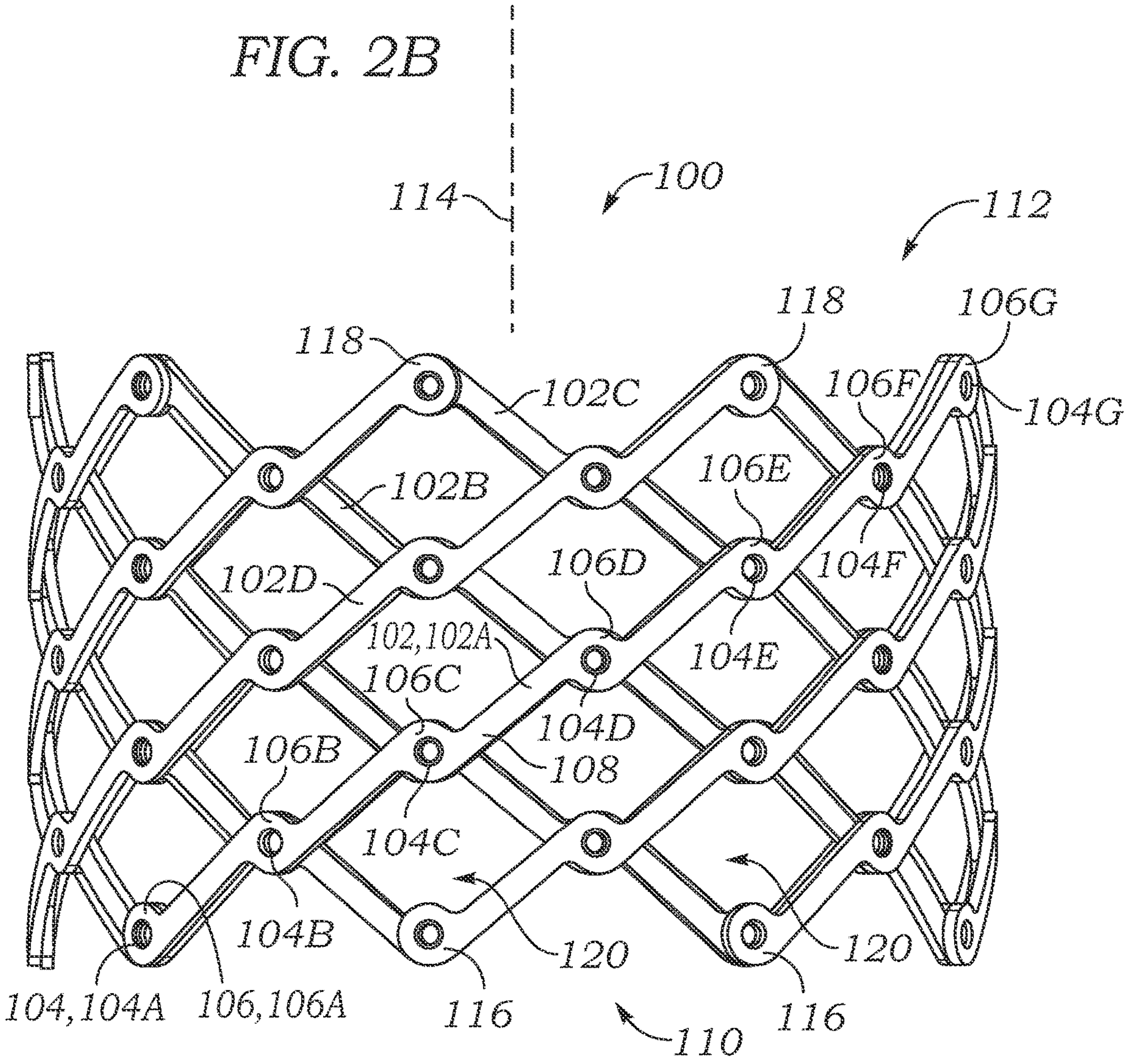
FIG. 2B is a side elevation view of the bare frame of the prosthetic heart valve of FIG. 2A.

FIGS. 2A and 2B illustrate another embodiment of a mechanically-expandable prosthetic heart valve 100 comprising a frame 101. FIG. 2B shows the bare frame 101 with all other components of the prosthetic valve removed for purposes of illustration. The frame 101 can be similar to the frame 10, except that the struts 102 include seven apertures 104 spaced apart along the length of each strut for forming hinges similar to the hinges 30. For example, each strut 102 can include a plurality of round, curved, or circular portions 106 connected by straight portions or segments 108. Each successive segment 108 can be parallel to, but circumferentially offset from, the preceding segment 108, as described in U.S. Publication No. 2018/0153689. Each round portion 106 can define an aperture 104. Thus, taking the strut member 102A by way of example, the round portion 106A at the inflow end 110 of the frame 100 can define an aperture 104A. Moving along the strut 102A in the direction of the outflow end 112, the portion 106B can define an aperture 104B, the portion 106C can define an aperture 104C, the portion 106D can define an aperture 104D, the portion 106E can define an aperture 104E, the portion 106F can define an aperture 104F, and the portion 106G can define an aperture 104G at the outflow end 112. The apertures, and the hinges formed therewith, can function substantially as described above to allow the frame to be radially collapsed for delivery and radially expanded at the treatment site.

In the illustrated configuration, the struts 102 can be arranged in two sets, with the first set being on the inside of the frame 101, offset circumferentially from each other, and angled such that the struts extend helically around the central axis 114 of the frame. In the embodiment of FIG. 2B, struts 102B and 102C are part of the first or inner set of struts. The second set of struts 102 can be disposed radially outward of the first set of struts. The second set of struts can be angled such that the apertures 104 align with the apertures 104 of the inner set of struts, and can be oriented with the opposite helicity as the first set of struts. In the embodiment illustrated in FIG. 2B, the struts 102A and 102D are part of the second or outer set of struts. The inner and outer sets of struts 102 can form inflow apices 116 of the frame where the respective round portions 106 align, and can form outflow apices 118 where the respective round portions at the opposite ends of the struts align. In the expanded configuration, the struts 102 of the inner and outer sets of struts can also define a plurality of diamond-shaped cells or openings.

As shown in FIG. 2A, the prosthetic valve 100 comprises a plurality of leaflets 20 forming commissures 22 that are mounted to actuators 120. The cusp edge portion (the inflow edge portion) of each leaflet 20 can be connected to an inner skirt 122 by one or more sutures along a suture line 124. The inner skirt 122 can be a circumferential inner skirt that spans an entire circumference of the inner surface of the frame 101. The inner skirt 122 can function as a sealing member to prevent or decrease perivalvular leakage (e.g., when the valve is placed at the implantation site) and as an attachment surface to anchor the cusp edge portions of the leaflets 20 to the frame 101. The prosthetic valve 100 can also include an outer skirt (not shown) that around and covering a portion of the outer surface of the frame 101. The outer skirt can function as a sealing member by sealing against the tissue of the native valve annulus and helping to reduce paravalvular leakage past the prosthetic valve 100.

The inner and outer skirts can be formed from any of various suitable biocompatible materials, including any of various synthetic materials (e.g., PET fabric) or natural tissue (e.g., pericardial tissue). The inner and outer skirts can be mounted to the frame using sutures, an adhesive, welding, and/or other means for attaching the skirts to the frame. Further details regarding the inner and outer skirts and techniques for assembling the leaflets to the inner skirt and assembling the skirts on the frame are disclosed in U.S. Provisional Application No. 62/854,702, U.S. Provisional Application No. 62/797,837, U.S. Provisional Application No. 62/823,905 and U.S. Patent Application Publication No. 2019/0192296, each of which is incorporated herein by reference.

Additional mechanically-expandable frame and commissure assembly embodiments are described in U.S. application Ser. No. 16/208,263, published as U.S. Publication No. US2019/0105153, which is incorporated herein by reference.

Figure 3:
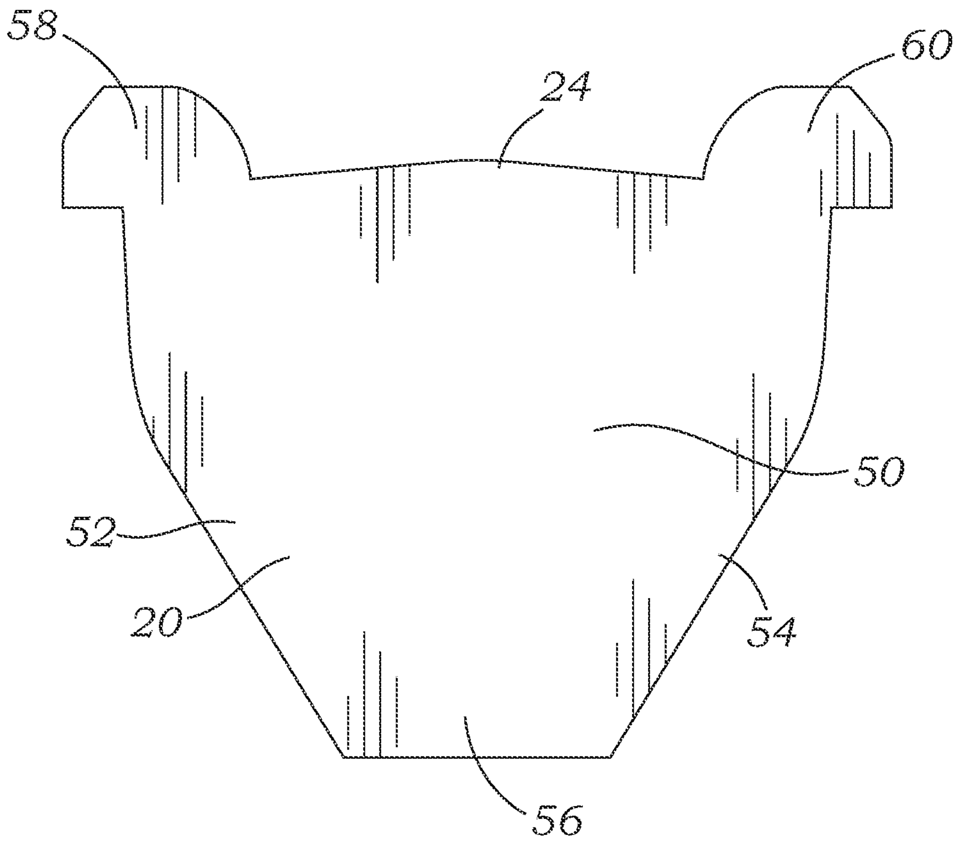
FIG. 3 is a plan view of a prosthetic valve leaflet, according to one embodiment.

FIG. 3 illustrates a representative leaflet 20 laid flat for purposes of illustration. The leaflet 20 can comprise a main body 50 with side edge portions 52 and 54. The edge portions 52 and 54 can be angled such that the overall shape of the leaflet is tapered from the outflow edge portion 24 to an inflow edge portion 56 that is shorter than the outflow edge portion 24. The leaflet 20 can comprise commissure tab portions 58 and 60 extending from opposite sides of the main body 50. The commissure tab portions 58 and 60 can be configured for engagement with corresponding tab portions of adjacent leaflets to form commissures, and for attachment to the frame.

Figure 4:
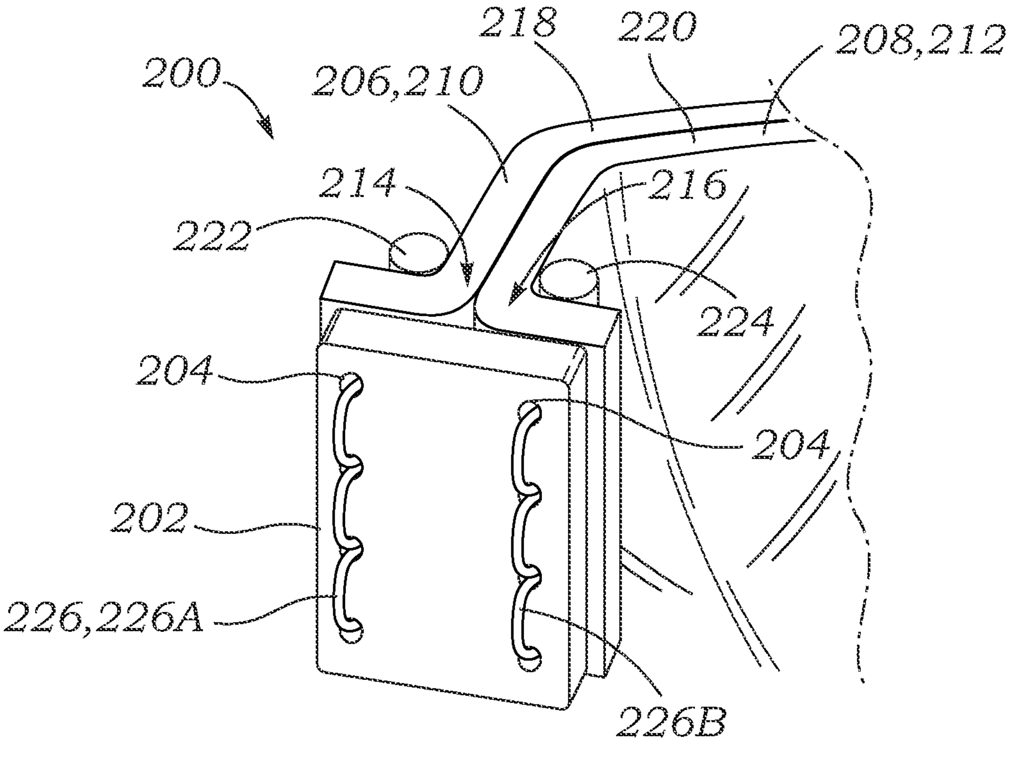
FIG. 4 is a perspective view of an embodiment of a commissure attachment assembly including a support member and a plurality of reinforcement members.
Figure 5:
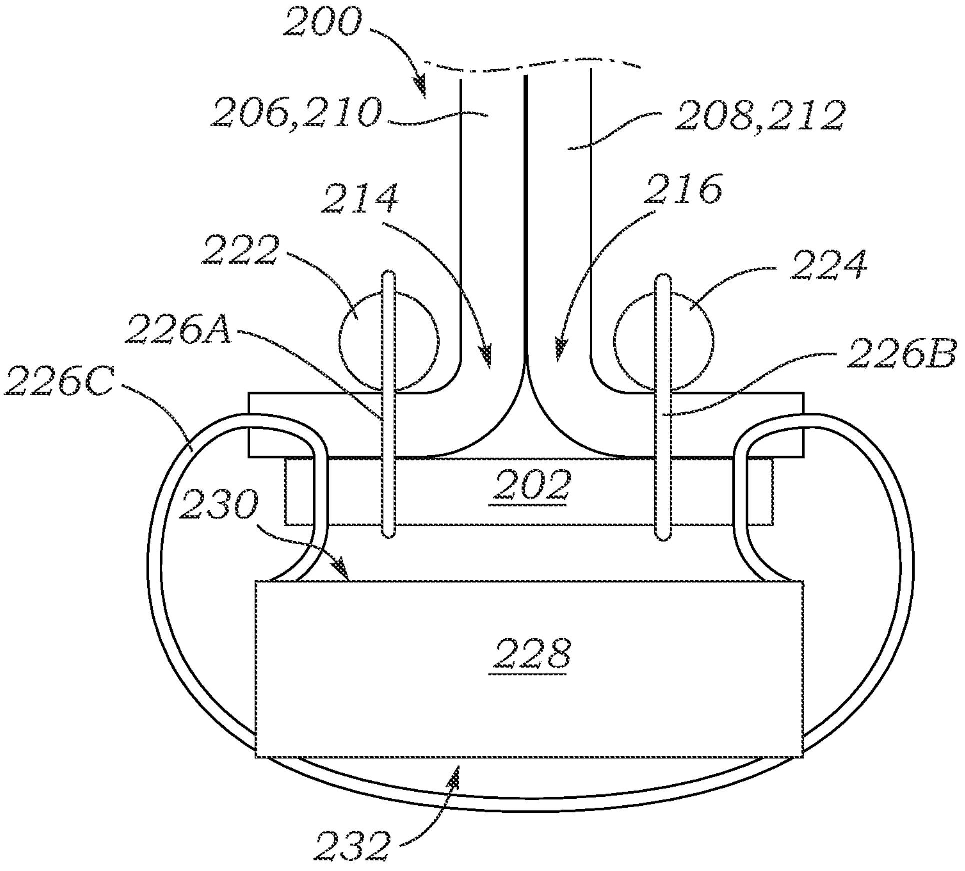
FIG. 5 is a top plan view of the commissure attachment assembly of FIG. 4 coupled to an actuator component of a prosthetic heart valve.

FIGS. 4 and 5 illustrate a representative example of a commissure attachment assembly 200 that can be used in combination with any of the frames described herein to form a commissure, according to one embodiment. The commissure attachment assembly 200 can be configured as a subassembly that holds two paired leaflets together prior to mounting the leaflets in the valve frame. The commissure attachment assembly 200 can comprise a support member 202. The support member 202 may be configured as a rectangular plate, card, or button, as in the illustrated embodiment, or as a round member such as a disc.

Referring to FIG. 4, the support member 202 can comprise a plurality of openings 204 arranged in two rows (e.g., with the central axes of the openings arranged along a straight line). The rows of openings 204 can be spaced-apart from each other, and can extend in the direction of the longitudinal axis of the frame. Two leaflets 206 and 208 are shown with their respective commissure tab portions 210 and 212 contacting a surface of the support member 202. More particularly, the leaflet 206 is folded to form a fold 214, and the leaflet 208 is folded to form a fold 216. The outflow edges 218 and 220 of the leaflets 206 and 208 are in contact with each other radially inwardly of the folds 214 and 216. A reinforcement member 222 can be positioned in the fold 214, and a reinforcement member 224 can be positioned in the fold 216.

The assembly can be held together by securing means such as sutures 226. For example, in the illustrated embodiment the commissure tab portion 210 of the leaflet 206 can be sutured to the support member 202 with sutures 226A passing through the reinforcement member 222, the commissure tab 210, and sequentially through the openings 204 on the left side of FIG. 4. In this manner, the commissure tab portion 210 can be sandwiched between the support member 202 and the reinforcement member 222. The commissure tab portion 212 of the leaflet 208 can be secured between the support member 202 and the reinforcement member 224 in a similar manner using sutures 226B. In certain embodiments, the reinforcement members 222 can reduce stresses on the leaflets associated with valve operation.

With reference to FIG. 5, the commissure attachment assembly 200 can be mounted within a prosthetic heart valve frame by securing the assembly to a commissure support member of the frame, such as an actuator component 228. The actuator component 228 can be, for example, the outer member of an actuator of a mechanically-expandable prosthetic heart valve, similar to the outer members 36 of the actuator components 32 of FIG. 1. In the illustrated embodiment, the actuator component 228 can have a rectangular cross-section, although in other embodiments the actuator component may have a round cross-section, or a cross-section having any other selected shape. In other embodiments, the commissure support member can be a separate component from the actuator that is mounted to an inner surface of the frame. In still other embodiments, the commissure support member can be an integral component of the frame, as one of the struts of the frame.

In the illustrated embodiment, the support member 202 can be positioned against the radially-inward surface 230 of the actuator component 228, and the commissure attachment assembly 200 can be secured to the actuator component 228 by sutures 226C. The sutures 226C can extend through the openings 204 in the support member 202, through the leaflets 206 and 208, and around the radially-outward surface 232 of the actuator component 228. The commissure support assembly can also be secured to the actuator component 228 in other ways, such as by fixation means including one or more fasteners, threads, yarns, or combinations thereof. In other embodiments, the radially-inward surface 230 of the actuator component 228 can comprise openings through which the sutures 226C can be inserted to secure the commissure support assembly to the actuator component. Similar pre-assembled commissure attachment assemblies can be secured to the actuator components 228 or other posts in the frame to form the specified number of commissures. In certain embodiments, the support member 202 can serve as a jig to aid in aligning the leaflets to optimize performance and stability.

In certain embodiments, the support member 202 can comprise a relatively rigid material, such as any of various biocompatible metals such as nitinol, stainless steel, cobalt-chromium, etc., or polymeric materials. Exemplary polymeric materials can include ultra-high-molecular-weight polyethylene (UHMWPE) (e.g., Dyneema®), high-molecular-weight polyethylene (HMWPE), or polyether ether ketone (PEEK), polytetrafluoroethylene (PTFE), expanded polytetrafluoroethylene (ePTFE), ethylene tetrafluoroethylene (ETFE), nylon, polyethylene, polyether block amide (e.g., Pebax), and/or combinations of any of the above. In some embodiments, the support member can comprise multiple layers such as, for example, an inner metal layer and one or more polymeric outer layers. In other embodiments, the support member 202 can comprise a flexible material, such as a woven or non-woven fabric.

In some embodiments, the reinforcement members 222 and 224 can comprise a strong yet penetrable material such as relatively thick suture (a monofilament suture or a multifilament suture, such as a braided suture (e.g., an Ethibond suture as one example)), yarn, fabric (may be folded one or more times to increase its thickness), cord, a polymeric rod, etc., to facilitate suturing. Commissure attachment assemblies such as the assembly 200 can be used to attach adjacent leaflets together at each commissure of a prosthetic heart valve, and to attach the leaflets to the actuator components of the frame. Pre-assembled commissure assemblies like the assembly 200 can significantly reduce the time required to form commissures and secure leaflets within the frame, and can improve the accuracy of leaflet alignment.

Figure 6:
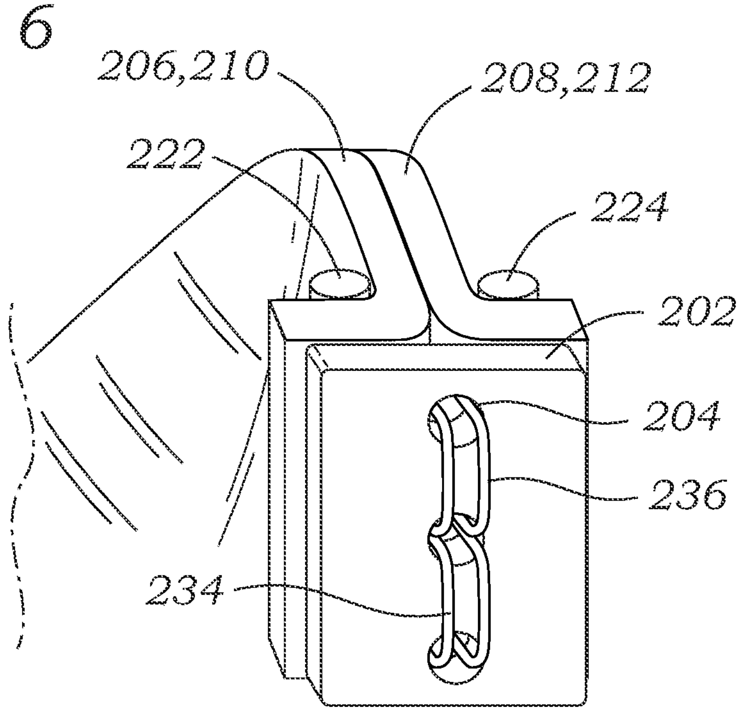
FIG. 6 is a perspective view of another embodiment of a commissure attachment assembly in which the support member comprises a central row of openings.
Figure 7:
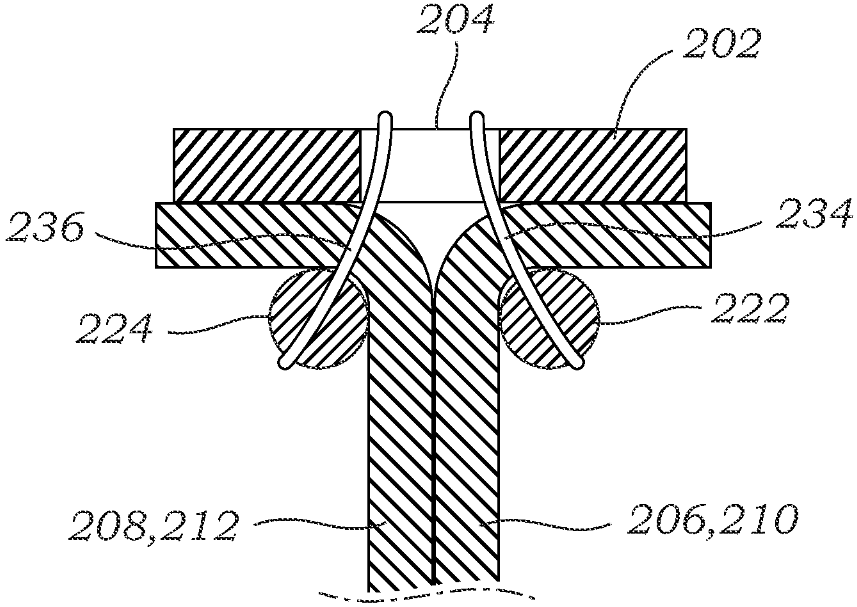
FIG. 7 is a cross-sectional top plan view of the commissure attachment assembly of FIG. 6.

FIGS. 6 and 7 illustrate an alternative embodiment of the commissure attachment assembly 200 in which the openings 204 are arranged in a row extending down the center of the support member 202. One suture or set of sutures 234 can extend between the reinforcement member 222, through the commissure tab portion 210 of the leaflet 206, and through the openings 204 of the support member. Another suture or set of sutures 236 can extend between the reinforcement member 224, through the commissure tab portion 212 of the leaflet 208, and through the openings 204. In other words, with reference to FIG. 7, the stitching lines formed by the sutures 234 and 236 can extend at an angle to each other, and can meet at the openings 204. This can help draw the leaflets 206 and 208 together to facilitate coaptation, and can allow the width of the support member to be reduced.

Figure 8:
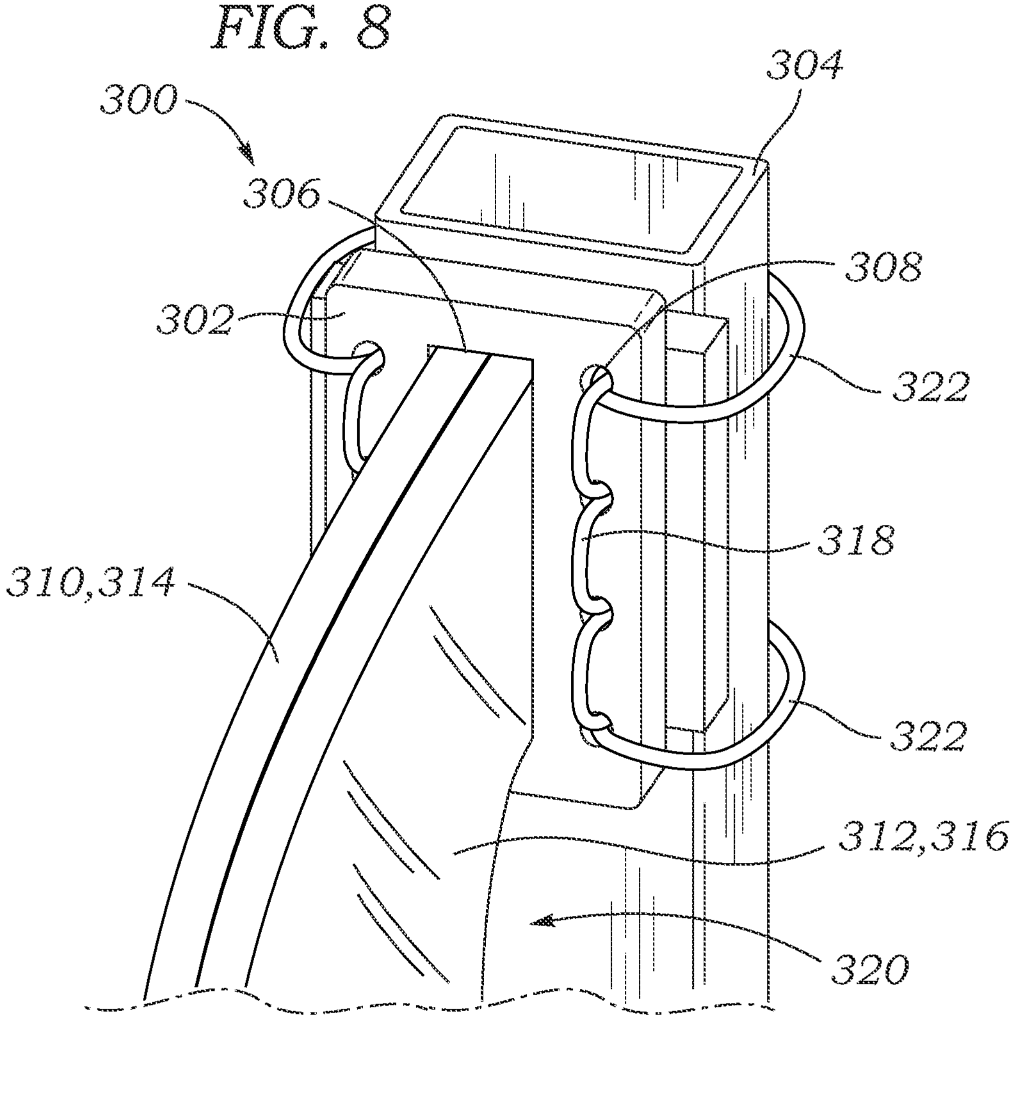
FIG. 8 is a perspective view of another embodiment of a commissure attachment assembly in which the leaflets extend through an opening in the support member.
Figure 9:
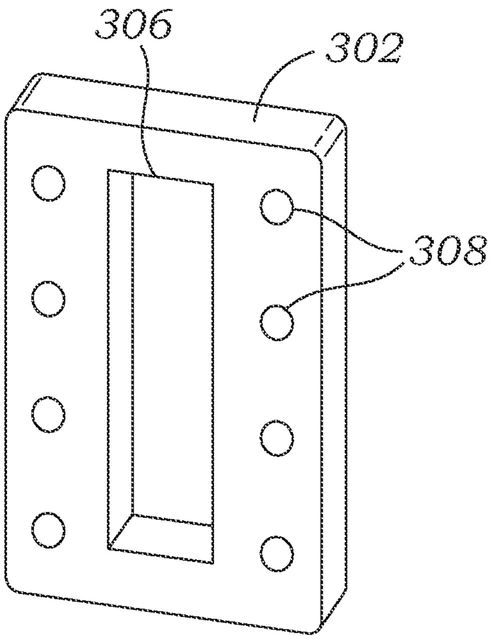
FIG. 9 is a perspective view of the support member of FIG. 8.
Figure 20:
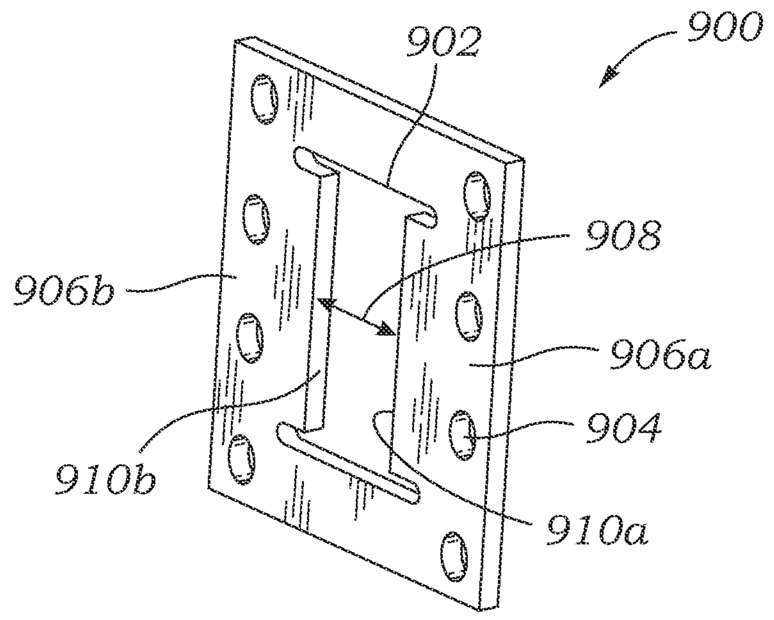
FIG. 20 is a perspective view of another embodiment of a support member for a commissure attachment assembly having an I-shaped central opening.

FIG. 8 illustrates another embodiment of a commissure attachment assembly 300 in which the leaflets are positioned between a support member 302 and a commissure support post 304 of the frame, such as an actuator component. FIG. 9 illustrates the support member 302 in greater detail. The support member 302 can be configured as a rectangular plate, card, or button, similar to the support member 202 of FIG. 4. The support member 302 can define a central opening 306 extending along the long axis of the support member. In the illustrated embodiment, the opening 306 is rectangular, although the opening 306 may have any selected shape. For example, as shown in FIG. 20 (described further below) the central opening may have an I-shape. Rows of openings 308 can extend axially on either side of the opening 306.

Referring again to FIG. 8, the commissure tab portions 310 and 312 of the leaflets 314 and 316, respectively, can be inserted through the opening 306 in the support member. The commissure tab portion 310 can be folded around the support member 302 to the left in FIG. 8, and the commissure tab portion 312 can be folded around the support member to the right. The commissure tabs 310 and 312 can be secured to the support member 302 by sutures 318 extending sequentially through the rows of openings 308. The commissure attachment assembly 300 can be positioned with the leaflets against the radially-inward surface 320 of the actuator component 304, and with the support member facing radially inwardly toward the central axis of the frame. The commissure support assembly can be secured to the actuator component 304 by sutures 322 extending from selected openings 308 (e.g., the top and bottom openings 308) around the actuator component 304.

Figure 10:
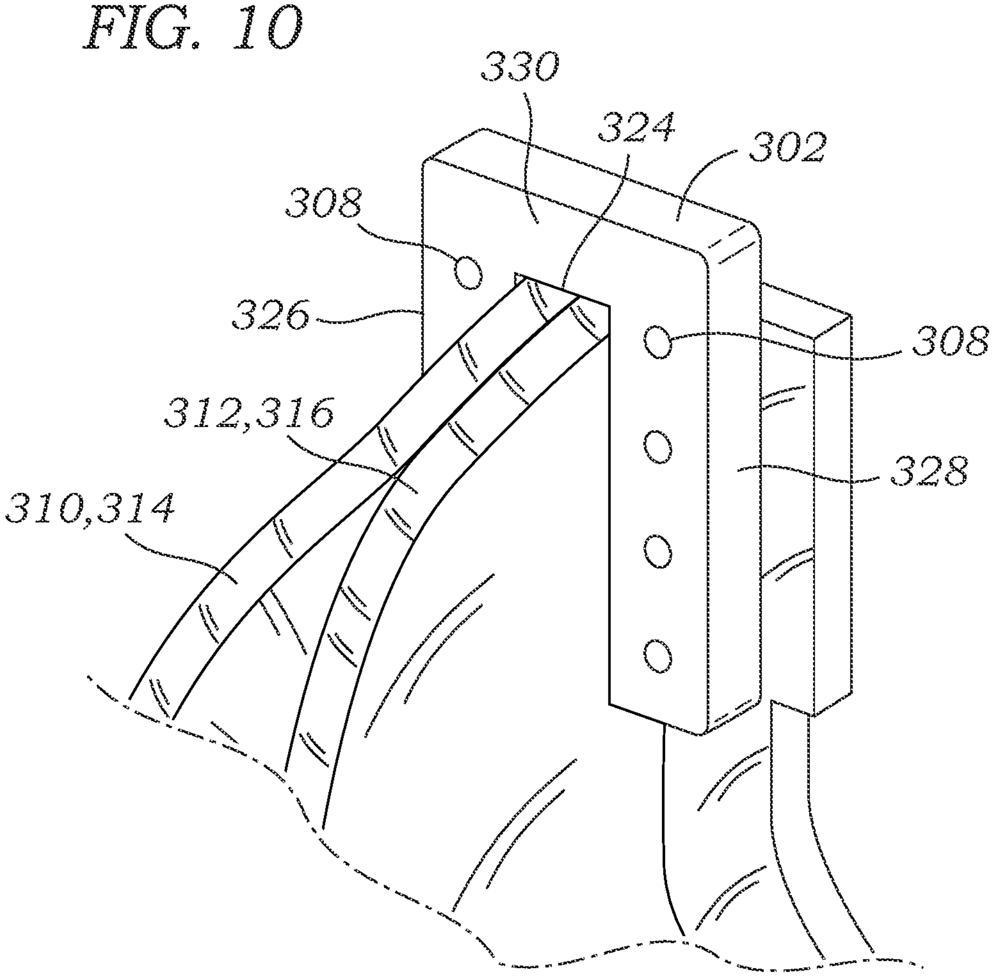
FIG. 10 is a perspective view of another embodiment of a commissure attachment assembly in which the support member comprises a U-shaped member.

FIG. 10 illustrates a commissure attachment assembly incorporating an alternative embodiment of the support member 302 in which the central opening is configured as a slot 324 such that the support member is U-shaped. More particularly, the U-shaped support member 302 of FIG. 10 can comprise a first side portion 326, a second side portion 328, and an upper portion or cross-member portion 330 extending between the side portions 326 and 328. One row of openings 308 can be defined along the side portion 326, and another row of openings 308 can be defined along the side portion 328. The leaflets 314 and 316 can be received in the slot 324. The commissure tab portion 310 can be folded around the side portion 326 and sutured (not shown) to the support member through the openings 308 of the side portion 326. Similarly, the commissure tab portion 312 can be folded around the side portion 328 and sutured to the support member through the openings 308 of the side portion 328. In certain embodiments, the U-shaped support member 302 can improve the durability of the leaflets by reducing the need for thin or narrow pieces of leaflet material to be inserted through the support member 302.

Figure 11:
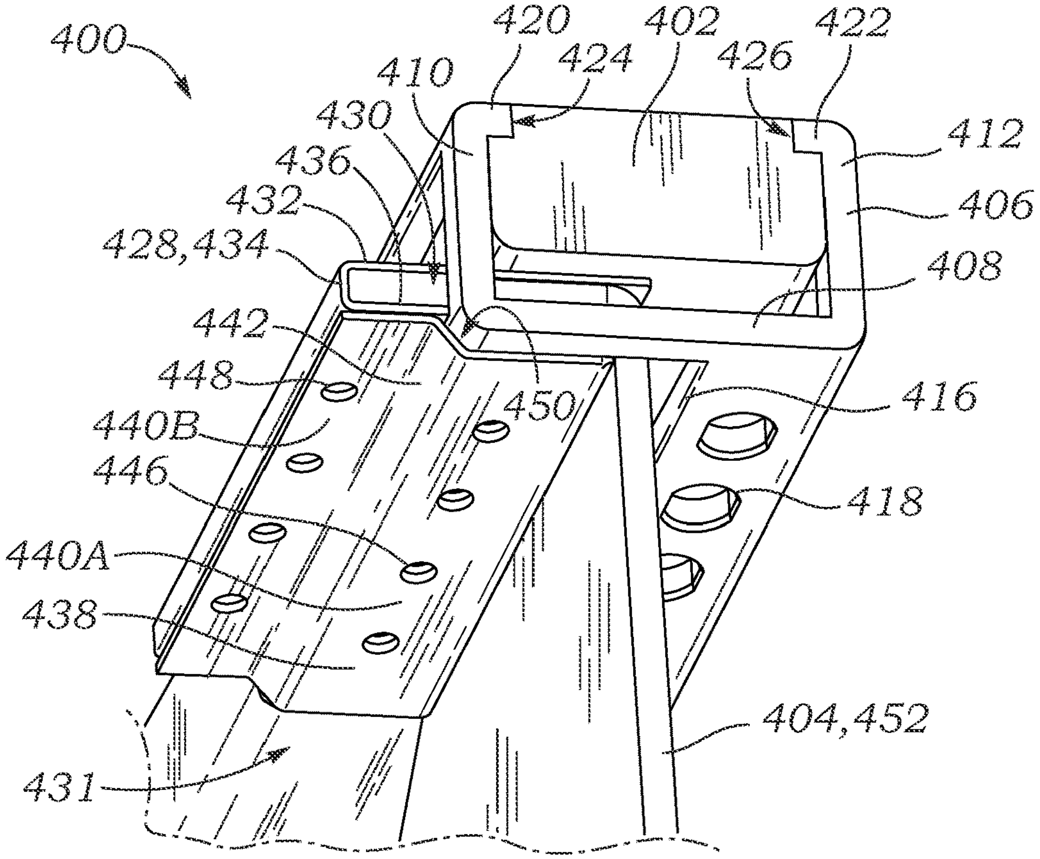
FIG. 11 is a perspective view of another embodiment of a commissure attachment assembly including a support member and reinforcement members configured to clamp the leaflets to the support member.

FIG. 11 illustrates another embodiment of a commissure attachment assembly 400 assembled onto a commissure support post 402 of the frame, such as an actuator component. In FIG. 11, only one leaflet 404 is shown secured to the attachment assembly for purposes of illustration. The commissure attachment assembly 400 can comprise a support member 406. The support member 406 can comprise a first or main portion 408, and second and third portions 410 and 412 (also referred to as "side portions") extending from opposite sides of the main portion 408 such that the support member 406 comprises a generally U-shaped cross-section in the manner of a U-channel member. The main portion 408 can comprise a central rectangular opening 416 extending axially along the main portion. The main portion 408 can further comprise two rows of openings 418 arranged on either side of the opening 416 (only the row of openings 418 on the right of the support member 406 is visible in FIG. 11). The side portions 410 and 412 can comprise respective lip portions 420 and 422. The lip portions 420 and 422 can be configured to engage corresponding grooves or recesses 424 and 426 defined in the rear surface of the post 402, as further described below. The side portions 410 and 412 can further be configured such that the main portion 408 is offset outwardly (e.g., radially inwardly with respect to the valve axis) from the actuator component 402 to provide space to receive the leaflet 404. The side portions 410 and 412 can also define openings to allow the commissure tabs of the leaflets and other components of the commissure attachment assembly to extend through.

The commissure attachment assembly can further comprise a plurality of reinforcement members 428, only one of which is shown in FIG. 11. The reinforcement member 428 can be folded or curved to form a plurality of channels or recesses. More particularly, the reinforcement member 428 can comprise a first portion 432 extending parallel to an inward-facing surface 431 of the actuator member 402 (e.g., circumferentially with respect to the frame). The reinforcement member 428 can further comprise a second portion 434 extending perpendicular to the surface 431 (e.g., radially inwardly), and a third portion 436 extending from the portion 434. The third portion 436 can be parallel to the portion 432 such that the portions 432-436 define a recess 430. The reinforcement member 428 can further comprise a fourth portion (not shown), which can extend from the third portion 436 around the support member 406 through the opening 416. A fifth portion 438 then extends generally circumferentially toward the second portion 434.

In the illustrated embodiment, the fifth portion 438 can comprise a first sub-portion 440A and a second sub-portion 440B separated and radially offset from each other by a ramp or step portion 442 (also referred to as a "third sub-portion"). The surfaces of both sub-portions 440A and 440B can be oriented radially inwardly when the commissure attachment assembly is secured within the valve frame. The first sub-portion 440A can comprise a plurality of openings 446 arranged in a row along the longitudinal axis of the actuator member 402. The location of the openings 446 can correspond with the openings 418 on the left side of the support member 406 in FIG. 11 (which are hidden from view). The second sub-portion 440B can also comprise a longitudinally-arranged row of openings 448.

The third portion 436, the fourth portion (hidden from view in FIG. 11), and the sub-portions 440A and 442 of the fifth portion 438 of the reinforcement member 428 can collectively define a recess or channel 450. The channel 450 can be configured to receive the left-hand portion of the main portion 408 of the support member 406, as shown in FIG. 11.

In certain embodiments, the support member 406 can be made from any of various biocompatible metals or polymeric materials given above. In certain embodiments, the reinforcement member 428 can comprise elastically-deformable or plastically-deformable metals or polymeric materials, or combinations thereof.

In one representative embodiment, the commissure support assembly 400 can be assembled in the following manner. The tab portion 452 of the leaflet 404 can be inserted into the recess 430 of the reinforcement member 428. The first portion 432, the second portion 434, and the third portion 436 of the reinforcement member 428, together with the commissure tab 452, can then be inserted through the opening 416 of the support member 406. In certain embodiments, the fifth portion 438 of the reinforcement member 428 can be elastically or plastically bent outwardly away from the third portion 436 to facilitate passing the leaflet 404 and the portions 342-436 through the opening 416, and locating the left-hand side of the support member 406 in the recess 450. The fifth portion 438 can then be folded closed as necessary so that the second sub-portion 440B contacts the third portion 436 of the reinforcement member 428. In this manner, the reinforcement member 428 can clamp the commissure tab portion 452 to the support member 406.

The leaflet 404 can then be secured to the support member 406 and to the reinforcement member 428 by sutures or other securing means (e.g., fasteners, rivets, etc.) passing through the openings 446 and 448 of the reinforcement member, and through the openings 418 of the support member. A corresponding leaflet can be secured to the other side of the support member 406 using a reinforcement member similar to the reinforcement member 428.

To attach the commissure attachment assembly 400 to the post 402, the support member 406 be slipped over the end of the post such that the lip portions 420 and 422 of the support member are received in the corresponding grooves 424 and 426 of the post. In other embodiments, the side portions 410 and 412 can be flexible such that they can be elastically deformed and placed around the post 402. In yet other embodiments, the support member 406 can be manufactured with the side portions 410 and 412 extending at an angle to each other in an "open" position, and the side portions can be plastically deformed into the "closed" position around the post 402.

Figure 12:
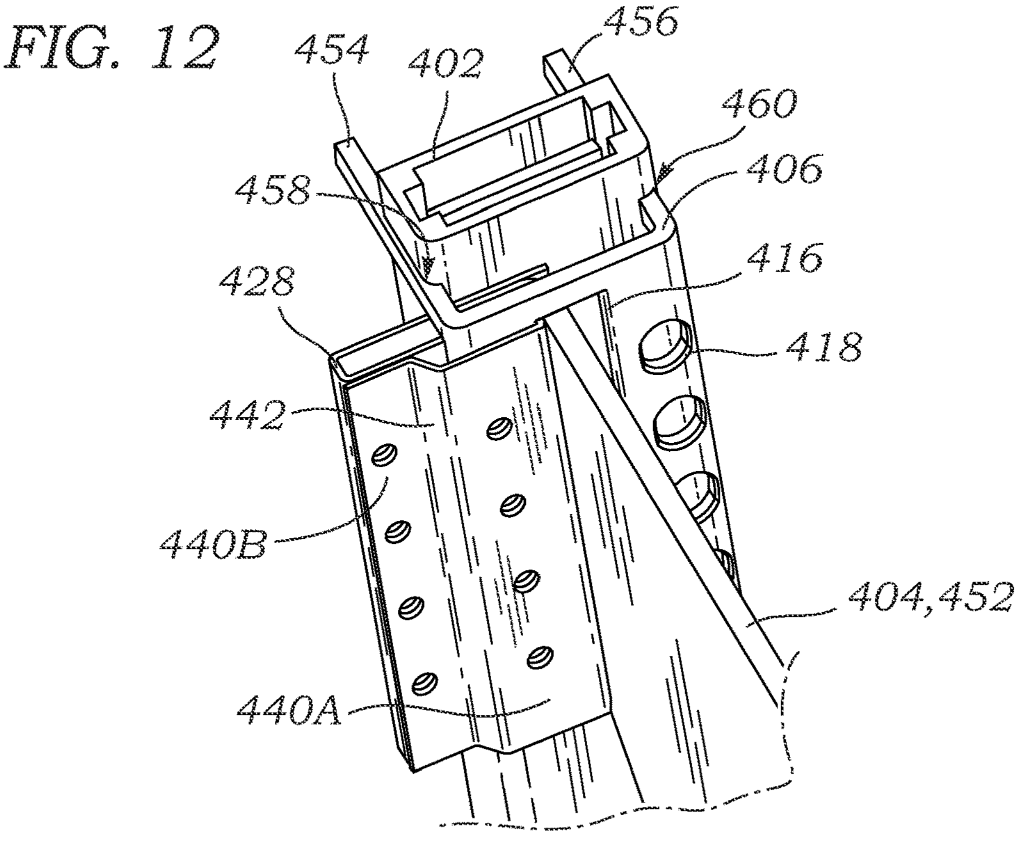
FIG. 12 is a perspective view of another embodiment of the commissure attachment assembly of FIG. 11.

FIG. 12 illustrates another embodiment of the commissure attachment assembly 400 in which the support member 406 comprises tab portions 454 and 456. The post 402 can comprise corresponding grooves or recesses 458 and 460 configured to receive the tabs. In certain embodiments, the tab portions 454 and 456 can be plastically deformed around the actuator member 402 to secure the commissure attachment assembly to the actuator member. In certain embodiments, both the upper or outflow portion and the lower or inflow portion of the support member 406 can comprise tab portions such as tab portions 454 and 456.

In other embodiments, the reinforcement member 428 can comprise a flexible material such as a woven or non-woven fabric that can be folded around and stitched to the commissure tab 452 and the support member 406 in the manner illustrated in FIGS. 11 and 12.

Figure 13:
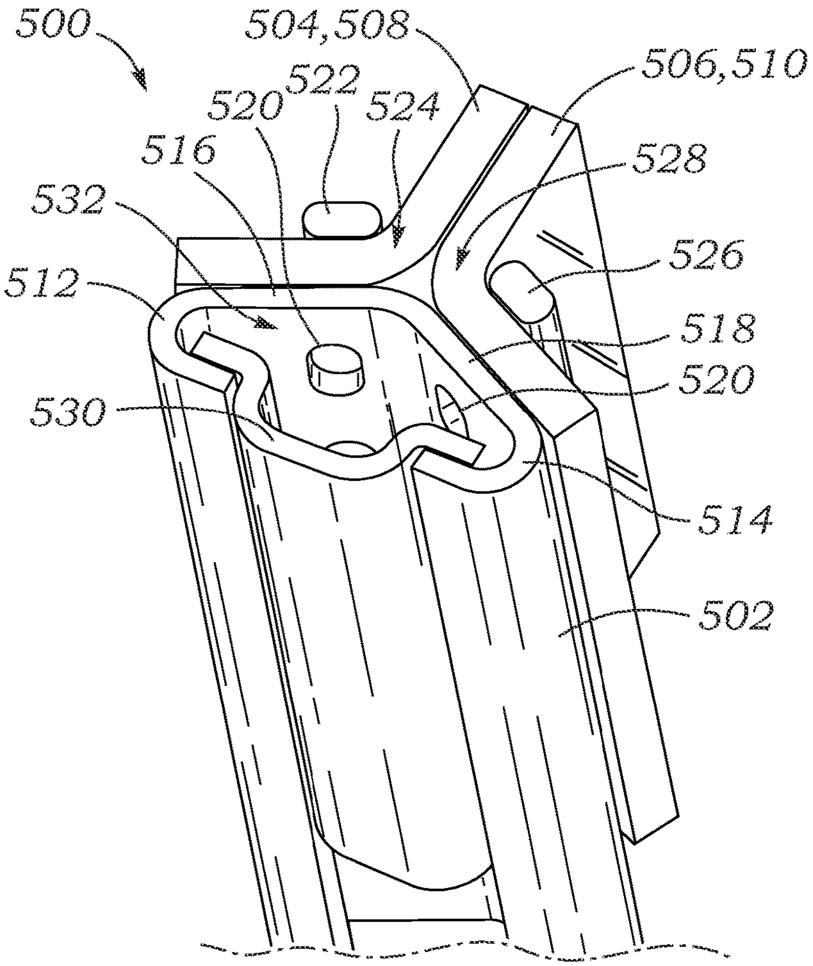
FIG. 13 is a perspective view of another embodiment of a commissure attachment assembly including a support member configured as an outer panel of an actuator member.

FIG. 13 illustrates another embodiment of a commissure attachment assembly 500 including a support member 502 to which the commissure tabs 504 and 506 of two leaflets 508 and 510 are secured. The support member 502 can comprise a curved cross-sectional shape such that the support member defines a channel 532 along its length. For example, in the illustrated embodiment, the support member 502 can comprise a first curved portion or lip portion 512 and a second curved portion or lip portion 514 on the opposite side of the channel 532 from the curved portion 514. The open ends of the curved portions 512 and 514 can face each other. The support member can further comprise first and second attachment portions 516 and 518. The attachment portions 516 and 518 can be angled relative to each other such that they converge in a direction away from the curved portions 512 and 514 (e.g., in a radially-inward direction when the commissure attachment assembly 500 is disposed in a prosthetic valve frame). Each of the attachment portions 516 and 518 can define a longitudinally-extending row of openings 520.

The commissure tab portion 504 can be positioned against the attachment portion 516, and the commissure tab portion 506 can be positioned against the attachment portion 518. The commissure tab portions 504 and 506 can be folded so that the edges of the leaflets 508 and 510 coapt. A reinforcement member 522 can be positioned in a fold 524 of the commissure tab portion 504, and a reinforcement member 526 can be positioned in a fold 528 of the commissure tab 506. The leaflets can be secured to the support member 502 by sutures placed through the reinforcement members 522 and 526, and through the corresponding openings 520 in the attachment portions 516 and 518 of the support member.

In some embodiments, the support member 502 can be configured as a portion of an actuator component of a mechanically-expandable prosthetic valve frame, such as any of the actuator components described herein. For example, in certain embodiments the support member 502 can be configured as a cover or panel that is incorporated into the actuator component and encloses the mechanism of the actuator component in the interior. In such embodiments, a barrier member 530 can be positioned within the channel 532 defined by the support member 502 opposite the attachment portions 516 and 518 to separate the attachment portions (and the associated leaflet securing means) from the internal mechanism of the actuator component. In certain embodiments, the barrier member 530 can comprise a fabric. In other embodiments, the barrier member 530 can comprise metal or a polymeric material. In some embodiments, the commissure tab portions 504 and 506 can be secured to the support member 502, followed by attachment of the support member to the actuator component.

Figure 14:
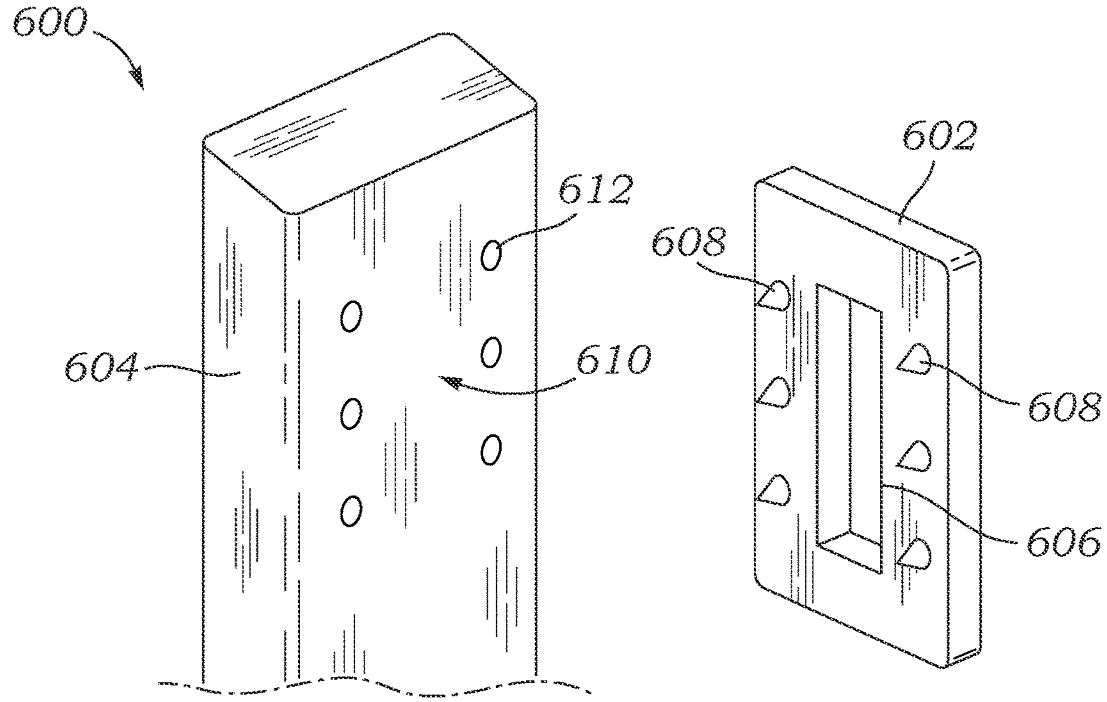
FIG. 14 is a perspective view of another embodiment of a support member and actuator component for use in a commissure attachment assembly in which the support member comprises barbs.
Figure 15:
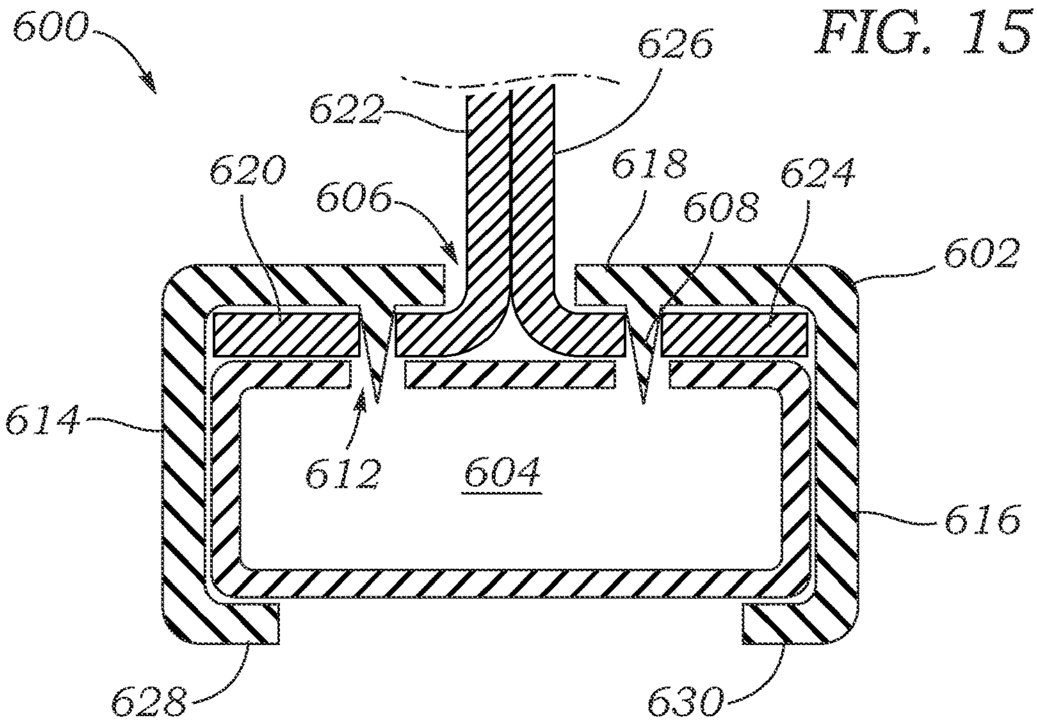
FIG. 15 is a cross-sectional view of a commissure attachment assembly incorporating the support member and actuator component of FIG. 14.

FIGS. 14 and 15 illustrate another embodiment of a commissure attachment assembly 600 in which the leaflets are positioned between a support member 602 and a commissure support post 604, such as an actuator component, similar to the configuration of FIG. 8. The support member 602 can be configured as a rectangular plate, card, or button, similar to the support member 302 of FIG. 8. The support member 602 can define a rectangular central opening 606 extending in the axial direction of the support member, although the opening 606 may have any selected shape. Rows of protrusions configured as sharp barbs or spikes 608 can extend axially on either side of the opening 606. In the illustrated configuration, the support member 602 comprises two rows having three barbs 608 each, although the support member may have any number of rows including any selected number of barbs.

The support member 602 can be configured to be positioned against an inward-facing surface 610 of the post 604. The post 604 can comprise a plurality of openings 612 in the surface 610 configured to receive the barbs 608. Another configuration of the support member 602 is shown in FIG. 15 in which the support member includes two side portions 614 and 616 that extend from a first or main portion 618 such that the support member has a U-shaped cross-section and defines a channel. The main portion 618 can include the opening 606 and the barbs 608.

Referring to FIG. 15, the commissure tab portion 620 of a leaflet 622 can be inserted through the opening 606 and folded such that it is disposed between the main portion 618 of the support member 602 and the post 604. The commissure tab portion 624 of a leaflet 626 can be inserted through the opening 606 and folded in opposite directions. The barbs 608 can pierce the commissure tab portions 620 and 624, and can be at least partially received in the openings 612 of the post, to hold the leaflets in place. Lip portions 628 and 630 of the side portions 614 and 616 can engage the post 604 to hold the support member 602 in place. In certain configurations, the barbs may reduce the need for sutures or other fixation means to hold the leaflets in place.

Figure 16:
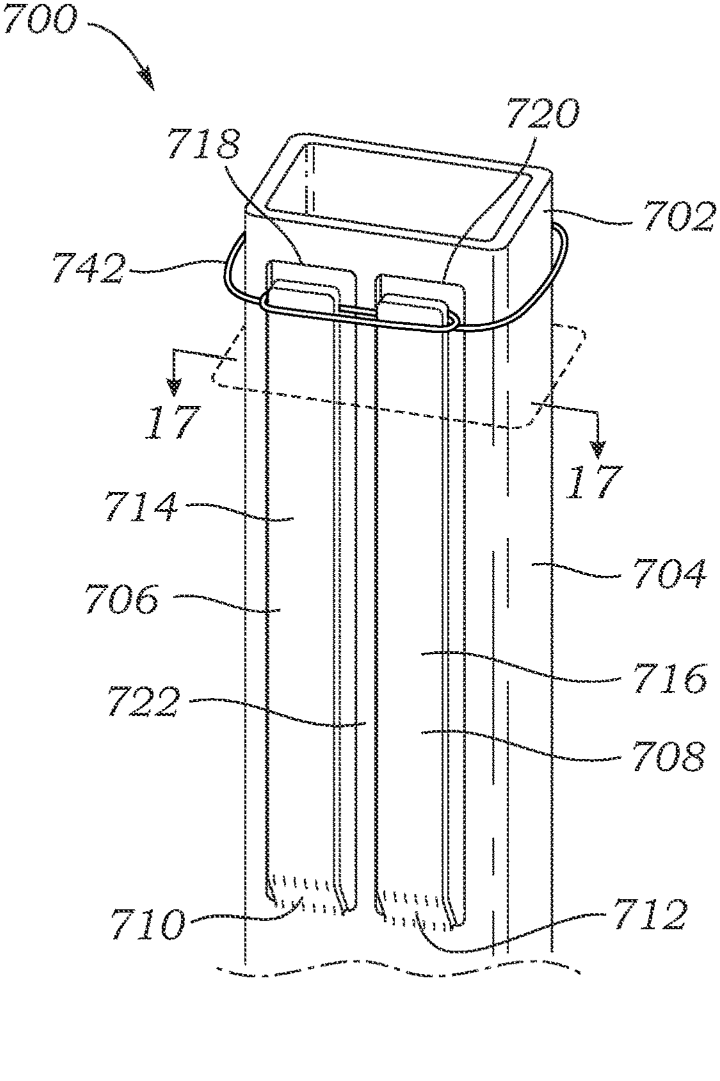
FIG. 16 is a perspective view of another embodiment of an actuator member including retaining members.
Figure 17:
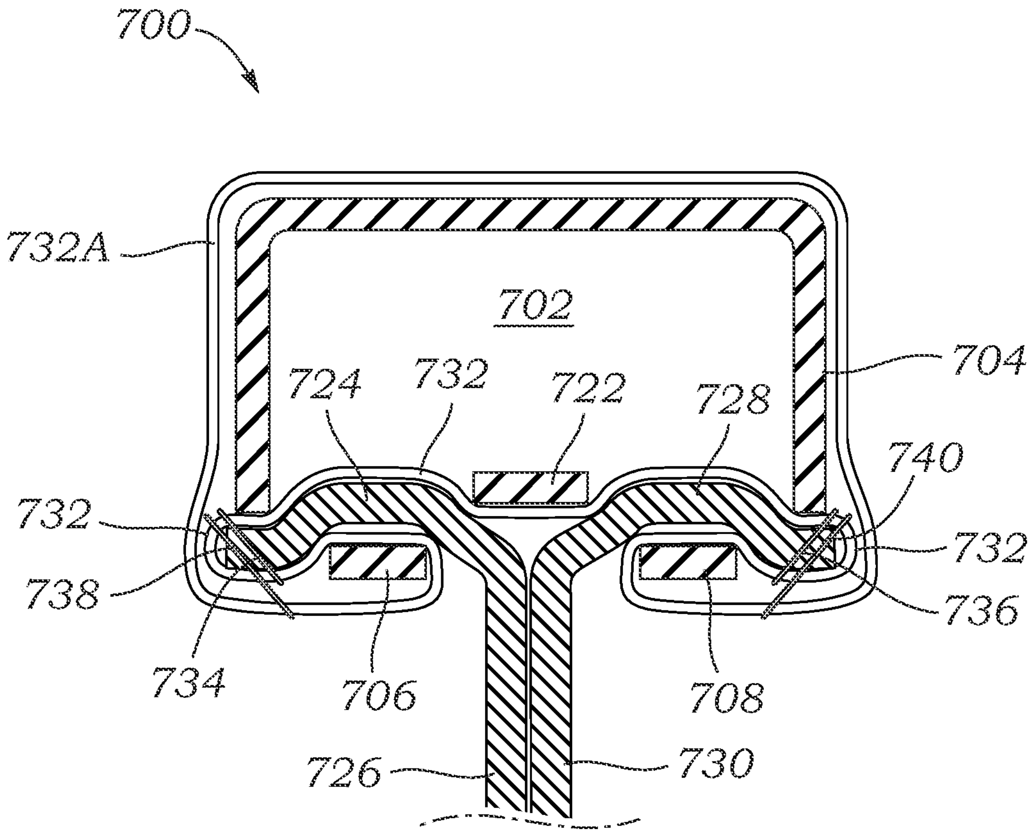
FIG. 17 is a cross-sectional view taken along the plane 17-17 of FIG. 16 illustrating a commissure attachment assembly attached to the actuator component of FIG. 16.
Figure 18:
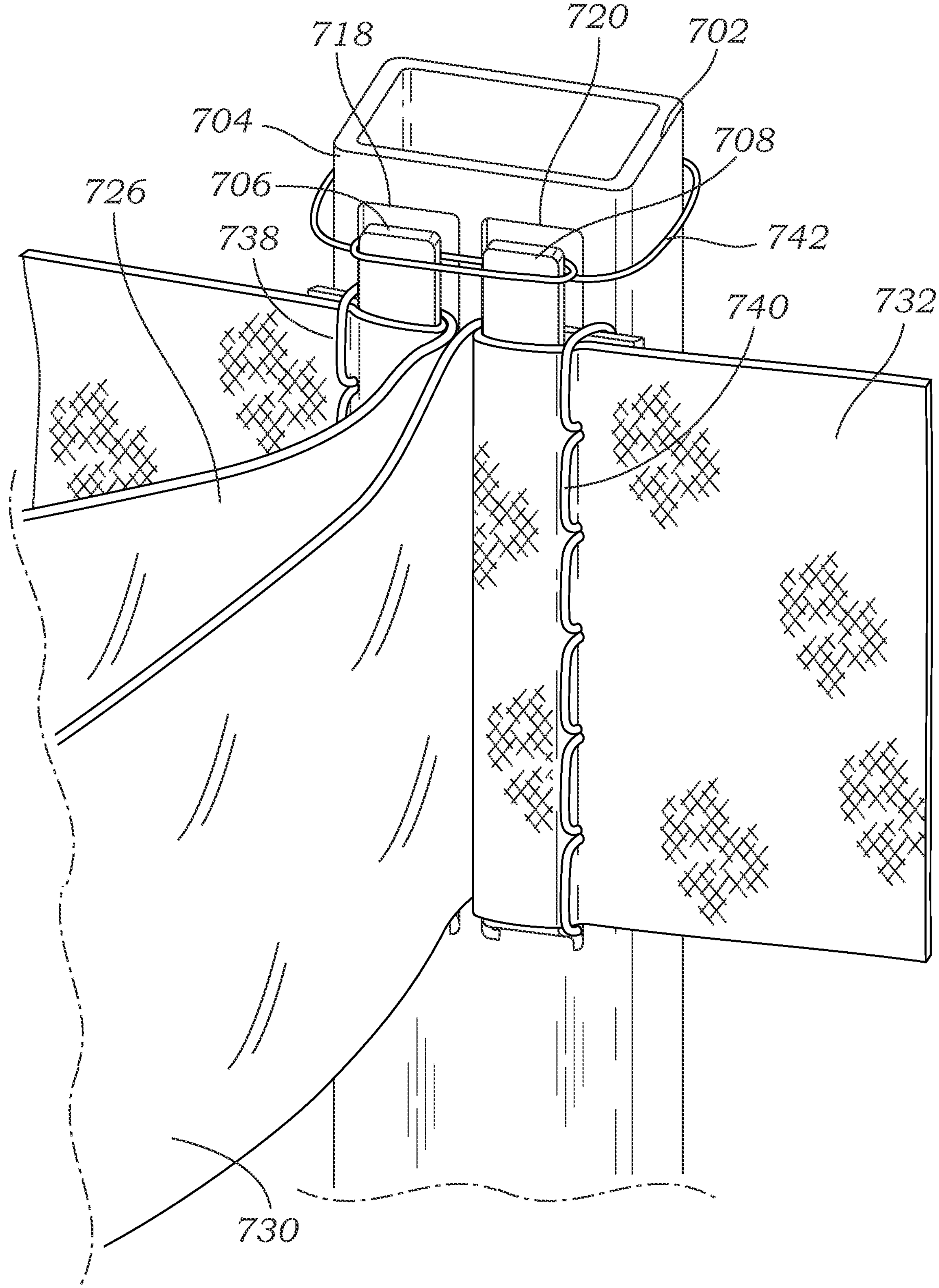
FIG. 18 is a perspective view of the commissure attachment assembly of FIG. 17 during assembly.

FIGS. 16-18 illustrate another embodiment of a commissure attachment assembly 700 in which the leaflets are secured directly to post members in a mechanically-expandable prosthetic heart valve. FIG. 16 illustrates a representative embodiment of a post member configured as an actuator component 702 including a housing 704. The housing 704 may be configured similarly to the outer members 36 of FIG. 1 above. The housing 704 can comprise two retaining members 706 and 708. The retaining members 706 and 708 can include respective base portions 710 and 712 coupled to the housing 704, and respective upper portions configured as prong members or tines 714 and 716. The base portions 710 and 712 can be curved outwardly from the housing 704 (e.g., in the radially-inward direction) such that the prong members 714 and 716 are offset (e.g., radially inwardly) from the housing 704. Respective openings 718 and 720 can be defined in the housing 704 behind the retaining members 706 and 708. A central member or post 722 can extend between the openings 718 and 720. The openings 718 and 720 can be sized and shaped to substantially correspond to the shape of the retaining members 706 and 708, although other configurations are possible.

FIG. 17 illustrates the assembled commissure in a cross-sectional plan view taken through the actuator member 702 along the plane indicated in FIG. 16. The commissure tab portion 724 of a leaflet 726 is shown inserted between the retaining member 706 and the housing 704 such that the retaining member 706 engages the leaflet and retains it against the housing. A commissure tab portion 728 of a second leaflet 730 is shown inserted between the retaining member 708 and the housing 704 in a similar manner. Prior to assembly of the leaflets on the housing, a reinforcement or protective member 732 can be disposed around and sutured to the leaflets 726 and 730. More particularly, the protective member 732 can be wrapped around the commissure tab portion 724 of the leaflet 726, and secured to the leaflet with sutures indicated at 734. The protective member 732 can also be wrapped around the commissure tab portion 728 of the leaflet 730 and secured with sutures 736 such that the two leaflets 726 and 730 are coupled together by the protective member 732, which extends between the two leaflets. When the leaflet 726 is inserted between the retaining member 706 and the housing 704, the protective member 732 can be wrapped around the retaining member 706 such that the retaining member is enclosed within the protective member, and secured to the leaflet again with sutures indicated at 738. The protective member 732 can be wrapped around the retaining member 708 and secured to the leaflet 730 with sutures 740 in a similar manner.

In certain embodiments, the protective member 732 can also extend around the actuator member 702. For example, a portion 732A of the protective member 732 can extend or loop around the actuator member 702 between the sutures 738 and the sutures 740. In other embodiments, the sutures 738 and/or the sutures 740, and/or other sutures, can extend around the actuator member 702 to hold the protective member 732 in place. In certain embodiments, the protective member 732 can comprise a woven or non-woven fabric, or a polymeric or laminate film.

FIG. 18 illustrates the commissure attachment assembly in a partially assembled state after the protective member 732 has been secured to the leaflets with the sutures 738 and 740, and before the protective member 732 has been wrapped around the actuator component 702. With reference to FIG. 18, once the leaflets 726 and 730 have been positioned in the respective retaining members 706 and 708, the retaining members can be retracted toward or into the openings 718 and 720 to grip the leaflets. In the illustrated embodiment, the retaining members 706 and 708 can be urged into the openings 718 and 720 by cord members configured as sutures 742 tied around the ends of the prong members 714 and 716, and extending around the housing 704. The sutures 742 are also indicated in FIG. 16. In certain embodiments, the base portions 710 and 712 of the retaining members 706 and 708 can be configured to bear the axial forces exerted by the leaflets 726 and 728 during venticular diastole.

Figure 19:
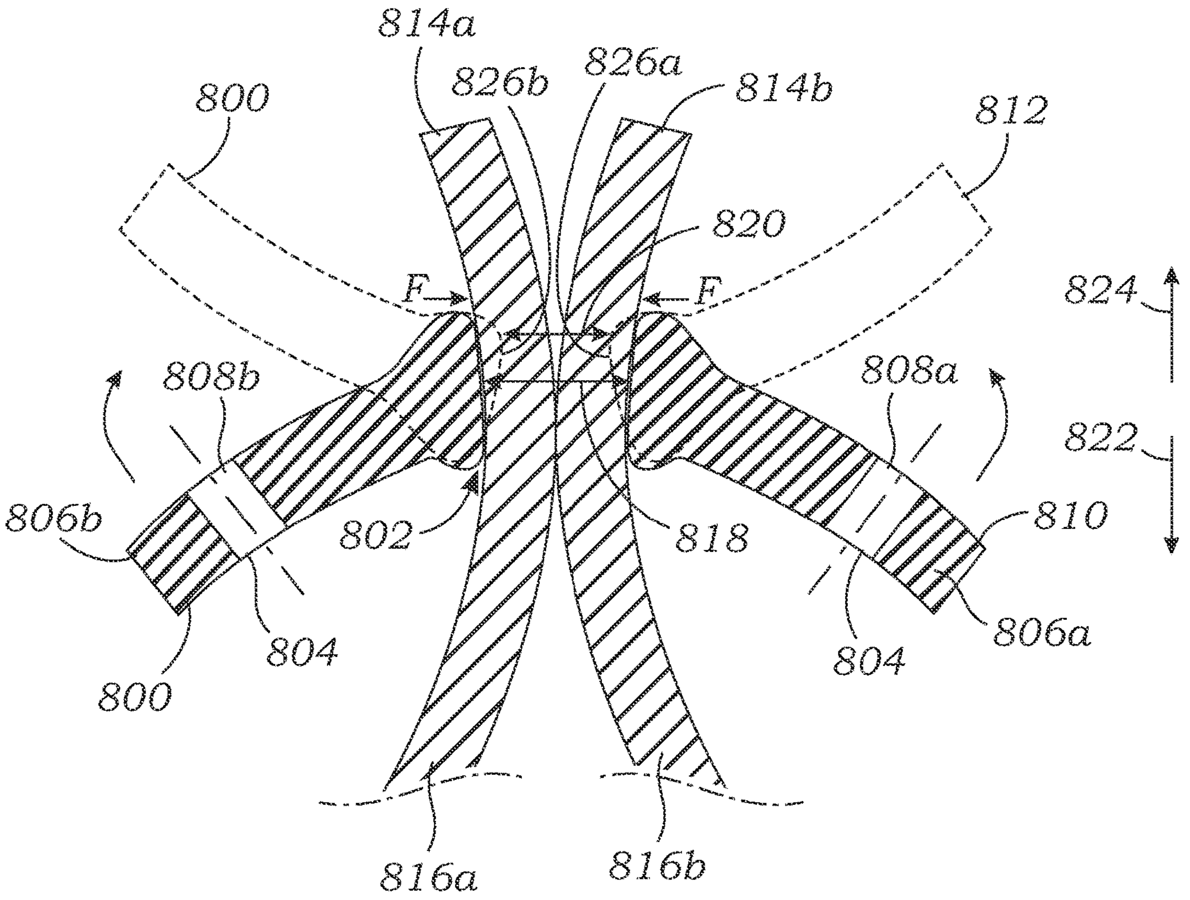
FIG. 19 is a cross-sectional view of another embodiment of a support member for a commissure attachment assembly, where the support member is configured to bend and apply a clamping force to a pair of commissure tabs arranged within a central opening of the support member.

FIG. 19 illustrates another embodiment of a support member 800 which may be used in a commissure attachment assembly, such as one of the commissure attachment assemblies discussed herein. In some embodiments, the support member 800 may be similar to the support member 302 shown in FIG. 9 and may be attached to an actuator component or another type of commissure support post of a frame of prosthetic valve, similarly to that shown in FIG. 8. In this way, the support member 800 can be configured as a rectangular plate, card, or button, having a central opening 802 and one or more openings 804 extending on either side of the central opening 802.

In some embodiments, the support member 800 may be similar to the support member 900 shown in FIG. 20, having an I-shaped central opening.

The support member 800 can be configured to bend in response to an applied force and move from a relaxed (e.g., unbent or not bent by an applied force) state to a bent (e.g., actively bent by an applied force) state. In some embodiments, to enable such bending, the support member 800 can comprise a relatively flexible material. For example, in some embodiments, the support member 800 can be relatively thin and comprise a biocompatible material such as nitinol, stainless steel, cobalt-chromium, and/or a polymeric material (such as one or more of the materials described above with reference to the support member 202). In other embodiments, to enable the bending described below, the support member 800 can comprise a flexible polymeric material.

The material and thickness of the support member 800 may be selected to achieve a desired degree of bending from the relaxed to bent state while also applying sufficient force against the leaflets in the bent state, in order to hold the leaflets within the opening of the support member 800, as described further below.

FIG. 19 shows a cross-section of the support member 800 in two different states: a relaxed state (shown by solid lines) 810 and a bent state (shown by dashed lines) 812. As introduced above, the support member 800 includes a central opening 802 defined between two side portions 806_a_ and 806_b_. Each side portion 806_a_ and 806_b_ can include a plurality of axially extending openings (e.g., apertures) 808_a_ and 808_b_, respectively, for receiving sutures. In some embodiments, the openings 808_a_ and 808_b_ may be arranged similarly to openings 308 of support member 300, as shown in FIG. 9.

The support member 800 is configured to bend around a central longitudinal axis (the longitudinal axis is orthogonal to the page in FIG. 19). The central longitudinal axis can be a central axis of the support member 800 which is arranged in the axial direction and approximately parallel with a central longitudinal axis of a frame of a prosthetic heart valve when the support member 800 is coupled to an actuator component or support structure of the frame, as described herein.

FIG. 19 shows an inward radial direction 822 and outward radial direction 824, for reference. These directions are relative to the central longitudinal axis of the frame of the prosthetic heart valve. For example, when the support member 800 is coupled to the frame of the prosthetic heart valve (e.g., mounted to the actuator component), the inward radial direction 822 points toward the central longitudinal axis of the frame while the outward radial direction 824 points toward the actuator component of the frame.

As illustrated in FIG. 19, commissure tabs 814_a_ and 814_b_ of respective leaflets 816_a_ and 816_b_ may extend through the central opening 802 in the relaxed state 810 of the support member 800. As shown in FIG. 19, the central opening 802 has a first width 818 in the relaxed state 810. The width 818 desirably is selected to allow an assembler to easily insert or "thread" the commissure tabs 814_a_, 814_b_ through the opening 802 with no or minimal resistance.

In some embodiments, as shown in FIG. 19, when in the relaxed state 810, the support member 800 can be curved (or angled in other embodiments) in the inward radial direction 822. However, in other embodiments, when in the relaxed state 810, the support member 800 can be relatively straight (e.g., not curved), as shown in FIG. 9, for example. It should be noted that the degree of curvature of the support member 800 in the relaxed state 810 and the bent state 812 may be exaggerated in FIG. 19 for the purpose of illustration.

When the support member 800 is tightly secured (e.g., by a suture extending through the openings 808_a_ and 808_b_) to the actuator component or other support post of the frame of the prosthetic valve, the side portions 806_a_ and 806_b_ bend radially outward, in the radially outward direction 824, toward and/or around the actuator component. In the bent state 812, inner edges 826_a_ and 826_b_ of the central opening 802 extend toward each other, decreasing the width of the central opening 802 to a second width 820. More specifically, the radially-outward ends of the inner edges 826_a_ and 826_b_ move closer together, thereby exerting a force F acting against the commissure tabs 814_a_ and 814_b_, clamping them tightly against each other within the central opening 802.

In this way, a shape of the central opening 802 changes as the support member 800 is bent in the radially outward direction 824. Specifically, at least a portion of the central opening 802 becomes narrower and presses inward, against the commissure tabs 814_a_ and 814_b_, to clamp the commissure tabs 814_a_ and 814_b_ tightly therein.

The bending of the support member 800, from the relaxed state 810 to the bent state 812, and thus the increase pressure against the commissure tabs 814_a_ and 814_b_, is achieved through the action of assembling (e.g., securing) the support member 800 to the actuator component of the frame of the prosthetic heart valve (e.g., as shown in FIG. 8).

Further, in operation, when the prosthetic heart valve is implanted in a heart of a patient and working, as the leaflets 816_a_ and 816_b_ are pulled in the radially inward direction 822, the clamping force, F, on the commissure tabs 814_a_ and 814_b_ by the narrowed central window 802 is further increased. As a result, radial or axial displacement of the leaflets relative to the support member 800 and/or the actuator component is reduced, thereby increasing the stability of the commissure attachment assembly.

In some embodiments, the portions of the commissure tabs 814_a_ and 814_b_ arranged on an outer side of the support member 800 (e.g., closer to the actuator component) are folded around a radially outward facing side of the support member 800, similarly to that shown in FIG. 8. Thus, when the support member 800 is fastened to the actuator component the end portions of the commissure tabs 814_a_ and 814_b_ can be arranged between the support member 800 and the actuator component.

In some embodiments, the commissure tabs 814_a_ and 814_b_ can be assembled together with the support member 800 prior to attachment of the support member 800 to the actuator component of the frame of the prosthetic heart valve.

In alternate embodiments, the central opening 802 of the support member 800 may have a different shape, size, and/or degree of curvature than shown in FIG. 19 while still providing the increased clamping force when moved to the bent state 812 upon securing the support member 800 to the actuator component of the frame of the prosthetic heart valve.

For example, in some embodiments, the inner edges 826_a_ and 826_b_ can be wider or thicker than a width or thickness of the remainder of the side portions 806_a_ and 806_b_. For example, the inner edges 826_a_ and 826_b_ can extend radially outward to a higher degree (toward the actuator component), such that in the bent state 812 of the support member 800, the radially-outward ends of the inner edges 826_a_ and 826_b_ may come closer together, to further narrow the opening of the central opening 802 and provide a higher clamping force to the commissure tabs 814_a_ and 814_b_.

In this way, the support member 800 provides an additional clamping mechanism to secure the commissure tabs 814_a_ and 814_b_ against each other within the central window 802 as compared to a relatively rigid support member (e.g., where a width of the central window does not decrease and exert a force against the commissure tabs upon securing to an actuator component of the frame).

FIG. 20 illustrates another embodiment of a support member 900 which may be used in a commissure attachment assembly, such as one of the commissure attachment assemblies discussed herein. The support member 900 may be used in place of other support members described herein, such as the support member 302 shown in FIG. 9.

In some embodiments, the support member 900 may be similar to the support member 302 shown in FIG. 9 (as described above), but with a differently shaped central opening, as described further below. The support member 900 may be attached to an actuator component or other commissure post of a frame of prosthetic valve, similarly to that shown in FIG. 8. In this way, the support member 900 can be configured as a rectangular plate, card, or button, having a central opening 902 having an I-shape and one or more openings 904 extending on either side of the central opening 902. For example, the I-shape of the central opening 902 can be defined by two opposing wider portions arranged on either side of an elongate narrower portion.

As shown in FIG. 20, the central opening 902 of the support member 900 is arranged between two side portions 906*a* and 906*b*. Each side portion 906*a* and 906*b* can include a plurality of axially extending openings (e.g., apertures) 904. A width 908 of the central opening 902 (e.g., width of portion between the wider portions forming the "I") is defined by a distance between its side edges 910*a* and 910*b*.

Figure 21:
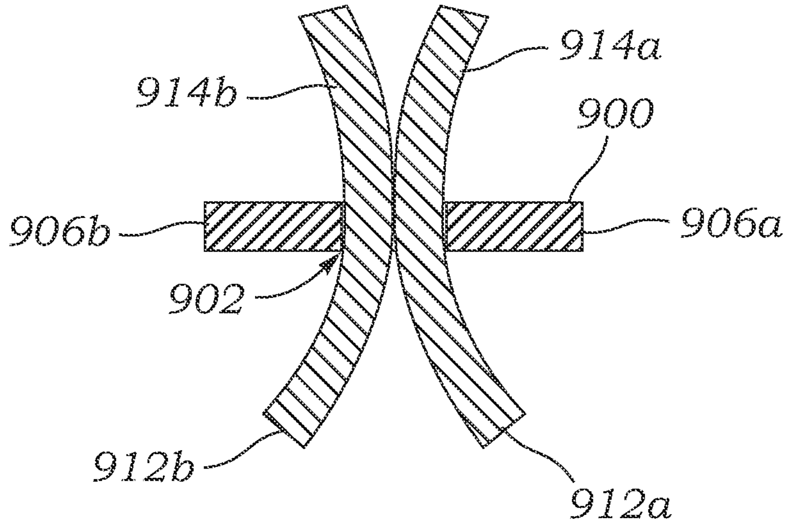
FIG. 21 is a cross-sectional view of the support member of FIG. 20.

As shown in FIG. 21, two commissure tabs 914*a* and 914*b* of two leaflets 912*a* and 912*b* can extend through the central opening 902. In some embodiments, the width 908 can be selected to be narrow enough to retain the commissure tabs 914*a* and 914*b* tightly pressed against each other within the central opening 902 so that the commissure tabs 914*a* and 914*b* cannot be pulled back through the window (in the radially inward direction) during operation of the prosthetic heart valve. However, the selected width of the central opening 902 for retaining the commissure tabs 914*a* and 914*b* therein may make it challenging to extend the commissure tabs 914*a* and 914*b* through the central opening 902 during assembly.

Making the entirety or a portion of the support member relatively thin and flexible, commissure tabs of leaflets may be more easily inserted through a central opening of the support member during assembly while also providing a sufficient tightening or clamping force against the leaflets, within the central opening, after being inserted therethrough.

Figure 22:
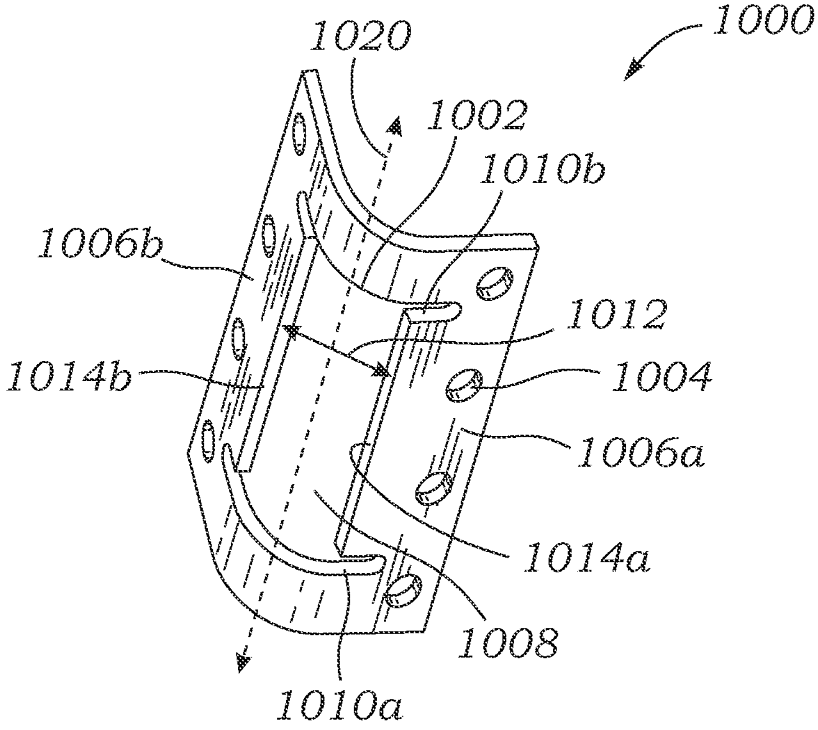
FIG. 22 is a perspective view of an embodiment of a flexible support member for a commissure attachment assembly.
Figure 23:
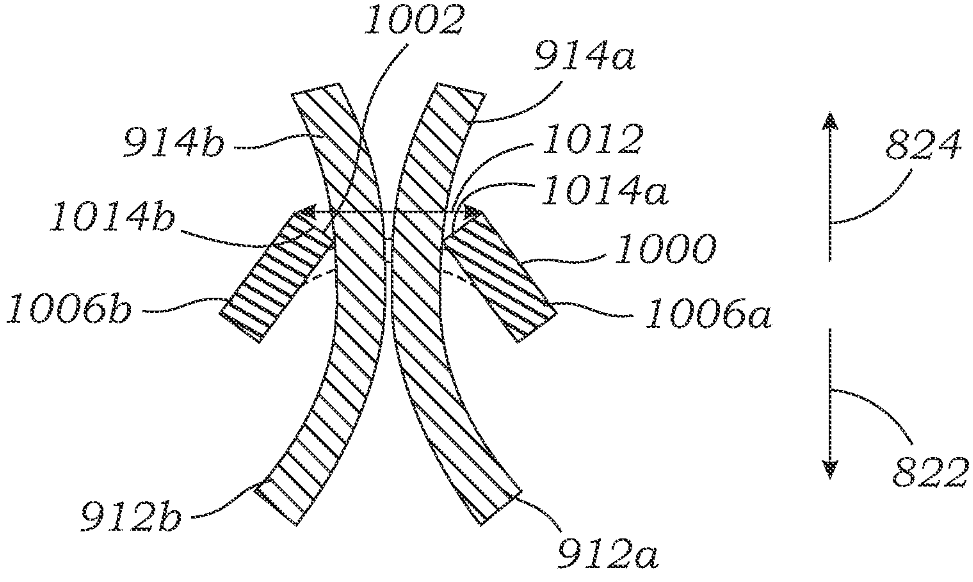
FIG. 23 is a cross-sectional view of the support member of FIG. 22 in a bent state.
Figure 24:
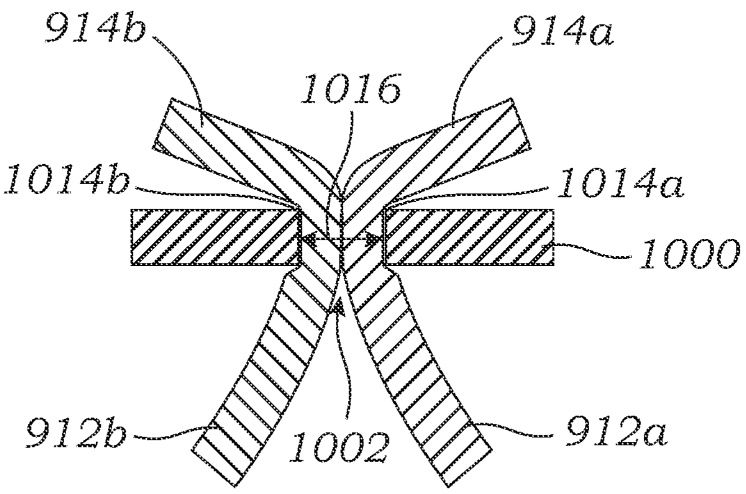
FIG. 24 is a cross-sectional view of the support member of FIG. 22 in a relaxed, unbent state.

FIGS. 22-24 illustrate an embodiment of a support member 1000 that enables easier extension of commissure tabs 914*a* and 914*b* of a pair of leaflets 912*a* and 912*b* through a central opening (e.g., window) 1002 of the support member 1000 while maintaining a width of the central opening 1002 narrow enough to provide a sufficient clamping force against the commissure tabs 914*a* and 914*b* in order to retain the commissure tabs 914*a* and 914*b* within the central opening 1002. In some embodiments, the support member 1000 may be relatively thin and/or comprise a flexible material.

The support member 1000 may be used in a commissure attachment assembly, such as one of the commissure attachment assemblies discussed herein. In some embodiments, the support member 1000 may be attached to an actuator component or other commissure support post of a frame of prosthetic valve, similarly to that shown in FIG. 8. The support member 1000 can be configured as a rectangular plate, card, or button.

In some embodiments, as shown in FIG. 22, the support member 1000 may be configured similar to the support member 900 shown in FIG. 20, except that the support member 1000 can be configured to bend in a radial direction (e.g., the radially inward direction 822, as shown in FIG. 23). As explained above, when the support member 1000 is coupled to the frame of the prosthetic heart valve (e.g., mounted to the actuator component), the inward radial direction 822 points toward the central longitudinal axis of the frame while the outward radial direction 824 points toward the actuator component of the frame.

As shown in FIG. 22, the support member 1000 comprises the central opening (e.g., window) 1002 defined between two side portion 1006*a* and 1006*b*. The side portions 1006*a* and 1006*b* can include a plurality of axially extending openings (e.g., apertures) 1004 for receiving sutures (the openings 1004 are not shown in FIGS. 23 and 24 for ease of illustration).

The support member 1000 is configured to bend around a central longitudinal axis 1020 which is centered in the center of the central opening 1002 and runs axially along a length of the central opening 1002 (the central longitudinal axis 1020 is orthogonal to the page in FIGS. 23 and 24)). Thus, in some embodiments, when the support member 1000 is coupled to an actuator component of a frame of a prosthetic heart valve, the central longitudinal axis 1020 of the support member 1000 is arranged in parallel with the central longitudinal axis of the frame.

In some embodiments, as shown in FIG. 22, the central opening 1002 is an I-shaped opening, similar to that shown in FIG. 20 (as described above). The I-shaped central opening 1002 can include a central longitudinal portion 1008 and two slots 1010*a* and 1010*b* extending perpendicularly to the central longitudinal portion 1008 at both ends thereof. The I-shaped central opening 1002 may enable easier bending of the support member 1000.

In alternate embodiments, the central opening 1002 may not be I-shaped and may instead just have a central longitudinal portion, such as that of the support member 300 shown in FIGS. 8 and 9.

The support member 1000 may be bent radially inward in the radially inward direction 822 (e.g., toward a central longitudinal axis of the valve, when the support member is assembled thereto) prior to extending the commissure tabs 914*a* and 914*b* through the central opening 1002, as shown in FIG. 22. In alternate embodiments, the support member 1000 may be bendable in the radially outward direction 824 prior to extending the commissure tables 914*a* and 914*b* through the central opening 1002.

In this bent state, the width of the central opening 1002 is widened to a first width 1012, distancing the side edges 1014*a* and 1014*b* away from each other, thereby enabling easier extension of the commissure tabs 914*a* and 914*b* through the central opening 1002, as shown in FIG. 23.

Once the commissure tabs 914*a* and 914*b* are sufficiently extended through the central opening 1002, the support member 1000 may be released back to its unbent, or relaxed, state, as shown in FIG. 24. This unbent state may also be referred to as the support member's non-deformed state (shown in FIG. 24).

As shown in FIG. 24, in this released and unbent state, the central opening 1002 re-assumes its relatively narrow second width 1016 between the side edges 1014*a* and 1014*b*. As a result of this narrower, second width 1016, the side edges 1014*a* and 1014*b* exert a sufficient tightening (e.g., clamping) force against a portion of the commissure tabs 914*a* and 914*b* arranged within the central opening 1002, in order to press the commissure tabs 914*a* and 914*b* tightly against each other and prevent sliding or other movement of the leaflets within the support member 1000.

In some embodiments, the portions of the commissure tabs 914*a* and 914*b* arranged on an outer side of the support member 1000 (e.g., closer to the actuator component) are folded around a radially outward facing side of the support member 1000, similarly to that shown in FIG. 8. Thus, when the support member 1000 is fastened to the actuator component the end portions of the commissure tabs 914*a* and 914*b* can be arranged between the support member 1000 and the actuator component.

The leaflets 912*a* and 912*b* can be assembled together with the support member 1000 prior to attachment of the support member 1000 to the actuator component of the frame.

In some embodiments, the support member 1000 is elastically bendable, such that it may re-assume its released and relatively unbent shape, as shown in FIG. 24, as soon as bending forces are no longer applied to the support member 1000.

In some embodiments, the support member 1000 is plastically deformable (e.g., comprises a plastically deformable material, such as one of the plastically deformable materials discussed herein), such that it can be deformed to the bent state (shown in FIGS. 22 and 23), and then be plastically deformed back to the released state (shown in FIG. 24). Alternatively, the support member 1000 may be manufactured in the bent state and then plastically deformed into the released and relatively unbent state. Having a support member 1000 that is plastically deformable (e.g., comprises a plastically deformable material) may simplify the process of leaflets insertion through the central opening 1002, by not requiring continuous force application on the support member 1000 during the bending stage (shown in FIGS. 22 and 23).

In this way, the support member 1000 can comprise elastically-deformable or plastically-deformable metals or polymeric materials, or combinations thereof, such as those discussed herein with reference to embodiments of the prosthetic heart valve and support member components.

In some embodiments, an entirety of the support member 1000 comprises a flexible material (e.g., elastically-deformable and/or plastically-deformable metals or polymeric materials).

In this way, the support member 1000 enables easier extension of the commissure tabs 914*a* and 914*b* through the central opening 1002, while keeping the dimensions (e.g., width) of the central opening 1002 narrow enough to clamp the commissure tabs 914*a* and 914*b* together once retained therein. Further, the clamping forces against the commissure tabs 914 and 914*b* of the leaflets are achieved within the support member 1000 itself, regardless of its tightening to the actuator component of the frame. Thus, the leaflets may be arranged and tightened within the support member 1000 prior to assembling the commissure to the frame of the prosthetic heart valve.

Figure 25:
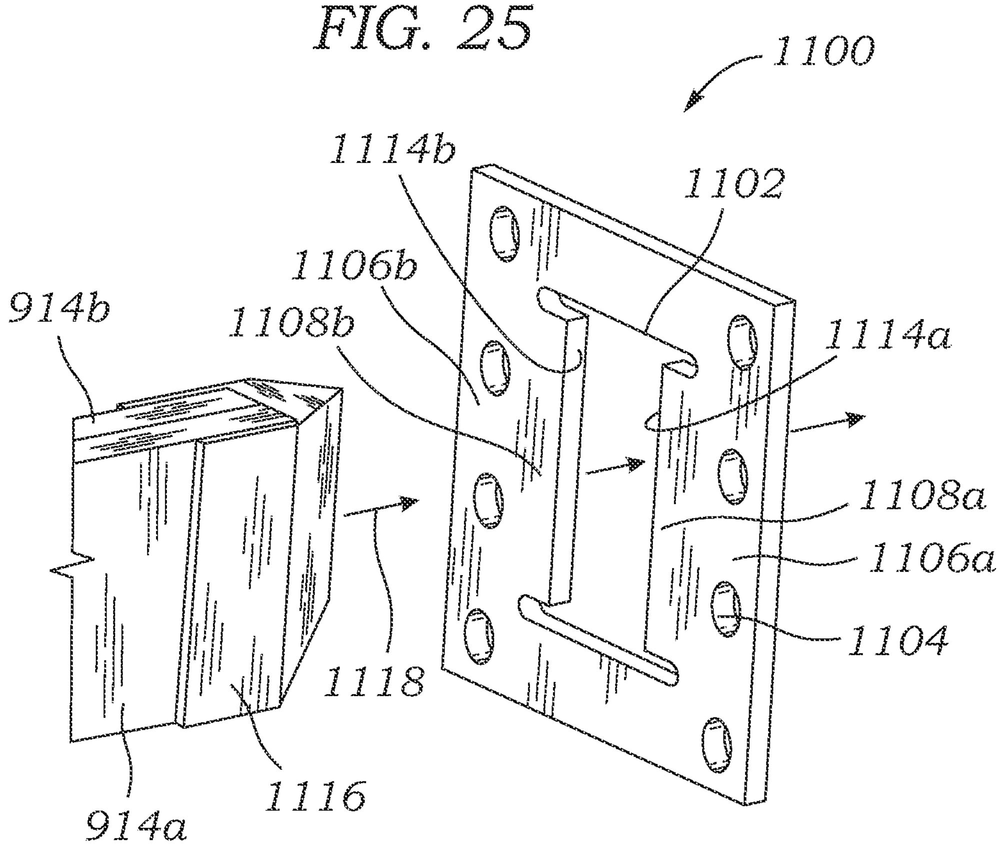
FIG. 25 is a perspective view of another embodiment of an at least partially flexible support member for a commissure attachment assembly, the support member having side portions around a central opening that are configured to bend.
Figure 26:
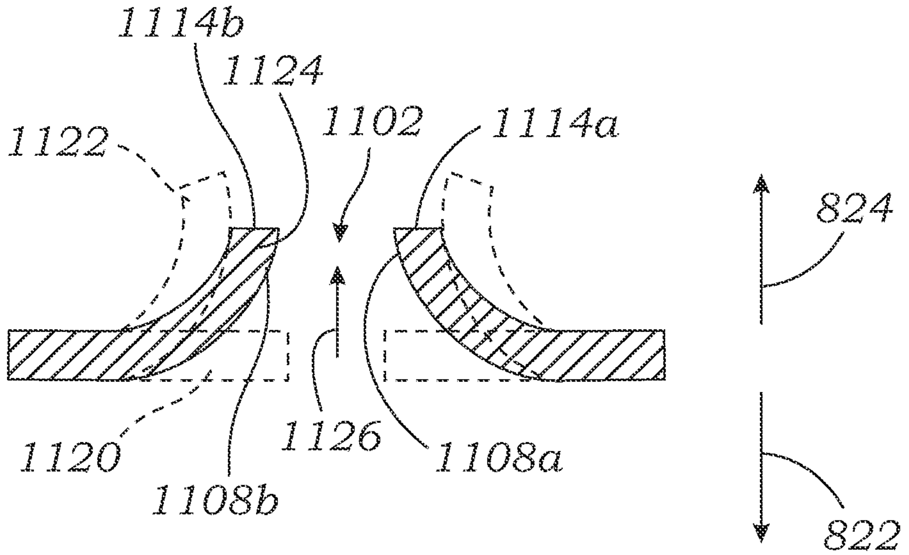
FIG. 26 is a cross-sectional view of the support member of FIG. 25 in three different states of bending.
Figure 27:
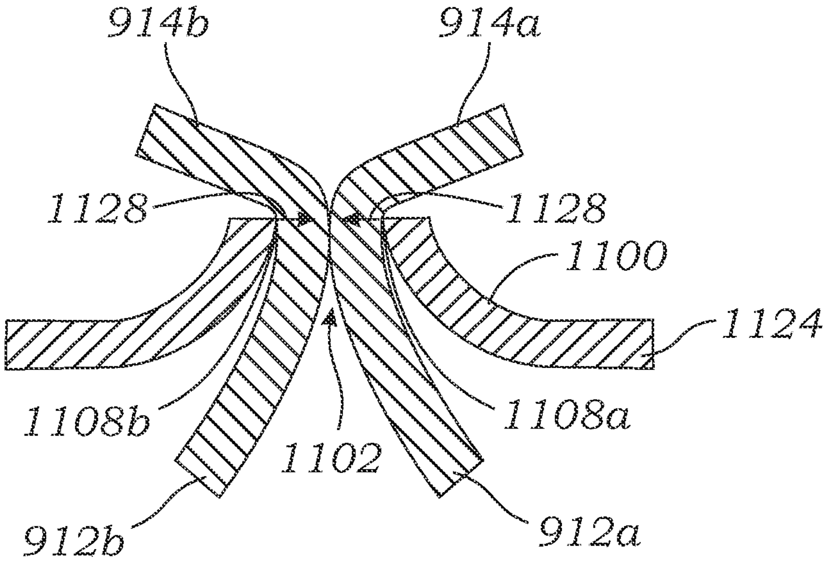
FIG. 27 is a cross-sectional view of the support member of FIG. 25, where inner portions of the side portions are bent radially outward and biased against a pair of commissure tabs of the commissure attachment assembly.

FIGS. 25-27 illustrate another embodiment of a support member 1100 that enables easier extension of commissure tabs of a pair of leaflets through a central opening (e.g., window) 1102 of the support member 1100 while maintaining a width of the central opening 1102 narrow enough to provide a sufficient clamping force to the commissure tabs in order to retain the commissure tabs within the central opening 1102. In some embodiments, the support member 1100 may be relatively thin and comprise a flexible material such that side portions around the central opening 1102 are flexible enough to bend radially outward when a force is applied thereto, in the same direction. In other embodiments, the support member 1100, or at least a portion of the support member 1100 arranged around the central opening 1102, may comprise a flexible material.

The support member 1100 may be used in a commissure attachment assembly, such as one of the commissure attachment assemblies discussed herein. In some embodiments, the support member 1100 may be attached to an actuator component or other commissure post of a frame of prosthetic valve, similarly to that shown in FIG. 8. The support member 1100 can be configured as a rectangular plate, card, or button.

In some embodiments, as shown in FIG. 25, the support member 1100 may be configured similar to the support member 900 shown in FIG. 20, except that at least inner portions of side edges 1114*a* and 1114*b* of the central opening 1102 are configured to bend in a radial direction (e.g., the radially outward direction 824, as shown in FIG. 26) when the commissure tabs 914*a* and 914*b* are forcibly (e.g., via an external force) pulled (or pushed) through the central opening 1102.

As explained above, when the support member 1000 is coupled to the frame of the prosthetic heart valve (e.g., mounted to the actuator component), the inward radial direction 822 points toward the central longitudinal axis of the frame while the outward radial direction 824 points toward the actuator component of the frame.

As shown in FIG. 22, the support member 1100 comprises the central opening (e.g., window) 1102 defined between two side portions 1106*a* and 1106*b*. The side portions 1106*a* and 1106*b* can include a plurality of axially extending openings (e.g., apertures) 1104 (the openings 1104 are not shown in FIGS. 26 and 27 for ease of illustration).

In some embodiments, as shown in FIG. 25, the central opening 1102 is an I-shaped opening, similar to that shown in FIG. 20 (as described above).

In alternate embodiments, the central opening 1102 may not be I-shaped and may instead just have a central longitudinal portion, such as that of the support member 300 shown in FIGS. 8 and 9.

FIGS. 26 and 27 show a sectional view of the support member 1000 in different stages during insertion of the commissure tabs of the leaflets through the central window 1102.

As shown in FIGS. 25, a width of the central opening 1102 is defined between its side edges 1114*a* and 1114*b*. Inner portions 1108*a* and 1108*b* of the side portions 1106*a* and 1106*b* are defined as the portions that are arranged adjacent (e.g., directly adjacent) to the side edges 1114*a* and 1114*b* of the central opening 1102.

As shown in FIGS. 26 and 27, the inner portions 1108*a* and 1108*b* can be configured to bend radially outward, in the radially outward direction 824, when a force is applied thereto in the same (radially outward) direction.

Specifically, FIG. 26 shows the support member 1100 in three different states, including a first, resting state 1120 which may be the initial state of the support member 1000, prior to insertion of the commissure tabs 914*a* and 914*b* of the leaflets 912*a* and 912*b* (as shown in FIG. 25), a second, bent state, 1122, and a third, relaxed (and bent) state 1124.

For example, as shown in FIG. 25, the commissure tabs 914*a* and 914*b* of respective leaflets can be inserted into the central opening 1102, in the radial outward direction 824, as shown by arrows 1118. In some embodiments, a jig or clamp member 1116 may be used to clamp the commissure tabs 914*a* and 914*b* together, in order to facilitate insertion through the central opening 1102.

In some embodiments, the clamp member 1116 may be in the form of a rigid jig, enabling it to be forcibly pushed through the central opening 1102.

Alternatively, in other embodiments, the clamping member 1116 can be in the form of a flexible cloth, enabling it to be pulled through the central opening 1102.

As the commissure tabs 914*a* and 914*b* are actively pulled through the central opening 1102, the inner portions 1108*a* and 1108*b* of the side portions 1106*a* and 1106*b* of the support member 1100 are bent radially outward to a greater degree, as shown by the second, bent state 1122 in FIG. 26. The radially outward force 1126 pushing the inner portions 1108*a* and 1108*b* in the radially outward direction 824 is created by the commissure tabs 914*a* and 914*b* (and/or the clamp member 1116) pressing against the surface of the inner portions 1108*a* and 1108*b*, as the commissure tabs 914*a* and 914*b* are being pulled through the central opening 1102, in the radially outward direction 824. In this way, at least the inner portions 1108*a* and 1108*b* of the support member 1100 bend radially outward, from the first, resting state 1120 to the second, bent state 1122, when a force (the radially outward force 1126 shown in FIG. 26) is applied in the same direction, as shown in FIG. 26.

Once the commissure tabs 914*a* and 914*b* are arranged within the central opening 1102 and are no longer being actively inserted and pulled through the central opening 1102 (in the radially outward direction), the radially outward force 1126 is removed. As a result, the inner portions 1108*a* and 1108*b* can relax and transition to the third, relaxed state 1124. As shown in FIG. 26, in the third, relaxed state 1124, the support member 1100 is bent to a lesser degree than in the second, bent state 1122.

FIG. 27 shows the commissure tabs 914*a* and 914*b* extended through the central opening 1102, where the inner portions 1108*a* and 1108 are bent radially outward and are biased against the commissure tabs 914*a* and 914*b*, respectively. As a result, the inner portions 1108*a* and 1108*b* exert a clamping force 1128 that is large enough to press the commissure tabs 914*a* and 914*b* against each other and prevent the commissure tabs 914*a* and 914*b* from being slid or pulled out of the central opening 1102 during operation of the prosthetic heart valve.

In some embodiments, while the inner portions 1108*a* and 1108*b* are configured to bend radially outward and be biased against the commissure tabs 914*a* and 914*b* arranged therein, a remainder of the side portions 1106*a* and 1106*b* (e.g., remaining, outer portions of the side portions) may remain relatively unbent (e.g., as shown in FIGS. 26 and 27).

The clamp member 1116 can be removed after the commissure tabs 914*a* and 914*b* have been extended through the central opening 1102.

In some embodiments, as shown in FIG. 27, the configuration of the support member 1100, as described above, results in the commissure tabs 914*a* and 914*b* being pressed against each other, between the inner portions 1108*a* and 1108*b*, which are pressed against the commissure tabs 914*a* and 914*b*. This is in contrast to the commissure tabs 914*a* and 914*b* being pressed between the side edges 1114*a* and 1114*b* of the central opening 1102 (e.g., as shown in FIG. 21).

At least a portion of the support member 1100, in the region of the inner portions 1108*a* and 1108*b* can be comprised of a flexible material in order to provide the bending described above. For example, in some embodiments, the side portions 1108*a* and 1108*b* or a portion of the support member 1100 including the side portions 1108*a* and 1108*b* can be relatively thin (e.g., thinner than a remainder of the support member 1100) and comprise a biocompatible material such as nitinol, stainless steel, cobalt-chromium, and/or a polymeric material (such as one or more of the materials described above with reference to the support member 202). In other embodiments, to enable the bending of the inner portions 1108*a* and 1108*b*, the side portions 1108*a* and 1108*b* or a portion of the support member 1100 including the side portions 1108*a* and 1108*b* can comprise a flexible polymeric material.

In some embodiments, the portions of the commissure tabs 914*a* and 914*b* arranged on an outer side of the support member 1100 (e.g., closer to the actuator component) are folded around a radially outward facing side of the support member 1100, similarly to that shown in FIG. 8. Thus, when the support member 1100 is fastened to the actuator component the end portions of the commissure tabs 914*a* and 914*b* can be arranged between the support member 1100 and the actuator component.

The leaflets 912*a* and 912*b* can be assembled together with the support member 1100 prior to attachment of the support member 1100 to the actuator component of the frame.

In this way, the support member 1100 enables easier extension of the commissure tabs 914*a* and 914*b* through the central opening 1102, while keeping the width of the central opening 1102 narrow enough to clamp the commissure tabs 914*a* and 914*b* together in the central opening 1102. Further, the clamping forces 1128 against the commissure tabs 914 and 914*b* of the leaflets are achieved within the support member 1100 itself, regardless of its tightening to the actuator component of the frame. Thus, the leaflets may be arranged and tightened within the support member 1000 prior to assembling the commissure to the frame of the prosthetic heart valve.

Further, by configuring the support member 1100 with inner portions 1108*a* and 1108*b* that are flexible and configured to bend radially outward (away from the central longitudinal axis of the prosthetic heart valve and toward an actuator component of the frame when the support member 1100 is assembled to the frame), the clamping force 1128 against the commissure tabs 914*a* and 914*b* by the inner portions 1108*a* and 1108*b* is further increased when the leaflets are pulled in the radially inward direction, during operation of the prosthetic heart valve. This further reduces a likelihood of the commissure tabs axially slipping or rotating relative to the frame during operation of the prosthetic heart valve.

Figure 29:
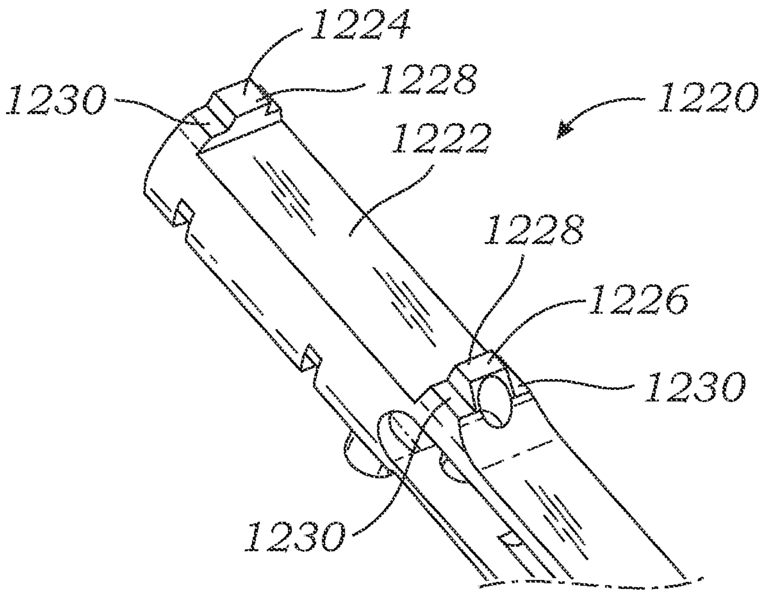
FIG. 29 is a perspective view of an inner side of an embodiment of an actuator component of a frame of a prosthetic heart valve, configured to couple with the support member of FIG. 28.
Figure 30:
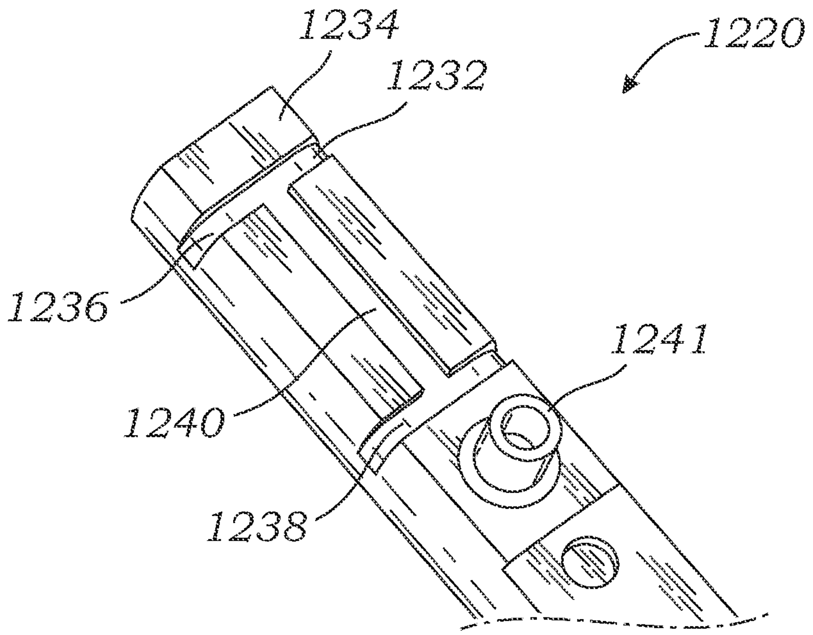
FIG. 30 is a perspective view of an outer side of the actuator component of FIG. 29.
Figure 31:
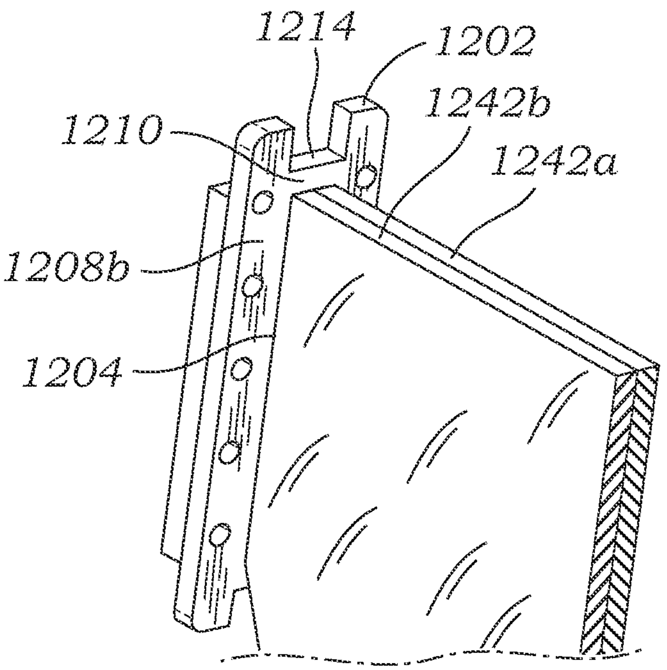
FIG. 31 is a perspective view of a pair of commissure tabs of adjacently arranged leaflets extending through a central opening of the support member of FIG. 28.

Turning now to FIGS. 28-39, another embodiment of a commissure attachment assembly 1200 is illustrated. The commissure attachment assembly 1200 includes a support member 1202 (as shown by itself in FIG. 28) which includes a central opening 1204 configured to receive commissure tabs of a pair of leaflets, respectively (as shown in FIG. 31). The support member 1202 is configured to be attached to an actuator component 1220 (as shown by itself in FIGS. 29 and 30), or another commissure support portion, of a post member of a frame of a prosthetic heart valve via one or more flexible (and deformable) attachment members (attachment members 1246*a* and 1246*b* shown in FIGS. 32-39). For example, as described further below, the support member 1202 can include a plurality of openings (e.g., apertures) 1206 arranged on either side of the central opening 1204 and the support member 1202 can be configured to be attached to the actuator component 1220 via one or more flexible attachment members that can extend through the openings 1206 and around the actuator component 1220. In some embodiments, the flexible attachment members can be elastically or plastically deformable wires. In other embodiments, the flexible attachment members can be elastically or plastically deformable polymeric members.

Figure 28:
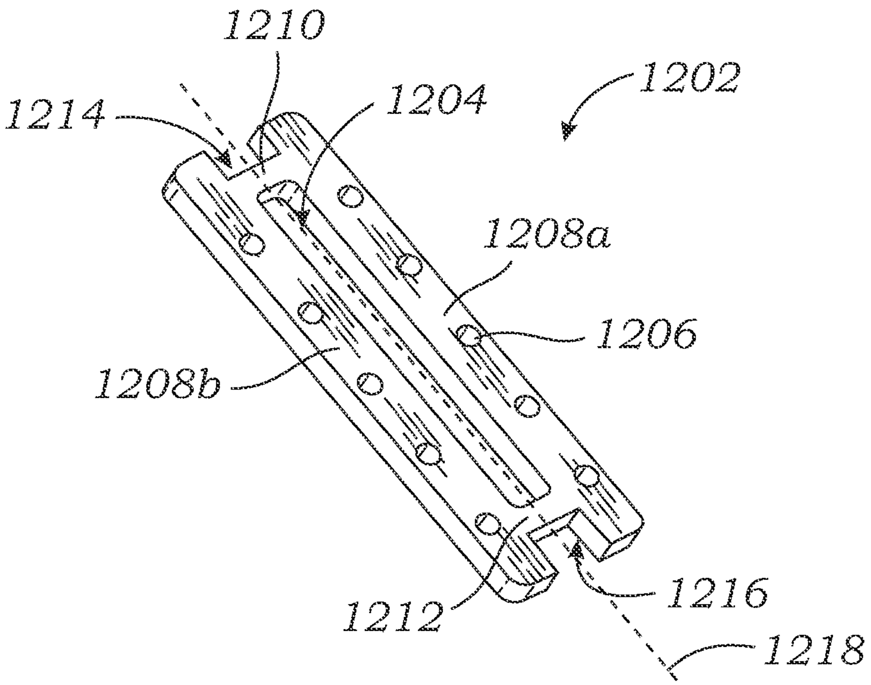
FIG. 28 is a perspective view of an embodiment of a support member for a commissure attachment assembly.

FIG. 28 illustrates the support member 1202 in greater detail. The support member 1202 can be configured as a rectangular plate, card, or button, similar to the support member 302 of FIGS. 8 and 9. In some embodiments, the support member 1202 can be formed from a relatively thin, rigid material, such as one of the metal or polymeric materials discussed above with reference to the other support member embodiments.

The support member 1202 can be manufactured by known manufacturing techniques suitable for mass productions, such as laser cutting, waterjet cutting, and the like.

The support member 1202 can include a central opening 1204 extending along the long axis of the support member 1202, the central opening 1204 bound between two side portions 1208*a* and 1208*b*, an upper portion 1210, and a lower portion 1212 of the support member 1202. In the illustrated embodiment, the central opening 1204 is rectangular, although the central opening 1204 may have any selected shape (such as oblong, I-shaped, as shown in the embodiment of FIG. 20, or the like). The plurality of openings 1206 are arranged in the two side portions 1208*a* and 1208*b*.

In some embodiments, as shown in FIG. 28, the support member 1202 includes a first notch 1214 in the upper portion 1210 and a second notch 1216 in the lower portion 1212.

In some embodiments, the central opening 1204, the first notch 1214, and the second notch 1216 can be centered along a central longitudinal axis 1218 of the support member 1202.

FIGS. 29 and 30 illustrate the actuator component 1220 in greater detail. Specifically, FIG. 29 shows an upper, inner side of the actuator component 1220 and FIG. 30 shows an upper, outer side of the actuator component 1220.

As used herein with reference to the commissure attachment assembly 1200, the term "inner side" refers to a side of a component, oriented radially inward, toward a central longitudinal axis of the valve when the component is attached thereto. The term "outer side" refers to an opposite side, oriented radially outward, away from the central longitudinal axis of the valve.

In some embodiments, the actuator component 1220 can be an outer housing of an actuator assembly (such as one of the actuator assemblies or components discussed herein) that is structured to accommodate the support member 1202 and the attachment members, such as wires, utilized to couple the support member 1202 thereto. In some embodiments, the actuator assembly may be more generically referred to as a post member, where the post member comprises the actuator component. In alternate embodiments, another type of post member of the frame may comprise the elements of the actuator component 1220 described herein with reference to FIGS. 29 and 30.

As shown in FIG. 29, the inner side of the actuator component 1220 includes a commissure receiving portion 1222, which can be formed as a relatively flat portion arranged between an upper post extension 1224 and a lower post extension 1226. The upper post extension 1224 and the lower post extension 1226 each comprise a central protruding portion 1228 and side portions 1230 arranged on either side of the central protruding portion 1228. The upper post extension 1224 is adapted to receive the first notch 1214 of the support member 1202 and the lower post extension 1226 is adapted to receive the second notch 1216 of the support member 1202. For example, when the support member 1202 is attached to the actuator component 1220, the portion of the upper portion 1210 of the support member 1202 arranged on either side of the first notch 1214 can sit against respective side portions 1230 of the upper post extension 1224 and the central protruding portion 1228 of the upper post extension 1224 can fit within and extend through the first notch 1214. Similarly, the portion of the lower portion 1212 of the support member 1202 arranged on either side of the second notch 1216 can sit against respective side portions 1230 of the lower post extension 1226 and the central protruding portion 1228 of the lower post extension 1226 can fit within and extend through the second notch 1216.

As shown in FIG. 30, the outer side of the actuator component 1220 can include a plurality of channels 1232 adapted to receive the attachment members. The plurality of channels 1232 are recessed (e.g., depressed) into the surface (e.g., outer surface) 1234 of the outer side. In some embodiments, as shown in FIG. 30, the plurality of channels 1232 can include an upper channel 1236, a lower channel 1238, and a central channel 1240. The upper channel 1236 and the lower channel 1238 can extend circumferentially around a portion of the actuator component 1220 (e.g., around at least the outer side). Thus, the upper channel 1236 and the lower channel 1238 may be referred to as circumferentially extending channels. In some embodiments, the upper channel 1236 and the lower channel 1238 can further extend around the sidewalls of the actuator component 1220. The central channel 1240 axially extends between the upper channel 1236 and the lower channel 1238 (and may be referred to as an axially extending central channel).

In some embodiments, a width of the channels 1232 can be selected based on a width of the attachment members. For example, the width of the channels 1232 can be selected to be the same or slightly larger than approximately two times the width of one attachment member in order to tightly retain the attachment members therein, as described further below.

Figure 38:
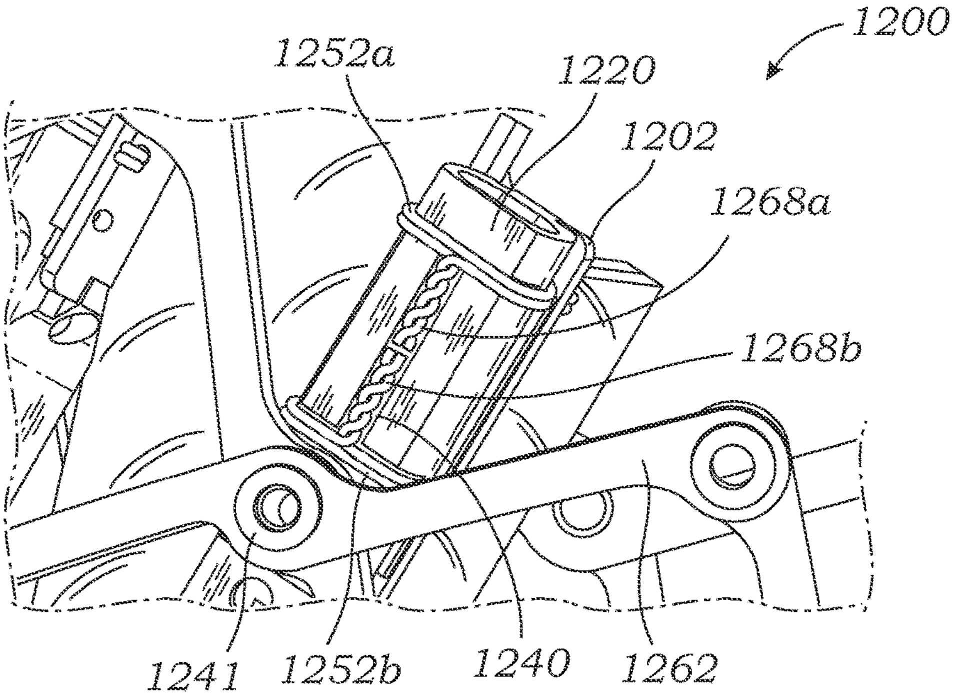
FIG. 38 is a detail view of an outer side of the commissure attachment assembly of FIG. 34, in the tightened and secured state.
Figure 39:
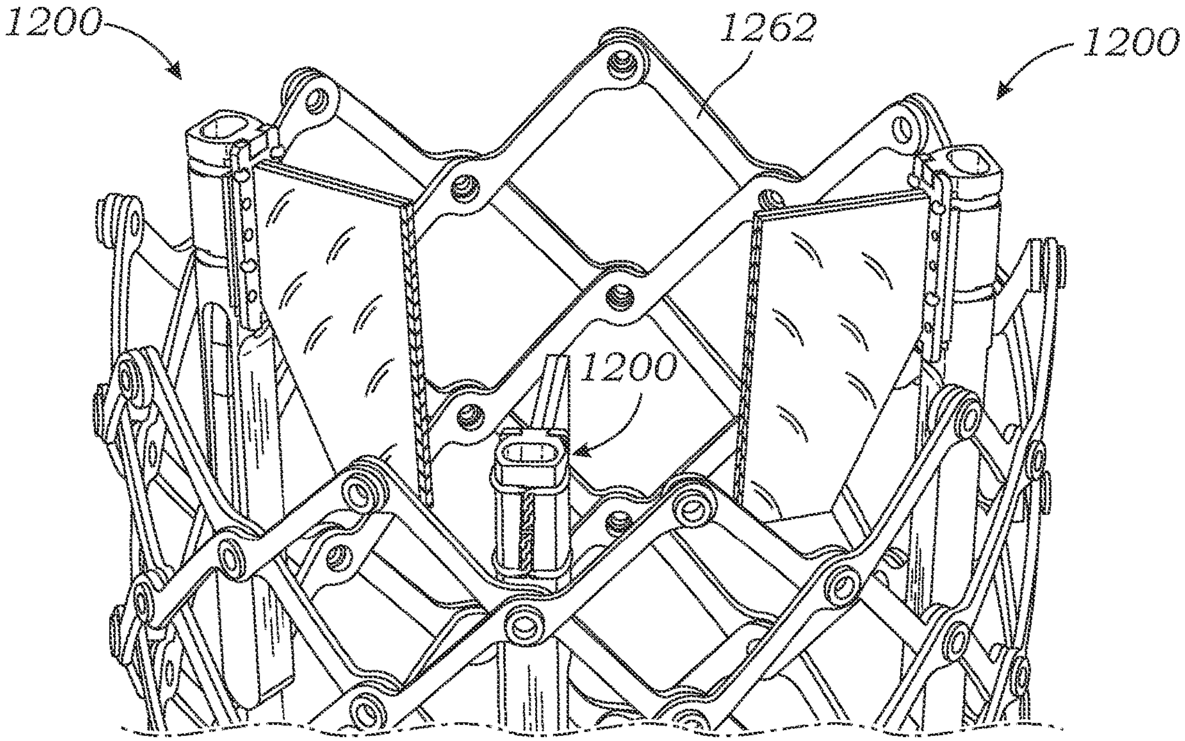
FIG. 39 is a perspective view of a prosthetic heart valve comprising a frame with three of the commissure attachment assemblies of FIG. 34.

As shown in FIG. 30, the outer side of the actuator component 1220 can further include a rivet 1241 that is adapted to be received within an aperture of a strut of a frame of the prosthetic heart valve (as shown in FIGS. 38 and 39). The lower channel 1238 is arranged closest to the rivet 1241 (relative to the other channels) while the upper channel 1236 is arranged closest to an end of the actuator component 1220 arranged at an outflow end of the frame.

FIG. 31 shows a pair of commissure tabs 1242*a* and 1242*b* of adjacently arranged leaflets (leaflets 1244*a* and 1244*b* shown in FIGS. 34-36) extending through the central opening 1204 of the support member 1202. The height and the width of the central opening 1204 may be selected based on (e.g., to accommodate) a height and width of the commissure tabs 1242*a* and 1242*b* extending therethrough.

Figure 32:
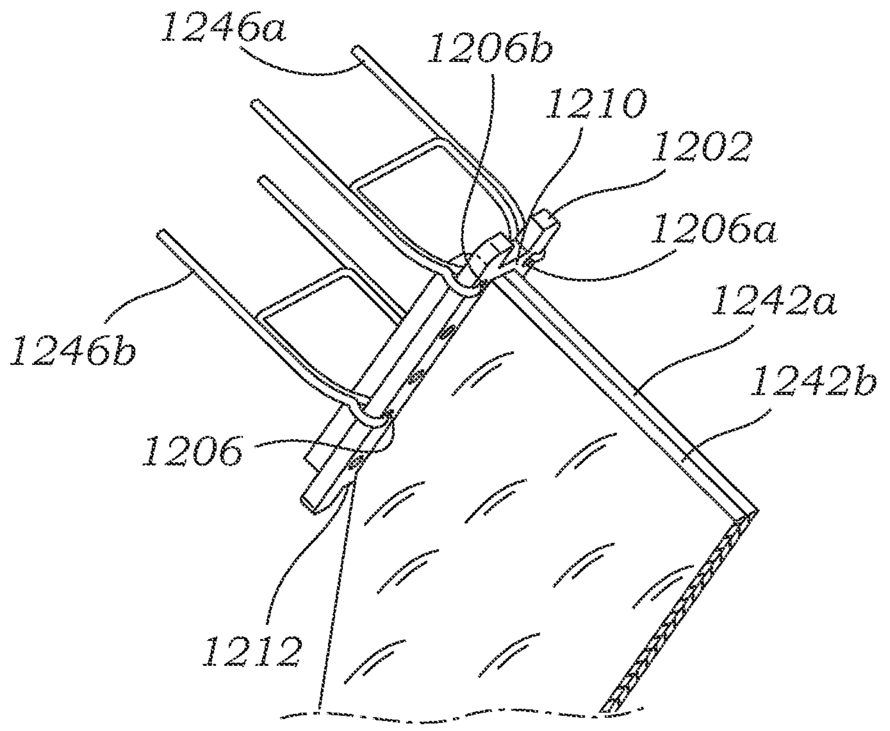
FIG. 32 is a perspective view of two flexible attachment members extending through upper and lower openings of the support member of FIG. 28.

FIG. 32 shows two attachment members 1246*a* and 1246*b*, extending through upper and lower openings 1206 of the support member 1202. In some embodiments, the upper openings may be arranged closer to the upper portion 1210 of the support member 1202 than the lower openings and the lower openings may be arranged closer to the lower portion 1212 of the support member 1202 than the upper openings. It should be noted that while two attachment members 1246*a* and 1246*b* are shown for each commissure attachment assembly in FIGS. 32-39, in alternate embodiments, more or less than two attachment members 1246*a* and 1246*b* can be used in each commissure attachment assembly (e.g., one, three, or the like).

The attachment members 1246*a* and 1246*b* can comprise a relatively flexible and deformable material that is adapted to change shape (e.g., diameter, as described further below) and be pulled through corresponding openings 1206 while also being durable and able to retain its deformed shaped. For example, in some embodiments, the attachment members 1246*a* and 1246*b* can be elastically or plastically deformable metallic wires, for example made of cobalt-chrome alloy (e.g. MP35N alloy) or nickel titanium alloy (e.g., Nitinol). In other embodiments, the attachment members 1246*a* and 1246*b* can comprise an elastically or plastically deformable polymeric material. In other embodiments, the attachment members 1246*a* and 1246*b* can comprise sutures, yarn, cords, or similar materials.

Figure 33:
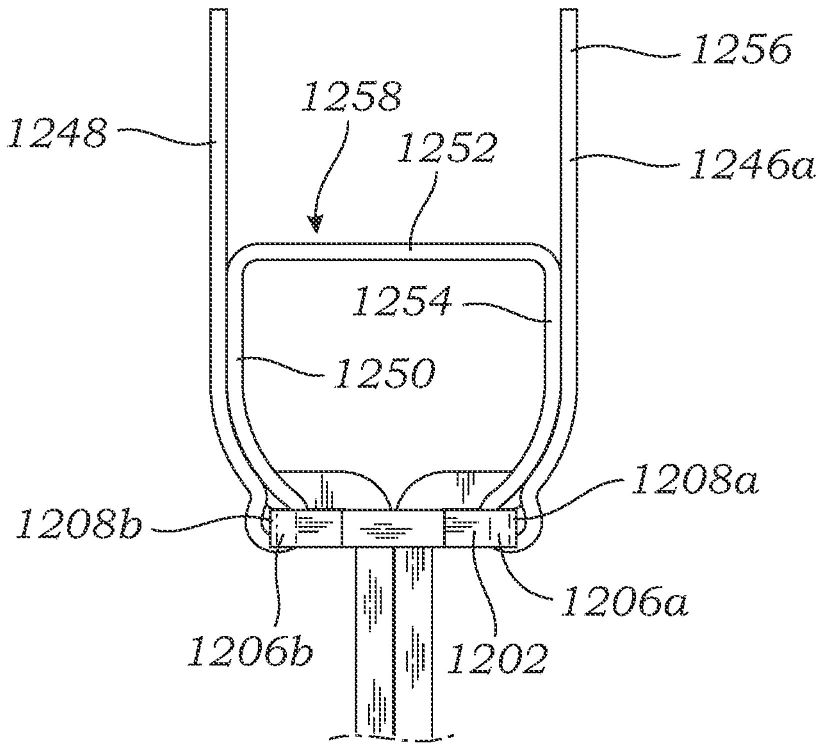
FIG. 33 is a top view of the assembly of FIG. 32, illustrating a first attachment member extending through openings of the support member.

FIG. 33 illustrates a top view of the first attachment member 1246*a* extending through openings 1206 of the support member 1202. As shown in FIG. 33, the first attachment member 1246*a* (and similarly, the second attachment member 1246*b* and any additional attachment members) can include a first side portion 1248 extending from its free end, around the second side portion 1208*b* of the support member 1202, and through an opening 1206*b* of the second side portion 1208*b*. The first attachment member 1246*a* is then bent back into a first loop side portion 1250. The first loop side portion 1250 can be arranged substantially parallel to the first side portion 1248. The first loop side portion 1250 then bends, for example by a 90° angle, to form a loop central portion 1252, and then bends again, for example by a 90° angle, to form a second loop side portion 1254. The second loop side portion 1254 can extend through an opening 1206*a* of the first side portion 1208*a* of the support member 1202, and then bend backwards to form a second side portion 1256, which may terminate at a free end thereof. The second side portion 1256 can be arranged substantially parallel with the second loop side portion 1254.

The first loop side portion 1250, the loop central portion 1252, and the second loop side portion 1254, together define a loop (e.g., wire loop) 1258, where the loop central portion 1252 is arranged substantially parallel to the upper portion 1210 and the lower portion 1212 of the support member 1202.

Figure 34:
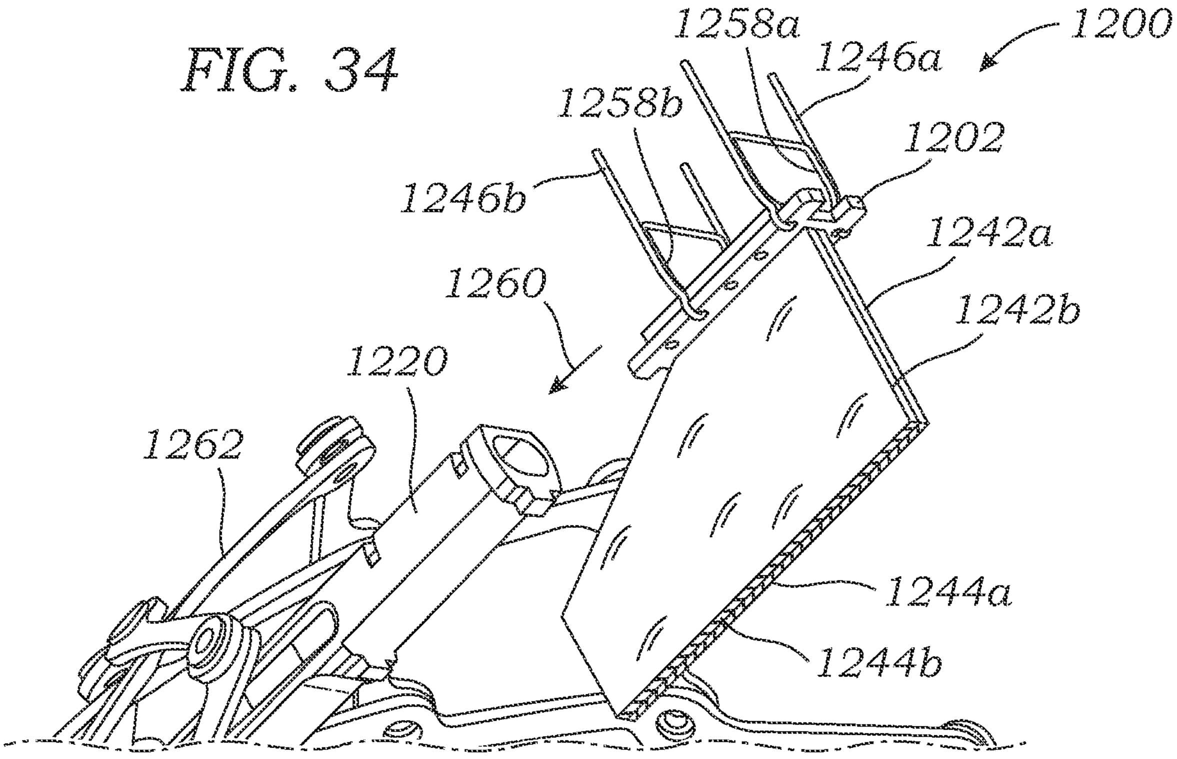
FIG. 34 is a perspective view of a stage of assembling a commissure attachment assembly, including extending the actuator component of FIG. 28 through loops of the attachment members secured to the support member, as shown in FIGS. 32 and 33.

In this way, FIG. 33 illustrates a first stage of assembling the commissure attachment assembly 1200, which can include coupling the pair of commissure tabs to the support member 1200 and creating an attachment member loop 1258 for each attachment member of the assembly (e.g., loops 1258*a* and 1258*b* for attachment members 1246*a* and 1246*b*, respectively, as shown in FIG. 34).

In some embodiments, the commissure tabs 1242*a* and 1242*b* of the leaflets of the commissure attachment assembly 1200 are attached to the support member 1202 using conventional techniques, such as sewing or suturing.

In some embodiments, the commissure tabs 1242*a* and 1242*b* extending through the central opening 1204 extend sideways along the outer sides of the side portions 1208*a* and 1208*b* (e.g., are folded over the outer side of the support member, similarly to as shown in FIG. 8). Then, in some embodiments, the attachment members 1246*a* and 1246*b* extending through corresponding openings 1206, further extend through the respective commissure tabs flattened over the respective side portions 1208*a* and 1208*b*. Such configurations may assist in coupling the commissure (including the paired commissure tabs 1242*a* and 1242*b*) to the support member 1202, and may, in some embodiments, eliminate the need to utilize additional coupling means such as sutures extending between the commissure tabs and the support member 1202.

Figure 35:
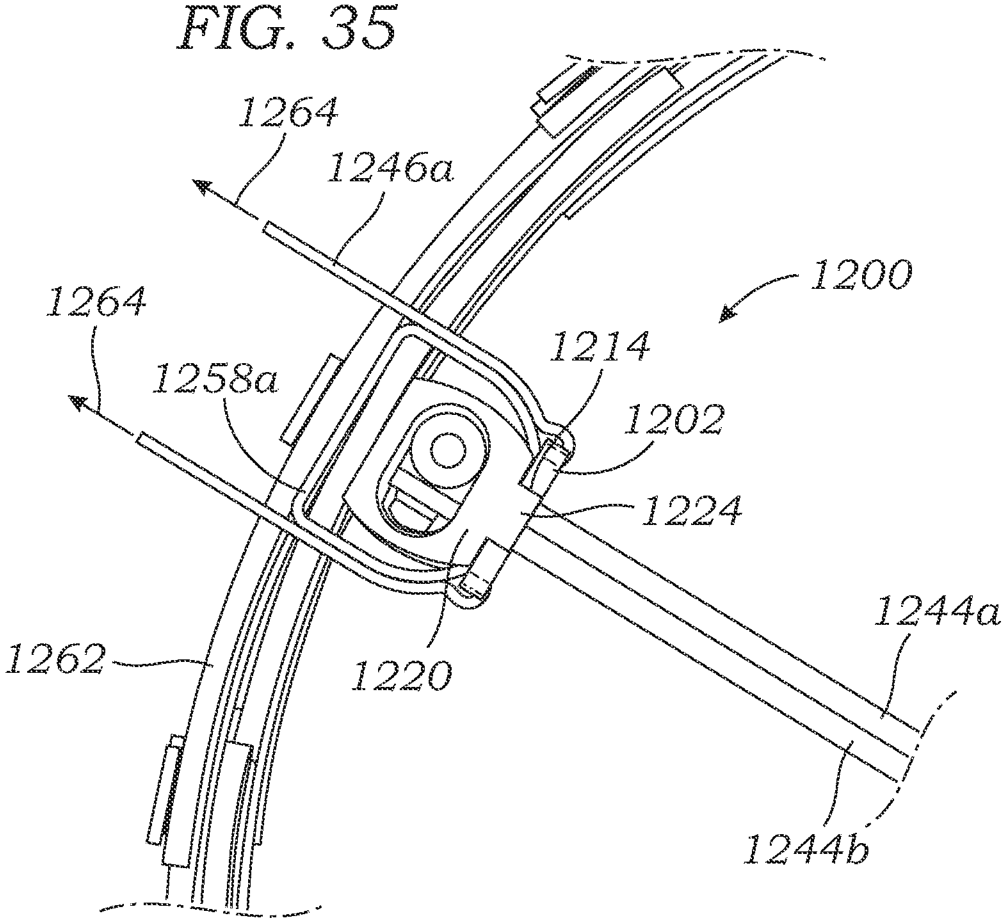
FIG. 35 is a top view of the commissure attachment assembly of FIG. 34, where the support member is arranged against the inner side of the actuator component.

FIGS. 34-35 illustrate a further stage of assembling the commissure attachment assembly 1200, which can include extending the actuator component 1220 of a frame 1262 of a prosthetic heart valve through the loops 1258*a* and 1258*b* of the attachment members 1246*a* and 1246*b*, respectively. For example, as shown in FIG. 34, the assembly including the commissure tabs 1242*a* and 1242*b* and the attachment members 1246*a* and 1246*b* attached to the support member 1202 can be slid in the axial direction, toward the actuator component 1220, as shown by arrow 1260. The loops 1258*a* and 1258*b* can be slid over and around the actuator component 1220, which results in positioning the folded ends of the commissure tabs 1242*a* and 1242*b* and the support member 1202 against the inner side of the actuator component 1220.

FIG. 35 shows a top view of the commissure attachment assembly 1200, where the support member 1202 is arranged against the inner side of the actuator component 1220. For example, the notches 1214 and 1216 of the support member 1202 are received within respective post extensions 1224 and 1226.

The commissure tabs 1244*a* and 1244*b* may be retained between the support member 1202 and the commissure receiving portion 1222 of the actuator component 1220. In this configuration, the upper loop central portion 1258*a* can be aligned with the upper channel 1236 of the actuator component 1220 and the lower loop central portion 1258*b* can be aligned with the lower channel 1238.

As shown in FIG. 35, the loops 1258*a* and 1258*b* can be initially formed with a larger diameter than that of the actuator component 1220 (e.g., there are gaps between an outside of the actuator component 1220 and the loops 1258*a* and 1258*b*). This may allow for the loops 1258*a* and 1258*b* to be more easily slipped over the actuator component 1220, thereby enabling easier assembly of the support member 1202 to the actuator component 1220.

Figure 36:
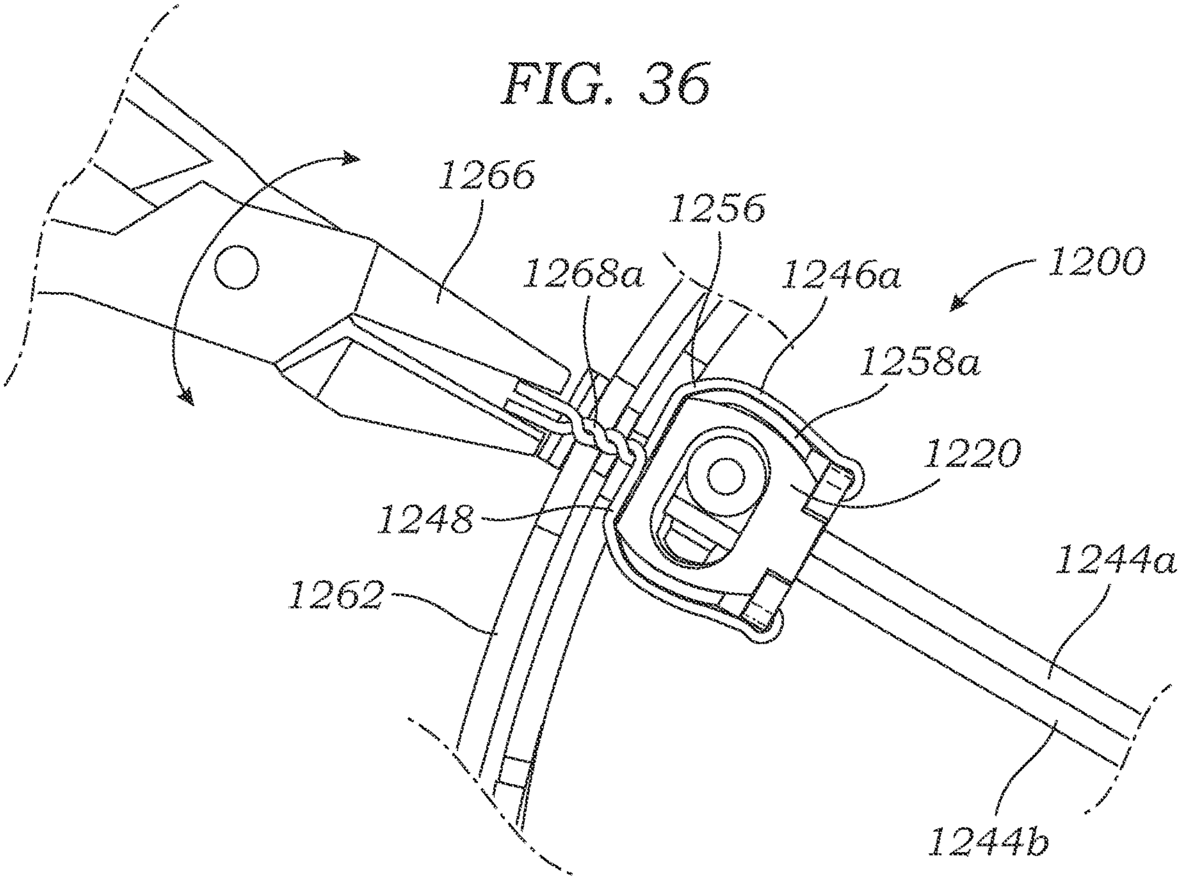
FIG. 36 is a top view of another stage of assembling the commissure attachment assembly of FIG. 34, including tightening and securing ends of each attachment member together and arranging the secured ends within channels of the actuator component.

Once the attachment members 1246*a* and 1246*b* are positioned in place, as shown in FIG. 35, the free ends of the attachment members 1246*a* and 1246*b* can be tightened and/or bent around the actuator component 1220. For example, the attachment members 1246*a* and 1246*b* can be pulled radially outward, as shown by arrows 1264 in FIG. 35, thereby tightening the loops 1258*a* and 1258*b* around the actuator component 1220 (which reduces the diameter of the loops 1258*a* and 1258*b*, as shown in FIG. 36). This results in the loop central portions 1252*a* and 1252*b* being positioned within the respective channels 1236 and 1238 (as shown in FIG. 38).

As shown in FIG. 36, an external tool (e.g., pliers or another twisting tool) 1266 may be utilized to tightly twist the end portions of the first side portion 1248 and second side portion 1256 of each attachment member (e.g., attachment member 1246*a* shown in FIG. 36) together. As a result, the loops 1258*a* and 1258*b* may be retained in their tightened (reduced diameter) state, within the respective channels 1236 and 1238 of the actuator component 1220.

Figure 37:
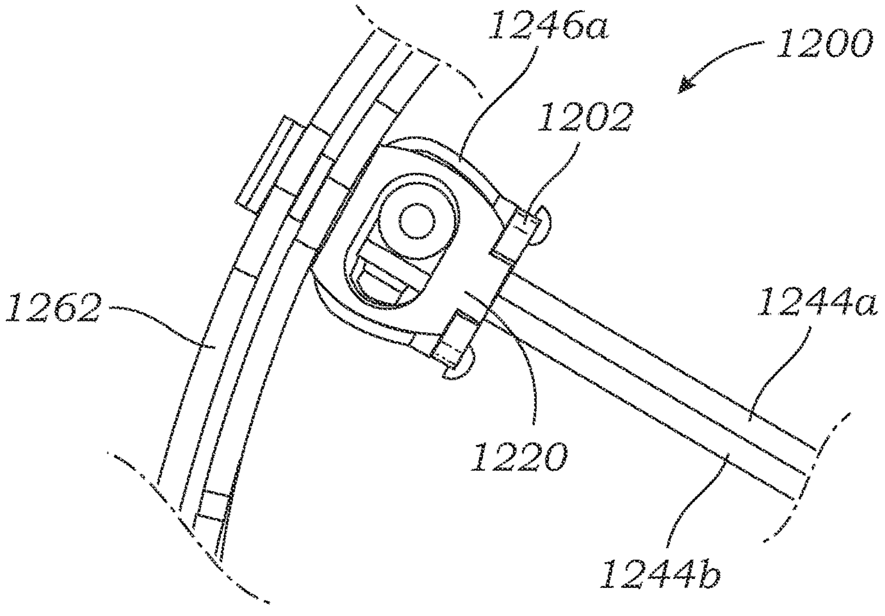
FIG. 37 is a top view of the commissure attachment assembly of FIG. 34, in a tightened and secured state.

In some embodiments, free ends of the attachment members 1246*a* and 1246*b* extending from the resulting twisted portions 1268*a* and 1268*b* may be cut off FIGS. 37 and 38 show a top view and an outer, perspective view, respectively, of the commissure attachment assembly 1200, following attaching the support member to the actuator component 1220, where the end portions of both the upper attachment member 1246*a* and the lower attachment member 1246*b* are twisted together and the twisted portions 1268*a* and 1268*b* are arranged within the central channel 1240 of the actuator component 1220.

As shown in FIG. 38, the lower attachment member 1246*b* is arranged closer to the rivet 1241 of the housing of the actuator component 1220 than the upper attachment member 1246*a*.

In alternate embodiments, the end portions of the side portions 1248 and 1256 of each of the attachment members 1246*a* and 1246*b* may not be twisted together and may instead be positioned adjacent one another and wedged into the central channel 1240 to be tightly retained therein.

In some embodiments, the dimensions of the channels 1236, 1238, and 1240 are selected to accommodate the corresponding portions of the attachment members 1246*a* and 1246*b*, including their twisted portions.

In this way, the channels 1236, 1238, and 1240 formed in the actuator component 1220 allow for easier positioning of the attachment members 1246*a* and 1246*b*, including their respective loops 1258 and twisted portions 1268, during the attachment process of the support member 1202 to the actuator component 1220.

By utilizing attachment members 1246*a* and 1246*b* comprising elastically deformable wires or polymeric materials, the attachment members 1246*a* and 1246*b* may endure higher stresses and may be less prone to tearing or other modes of degradation that may be associated with sutures or other softer components, for example. Further, the method of assembling the commissure attachment assemblies 1200 to the frame may be more easily automated when using elastically deformable wires or polymeric materials. As a result, a skilled user/operator may not be needed, thereby reducing manufacturing time and costs.

FIG. 39 shows the exemplary frame 1262 of a prosthetic heart valve including three circumferentially distributed post members, each comprising an actuator component 1220 having commissure attachment assemblies 1200 attached thereto via elastically deformable attachment members.

In some embodiments, the commissure attachment assembly 1200 may be pre-assembled with the support members 1202 and attachment members (e.g., attachment members 1246*a* and 1246*b*), as shown in FIGS. 32 and 33, which may then be coupled to actuator components 1220 of the frame 1262, as shown in FIGS. 34-39.

In some embodiments, the commissure attachment assemblies 1202 may be pre-wired (or pre-attached) to corresponding actuator components 1220 (apart from the frame) and the assembled actuator components 1220 and commissure attachment assemblies can then be attached to the frame 1262 (e.g., attached to additional actuator components of an actuator).

In this way, a method for assembling a commissure attachment assembly to a frame of a prosthetic heart valve includes: inserting a pair of commissure tabs of a pair of adjacently arranged leaflets into and through the central opening of a support member (e.g., as shown in FIG. 31); extending one or more attachment members through one or more sets of apertures (e.g., smaller openings arranged on either side of the central opening) of the support member, respectively, and creating one or more loops on a side of the support member arranged opposite a side of the support member that faces the leaflets, the one or more loops having a diameter that is larger than an outer diameter of an actuator component adapted to receive and couple to the support member (e.g., as shown in FIGS. 32 and 33); axially aligning the support member and the actuator component so that the support member extends through the one or more loops, the one or more loops line up with corresponding channels on an outer side of the actuator component, and the pair of commissure tabs are arranged between the support member and an inner side of the actuator component (e.g., as shown in FIGS. 34 and 36); tightening the one or more attachment members (e.g., as shown in FIG. 35) so that the one or more loops tighten around the actuator component, within their corresponding channels; and for each attachment member: securing free ends of the attachment member together (e.g., via twisting, as shown in FIGS. 36) and arranging the secured together free ends within an axially extending central channel arranged in the outer surface of the actuator component (e.g., as shown in FIGS. 37-39).

Although the commissure attachment assemblies disclosed herein have been described as being mounted on an actuator component of a prosthetic valve frame, any of the commissure attachment assemblies disclosed herein can be mounted on other portions of a prosthetic valve frame. For example, a frame of a prosthetic valve can have axially extending post members that are separate from the actuator components for mounting the commissure attachment assemblies. In one specific embodiment, a frame can have a plurality of post members corresponding to the number of commissures (e.g., three post members for three commissures), with each post member being mounted to the inner surface of the frame (e.g., to selected struts 26 of the frame) between two adjacent actuator components (e.g., actuator components 32). The post members can be round or square members similar to the actuator components 32, and may passively lengthen and shorten as the frame is expanded and collapsed, and/or may perform other functions independent of radially collapsing and expanding the frame. Alternatively, any of the commissure assemblies disclosed herein can be mounted to post members that are integral struts of the frame of the prosthetic valve.

Also, the cusp edge portions of the leaflets of any of the embodiments of FIGS. 4-39 can be assembled to the frame of the prosthetic valve using any of various techniques or mechanisms. For example, the cusp edge portions of the leaflets can be sutured to an inner skirt (e.g., an inner skirt 122) which in turn can be connected to the frame of the prosthetic valve with sutures, as depicted in FIG. 2A. In other embodiments, the cusp edge portions of the leaflets can be connected (such as with sutures) to an outer skirt of the prosthetic valve. Further details regarding the assembly of the cusp edge portions of the leaflets are disclosed in U.S. Provisional Application No. 62/854,702, U.S. Provisional Application No. 62/797,837, U.S. Provisional Application No. 62/823,905 and U.S. Patent Application Publication No. 2019/0192296.

Further, the commissure attachment assemblies described herein may also be used with prosthetic heart valves that do not have actuators, such as self-expandable prosthetic heart valves or plastically-expandable prosthetic heart valves (e.g., such as those that are expanded to their functional size by inflating a balloon). Examples of self-expandable prosthetic heart valves can be found in U.S. Pat. Nos. 8,652,202, 9,155,619, and U.S. Publication No. 2014/0343670, which are incorporated herein by reference. Examples of plastically-expandable prosthetic heart valves can be found in U.S. Pat. No. 9,393,110, and U.S. Publication No. 2018/0028310, which are incorporated herein by reference.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of a prosthetic valve is its inflow end and the upper end of the prosthetic valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

Unless otherwise indicated, all numbers expressing quantities of components, dimensions, molecular weights, percentages, temperatures, forces, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

The invention claimed is:

1. A prosthetic heart valve, comprising:

an annular frame including a plurality of interconnected strut members, the frame being radially collapsible to a collapsed configuration and radially expandable to an expanded configuration;

a plurality of leaflets situated within the frame, each leaflet comprising opposing commissure tab portions on opposite sides of the leaflet, each commissure tab portion being paired with an adjacent commissure tab portion of an adjacent leaflet to form at least one commissure;

a plurality of post members mounted on an interior surface of the frame;

wherein the at least one commissure comprises a commissure attachment assembly, the commissure attachment assembly comprising a support member, the support member comprising a central opening disposed at least partially around the commissure tab portions such that the commissure tab portions extend through the central opening of the support member;

wherein the commissure tab portions of the commissure attachment assembly are folded around the support member and away from each other; and wherein the commissure attachment assembly is secured to a first post member of the plurality of post members such that the support member is aligned in the radial direction with the first post member and the commissure tab portions are positioned between, in the radial direction, the first post member and the support member, wherein the radial direction is relative to a central longitudinal axis of the frame.

2. The prosthetic heart valve of claim 1, wherein the central opening is bound by two side edge portions, an upper portion and a lower portion of the support member such that the central opening is positioned completely around the commissure tabs portions.

3. The prosthetic heart valve of claim 1, wherein:

one of the leaflets of the commissure attachment assembly is a first leaflet and the other leaflet of the commissure attachment assembly is a second leaflet;

the support member comprises a first row of openings to receive sutures securing the first leaflet to the support member; and the support member comprises a second row of openings offset from the first row of openings, the second row of openings being configured to receive sutures securing the second leaflet to the support member.

4. The prosthetic heart valve of claim 1, wherein the support member is configured to engage with a corresponding recess or extension in the first post member to hold the commissure attachment assembly in place.

5. The prosthetic heart valve of claim 1, wherein:

the frame is a mechanically-expandable frame; and the post members comprise actuator components configured to mechanically expand and collapse the frame.

6. The prosthetic heart valve of any of claim 2, wherein at least a portion of the support member comprises a flexible material and wherein the support member comprises a plurality of spaced apart openings on both sides of the central opening.

7. The prosthetic heart valve of claim 1, wherein the central opening is defined between by two side portions of the support member that are arranged on opposite sides of the central opening, and wherein the support member is configured to clamp the commissure tab portions within the central opening.

8. The prosthetic heart valve of claim 7, wherein the two side portions of the support member are configured to bend toward one another and in an outward radial direction, relative to a central longitudinal axis of the frame, between a relaxed state and a bent state, wherein a width of the central opening is smaller when the support member is in the bent state, wherein the support member is in the bent state when it is secured to the first post member, and wherein inner edges of the central opening are configured to exert a clamping force against the commissure tab portions arranged therein when the support member is in the bent state.

9. The prosthetic heart valve of claim 7, wherein the two side portions of the support member are configured to bend toward one another, around a central longitudinal axis of the support member between a bent state and a released and unbent state, wherein when the support member is in the bent state a width of the central opening is a wider, first width, and wherein when the support member is in the released and unbent state the width of the central opening is a narrower, second width and side edges of the two side portions defining the central opening exert a force against a portion of the commissure tab portions arranged therein.

10. The prosthetic heart valve of claim 7, wherein a width of the central opening is defined between its side edges, wherein inner portions of the two side portions are arranged adjacent to respective side edges of the side edges, and wherein when the commissure tab portions are arranged within the central opening, the inner portions are bent radially outward, relative to a central longitudinal axis of the frame, and are biased against the commissure tab portions.

11. The prosthetic heart valve of claim 1, wherein the support member comprises a plurality of spaced apart openings arranged on both sides of the central opening, and wherein the commissure attachment assembly is secured to the first post member via one or more elastically deformable attachment members, wherein each of the one or more elastically deformable attachment members extends through two oppositely arranged openings of the plurality of openings, loops around an outer side of the actuator member, and has end portions that are arranged within one or more channels that are recessed into a surface of the outer side of the actuator component.

12. A prosthetic heart valve, comprising:

an annular frame including a plurality of interconnected strut members, the frame being radially collapsible to a collapsed configuration and radially expandable to an expanded configuration;

a plurality of leaflets situated within the frame, each leaflet comprising opposing commissure tab portions on opposite sides of the leaflet, each commissure tab portion being paired with an adjacent commissure tab portion of an adjacent leaflet to form at least one commissure; and a plurality of post members mounted on an interior surface of the frame;

wherein the at least one commissure comprises a commissure attachment assembly, the commissure attachment assembly comprising a support member disposed completely around the commissure tab portions such that the commissure tab portions extend through a central opening of the support member, wherein the central opening is bound by two side portions that are disposed on opposite sides of the central opening, an upper portion, and a lower portion of the support member;

wherein at least a portion of the support member comprises a flexible material and is configured to bend in a radially inward or outward direction relative to a central longitudinal axis of the frame;

wherein the commissure attachment assembly is secured to a first post member of the plurality of post members; and wherein the two side portions of the support member apply a clamping force against the commissure tab portions arranged within the central opening.

13. The prosthetic heart valve of claim 12, wherein the support member is configured to bend in an outward radial direction, relative to the central longitudinal axis, from a relaxed state to a bent state, wherein the support member is in the bent state when it is secured to the first post member, and wherein inner edges of the two side portions are arranged closer together when the support member is in the bent state, as compared to the relaxed state, and apply the clamping force against the commissure tab portions arranged therein.

14. The prosthetic heart valve of claim 13, wherein a width of the inner edges of the two side portions, in a radial direction, is wider than a remainder of the two side portions.

15. The prosthetic heart valve of claim 12, wherein the support member is configured to bend around a central longitudinal axis of the support member between a bent state and a released state, the central longitudinal axis of the support member arranged in parallel with the central longitudinal axis of the frame, wherein when the support member is in the bent state a width of the central opening is a wider, first width, and wherein when the support member is in the released state the width of the central opening is a narrower, second width and the two side portions apply the clamping force against the commissure tab portions arranged therein.

16. The prosthetic heart valve of claim 15, wherein the support member is in the released state when the support member is secured to the first post member, and wherein the support member comprises a plastically deformable material.

17. The prosthetic heart valve of claim 12, wherein a width of the central opening is defined between its side edges, wherein inner portions of the two side portions are arranged adjacent to respective side edges of the side edges, and wherein the inner portions are configured to bend in the radially outward direction in response to a force being applied thereto, in the radially outward direction.

18. The prosthetic heart valve of claim 17, wherein when the commissure tab portions are arranged within the central opening, the inner portions are bent radially outward, are biased against the commissure tab portions, and apply the clamping force against the commissure tab portions.

19. The prosthetic heart valve of claim 12, wherein:

the frame is a mechanically-expandable frame; and the post members comprise actuator components configured to mechanically expand and collapse the frame.

20. A method for assembling a commissure attachment assembly to an annular frame of a prosthetic heart valve, comprising:

pairing a first commissure tab of a first leaflet with a second commissure tab of a second leaflet, wherein the first leaflet and the second leaflet are configured to be adjacently arranged within the frame, each leaflet comprising opposing commissure tabs arranged on opposite sides of the leaflet;

inserting the paired first commissure tab and second commissure tab into and through a central opening of a support member that is in a relaxed state, wherein the central opening is defined between two side portions of the support member, and wherein the two side portions are arranged on opposing sides of the central opening;

securing the support member to a post member mounted on an interior surface of the frame; and after inserting the tabs through the opening, bending each of the two side portions of the support member in an outward radial direction, toward the post member, and moving inner edges of the central opening toward each other in order to exert a clamping force against portions of the first and second commissure tabs arranged therein, wherein the radial direction is relative to a central longitudinal axis of the annular frame.

21. The method of claim 20, wherein the securing causes the side portions of the support member to bend from the relaxed state to a bent state, wherein in the bent state the side portions bend toward or around the post member and a width of the central opening is decreased from the relaxed state.

22. The method of claim 20, wherein each side portion includes a plurality of openings and wherein the securing includes extending one or more sutures through at least one side opening in each side portion and to the post member and tightening the sutures to or around the post member.

23. A prosthetic heart valve, comprising:

an annular frame including a plurality of interconnected strut members, the frame being radially collapsible to a collapsed configuration and radially expandable to an expanded configuration, the frame comprising an inflow end and an outflow end;

a plurality of leaflets situated within the frame, each leaflet comprising opposing commissure tab portions on opposite sides of the leaflet, each commissure tab portion being paired with an adjacent commissure tab portion of an adjacent leaflet to form at least one commissure;

a plurality of post members mounted on an interior surface of the frame, and a pair of retaining members attached to each post member, the pair of retaining members spaced apart from each other, wherein each retaining member comprises a base portion directly attached to the post member and a prong member that extends from the base portion toward the outflow end of the frame, wherein the prong member is offset from the post member in a radial direction relative to a central longitudinal axis of the frame, and wherein an end of the prong member opposite the base portion is unattached to the post member and configured to be urged radially toward the post member;

wherein each pair of commissure tab portions extends through a respective pair of retaining members such that the pair of commissure tab portions are folded away from one another and each commissure tab portion is positioned radially between a respective retaining member of the pair of retaining members and the respective post member.

* * * * *